United States Patent
Wang et al.

(10) Patent No.: US 11,590,182 B2
(45) Date of Patent: Feb. 28, 2023

(54) METHODS AND COMPOSITIONS TO MODULATE ANTIBIOTIC RESISTANCE AND GASTROINTESTINAL MICROBIOTA

(71) Applicant: Ohio State Innovation Foundation, Columbus, OH (US)

(72) Inventors: Hua Wang, Columbus, OH (US); Lu Zhang, Columbus, OH (US); Yang Zhou, Columbus, OH (US); Zihua Wang, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 16/566,453

(22) Filed: Sep. 10, 2019

(65) Prior Publication Data

US 2020/0147155 A1    May 14, 2020

Related U.S. Application Data

(60) Provisional application No. 62/729,031, filed on Sep. 10, 2018.

(51) Int. Cl.
| | | |
|---|---|---|
| *A61K 35/747* | (2015.01) | |
| *A23K 10/18* | (2016.01) | |
| *A23K 50/30* | (2016.01) | |
| *A23K 50/75* | (2016.01) | |

(52) U.S. Cl.
CPC ............ *A61K 35/747* (2013.01); *A23K 10/18* (2016.05); *A23K 50/30* (2016.05); *A23K 50/75* (2016.05)

(58) Field of Classification Search
CPC ........ A23K 10/18; A23K 50/30; A23K 50/75; A61K 35/747
See application file for complete search history.

(56) References Cited

U.S. PATENT DOCUMENTS

| | | | |
|---|---|---|---|
| 7,799,551 B2 * | 9/2010 | Nsereko | C12N 9/16 435/252.9 |
| 8,211,672 B2 * | 7/2012 | Nsereko | C12P 5/023 435/71.1 |
| 8,236,537 B2 * | 8/2012 | Ruser | A23K 10/12 435/167 |
| 8,409,642 B2 * | 4/2013 | Nsereko | C12R 1/25 426/54 |
| 9,539,293 B2 | 1/2017 | Kelly | |
| 2004/0247568 A1 * | 12/2004 | Guerino | A23K 50/10 424/93.4 |
| 2005/0202437 A1 * | 9/2005 | Glenn | C07K 14/335 435/6.11 |
| 2005/0233408 A1 * | 10/2005 | Pouwels | C07K 14/335 435/34 |
| 2006/0046292 A1 * | 3/2006 | Nsereko | C12R 1/225 435/252.9 |
| 2009/0010903 A1 * | 1/2009 | Nsereko | C12R 1/24 424/93.45 |
| 2009/0011085 A1 * | 1/2009 | Nsereko | C12R 1/24 426/53 |
| 2009/0162913 A1 * | 6/2009 | Ruser | C12R 1/24 435/167 |
| 2010/0172938 A1 * | 7/2010 | Pouwels | A61P 31/04 424/234.1 |
| 2013/0177540 A1 * | 7/2013 | Nsereko | A23K 10/18 424/93.45 |
| 2013/0309357 A1 | 11/2013 | Mercenier et al. | |
| 2014/0170126 A1 | 7/2014 | Duncker et al. | |
| 2014/0220180 A1 * | 8/2014 | Hendrick | A23K 10/18 426/53 |
| 2014/0315873 A1 | 10/2014 | Beus et al. | |
| 2015/0044172 A1 | 2/2015 | Bicalho et al. | |
| 2016/0279177 A1 | 9/2016 | Kelly et al. | |
| 2017/0042949 A1 | 2/2017 | Penaloza-Vazquez et al. | |
| 2017/0042950 A1 | 2/2017 | Lau et al. | |
| 2017/0333493 A1 | 11/2017 | Ahmer et al. | |
| 2017/0333496 A1 | 11/2017 | Rehberger et al. | |
| 2017/0334994 A1 | 11/2017 | Cowardin et al. | |
| 2017/0340683 A1 | 11/2017 | Petri et al. | |
| 2018/0042972 A1 | 2/2018 | Gould et al. | |
| 2020/0347366 A1 * | 11/2020 | Peracha | C12N 9/1051 |

OTHER PUBLICATIONS

Vranic et al. Antimicrobial Resistance of *Escherichia coli* Strains Isolated From Urine at Outpatient Population: A Single Laboratory Experience. Mater Sociomed. 2016;28(2):121-124.*

Aarestrup, F. M., Bager, F., Jensen, N. E., Madsen, M., Meyling, A., & Wegener, H. C. (1998). Resistance to antimicrobial agents used for animal therapy in pathogenic-zoonotic- and indicator bacteria isolated from different food animals in Denmark: a baseline study for the Danish Integrated Antimicrobial Resistance Monitoring Programme (DANMAP). Apmis, 106(7-12), 745-770.

Adlerberth, I. & Wold, A.E. (2009). Establishment of the gut microbiota in Western infants. Acta paediatrica.98(2):229-38.

Ahmed, N. A., Petersen, F. C., & Scheie, A. A. (2009). AI-2/LuxS is involved in increased biofilm formation by *Streptococcus intermedius* in the presence of antibiotics. Antimicrobial agents and chemotherapy, 53(10): 4258-4263.

(Continued)

*Primary Examiner* — Lynn Y Fan
(74) *Attorney, Agent, or Firm* — Meunier Carlin & Curfman LLC

(57) ABSTRACT

Disclosed herein are methods and compositions related to probiotic formulas. These formulas comprise the bacterial strain *Lactobacillus crispatus* WZ-12 or a derivative thereof. Other strains which can be included in the composition include, but are not limited to, *Lactobacillus salivarius* 1-14, or *Lactobacillus reuteri* 2-2, and derivatives thereof. These compositions can be used in a variety of methods to treat and/or ameliorate diseases, such as colonization of antibiotic-resistant bacteria in the host organism. Also disclosed herein are methods of treating those subjects in need thereof by administering the compositions disclosed herein.

9 Claims, 12 Drawing Sheets
Specification includes a Sequence Listing.

(56) References Cited

OTHER PUBLICATIONS

Akpan, M. R., Ahmad, R., Shebl, N. A., & Ashiru-Oredope, D. (2016). A Review of Quality Measures for Assessing the Impact of Antimicrobial Stewardship Programs in Hospitals. Antibiotics, 5(1), 5.
Alanis, A.J. (2005). Resistance to antibiotics: are we in the post-antibiotic era? Archives of Medical Research. 36(6): 697-705.
AlFaleh, K., & Anabrees, J. (2014). Probiotics for prevention of necrotizing enterocolitis in preterm infants. Evidence-Based Child Health: A Cochrane Review Journal, 9(3), 584-671.
Allen, H. K., Donato, J., Wang, H. H., Cloud-Hansen, K. A., Davies, J., & Handelsman, J. (2010). Call of the wild: antibiotic resistance genes in natural environments.Nature Reviews Microbiology, 8(4), 251-259.
Allignet, J., Loncle, V., & El Solh, N. (1992). Sequence of a staphylococcal plasmid gene, vga, encoding a putative ATP-binding protein involved in resistance to virginiamycin A-like antibiotics. Gene, 117(1), 45-51.
Alonso-Hernando, A., Prieto, M., García-Fernández, C., Alonso-Calleja, C., & Capita, R. (2012). Increase over time in the prevalence of multiple antibiotic resistance among isolates of Listeria monocytogenes from poultry in Spain.Food Control, 23(1), 37-41.
Altschul, Stephen F., et al. "Basic local alignment search tool." Journal of molecular biology 215.3 (1990): 403-410.
Altschul, Stephen F., et al. "Gapped BLAST and PSI-BLAST: a new generation of protein database search programs." Nucleic acids research 25.17 (1997): 3389-3402.
Aminov, R.I. (2010). A brief history of the antibiotic era: lessons learned and challenges for the future. Frontiers in microbiology, 1.
Amit-romach E, Sklan D and Unil Z. (2004) Microflora ecology of the chicken intestine using 16S ribosomal DNA primers. Poultry Science, 83: 1093-1098.
Anadon, A., Martinez-Larrañaga, M. R., Diaz, M. J., Bringas, P., Fernandez, M. C., Fernandez-Cruz, M. L., . . . & Martinez, M. A. (1994). Pharmacokinetics of doxycycline in broiler chickens. Avian pathology, 23(1), 79-90.
Antunes, P., Machado, J., Sousa, J. C., & Peixe, L. (2005). Dissemination of sulfonamide resistance genes (sul1, sul2, and sul3) in Portuguese *Salmonella enterica* strains and relation with integrons. Antimicrobial agents and chemotherapy, 49(2), 836-839.
Antunes, P., Réu, C., Sousa, J. C., Peixe, L., & Pestana, N. (2003). Incidence of *Salmonella* from poultry products and their susceptibility to antimicrobial agents. International journal of food microbiology, 82(2), 97-103.
Apajalahti, J.H., Kettunen, A.A., Bedford, M.R. & Holben, W.E. (2001). Percent G-C profiling accurately reveals diet-related differences in the gastrointestinal microbial community of broiler chickens. Applied Environmental Microbiology, 67:5656-5667.
Asahara, T., Shimizu, K., Nomoto, K., Hamabata, T., Ozawa, A., & Takeda, Y. (2004). Probiotic bifidobacteria protect mice from lethal infection with Shiga toxin-producing *Escherichia coli* O157: H7. Infection and immunity, 72(4), 2240-2247.
Ashraf, R., & Shah, N. P. (2014). Immune system stimulation by probiotic microorganisms. Critical reviews in food science and nutrition, 54(7), 938-956.
Avorn, J., Barrett, J., Davey, P., McEwen, S., O'Brien, T. & Levy, S. (2001). Antibiotic resistance: synthesis of recommendations by expert policy groups. Geneva: World Health Organization.
Aziz, R.K, Bartels D., Best, A.A., DeJongh, M., Disz, T., Edwards, R.A., Formsma, K., Gerdes, S., Glass, E.M., Kubal, M. & Meyer, F. (2008). The RAST Server: rapid annotations using subsystems technology. BMC genomics, 9(1), 1.
Bager, F., Madsen, M., Christensen, J. & Aarestrup, F.M. (1997). Avoparcin used as a growth promoter is associated with the occurrence of vancomycin-resistant Enterococcus faecium on Danish poultry and pig farms. Preventive veterinary medicine, 31(1):95-112.
Ban on antibiotics as growth promoters in animal feed enters into effect. 2005. http://europa.eu/rapid/press-release_IP-05-1687_en.htm. Accessed Jul. 2016.

Baquero, F., Coque, T.M. & de la Cruz, F. (2011). Ecology and evolution as targets: the need for novel eco-evo drugs and strategies to fight antibiotic resistance. Antimicrobial agents and chemotherapy, 55(8):3649-60.
Barnes, E. M., Impey, C. S., & Cooper, D. M. (1980). Manipulation of the crop and intestinal flora of the newly hatched chick. The American journal of clinical nutrition, 33(11), 2426-2433.
Barnes, E.M. (1979). The intestinal microflora of poultry and game birdsduring life and after storage. Journal of Applied Bacteriology, 46:407-419.
Barnes, E.M., Mead, G.C., Barnum, D.A. & Harry, E.G. (1972). The intestinal flora of the chicken in the period 2 to 6 weeks of age, with particular reference to the anaerobic bacteria. British Poultry Science, 13:311-326.
Barthelemy, P., Autissier, D., Gerbaud P., & Courvalin P. (1984). Enzymic hydrolysis of erythromycin by a strain of *Escherichia coli*. A new mechanism of resistance. Journal of Antibiotics (Tokyo), 37, 1692-1696.
Baucheron, S., Nishino, K., Monchaux, I., Canepa, S., Maurel, M. C., Coste, F., Roussel A., Cloeckaert, A. & Giraud, E. (2014). Bile-mediated activation of the acrAB and tolC multidrug efflux genes occurs mainly through transcriptional derepression of ramA in *Salmonella enterica* serovar Typhimurium. Journal of Antimicrobial Chemotherapy, 69(9), 2400-2406.
Bauernfeind, A., Stemplinger, I., Jungwirth, R., Wilhelm, R., & Chong, Y. (1996). Comparative characterization of the cephamycinase blaCMY-1 gene and its relationship with other beta-lactamase genes. Antimicrobial agents and chemotherapy, 40(8), 1926-1930.
Beaber, J. W., Hochhut, B., & Waldor, M. K. (2004). SOS response promotes horizontal dissemination of antibiotic resistance genes. Nature, 427(6969), 72-74.
Beceiro, A., Llobet, E., Aranda, J., Bengoechea, J. A., Doumith, M., Hornsey, M., . . . & Woodford, N. (2011). Phosphoethanolamine modification of lipid A in colistin-resistant variants of Acinetobacter baumannii mediated by the pmrAB two-component regulatory system. Antimicrobial agents and chemo therapy,55(7), 3370-3379.
Belongia, E. A., Knobloch, M. J., Kieke, B. A., Davis, J. P., Janette, C., & Besser, R. E. (2005). Impact of statewide program to promote appropriate antimicrobial drug use. Emerg Infect Dis, 11(6), 912-920.
Bennett, P.M. (2008). Plasmid encoded antibiotic resistance: acquisition and transfer of antibiotic resistance genes in bacteria. British journal of pharmacology, 153(S1):S347-57.
Bensink, J. C., Botham, F. P. (1983). Antibiotic resistant coliform bacilli, isolated from freshly slaughtered poultry and from chilled poultry at retail outlets. Australian veterinary journal, 60(3): 80-83.
Bjarnsholt, T., van Gennip, M., Jakobsen, T.H., Christensen, L.D., Jensen, P.Ø. & Givskov, M. (2010). In vitro screens for quorum sensing inhibitors and in vivo confirmation of their effect. Nature protocols, 5(2):282-93.
Boehm, A., Steiner, S., Zaehringer, F., Casanova, A., Hamburger, F., Ritz, D., Keck, W., Achermaan, M., Schimer, T. & Jenal, U. (2009). Second messenger signalling governs *Escherichia coli* biofilm induction upon ribosomal stress. Molecular microbiology, 72(6), 1500-1516.
Boehr, D.D., Daigle, D., Wright, G.D., (2004) Domain-domain interactions in the aminoglycoside antibiotic resistance enzyme AAC (6'-APH(2"). Biochemistry, 43:9846-9855.
Bonten, M. J., D. J. Austin, & M. Lipsitch. (2001). Understanding the spread of antibiotic resistant pathogens in hospitals: mathematical models as tools for control. Clinical Infectious Diseases, 33:1739-1746.
Bootsma, M. C., O. Diekmann, & M. J. Bonten. (2006). Controlling methicillin-resistant *Staphylococcus aureus*: quantifying the effects of interventions and rapid diagnostic testing. Proceedings of the National Academy of Sciences of the Unite States, 103:5620-5625.
Boucher, H. W., Talbot, G. H., Bradley, J. S., Edwards, J. E., Gilbert, D., Rice, L. B., . . . & Bartlett, J. (2009). Bad bugs, no drugs: no ESKAPE! An update from the Infectious Diseases Society of America. Clinical Infectious Diseases, 48(1), 1-12.
Boudeau, J., Glasser, A. L., Julien, S., Colombel, J. F., & Darfeuille-Michaud, A. (2003). Inhibitory effect of probiotic *Escherichia coli* strain Nissle 1917 on adhesion to and invasion of intestinal epithe-

(56) References Cited

OTHER PUBLICATIONS lial cells by adherent-invasive *E. coli* strains isolated from patients with Crohn's disease.Alimentary pharmacology & therapeutics, 18(1), 45-56.
Bozdogan, B., Berrezouga, L., Kuo, M. S., Yurek, D. A., Farley, K. A., Stockman, B. J., & Leclercq, R. (1999). A new resistance gene, linB, conferring resistance to lincosamides by nucleotidylation in Enterococcus faecium HM1025. Antimicrobial agents and chemotherapy, 43(4), 925-929.
Brettin, T., Davis, J. J., Disz, T., Edwards, R. A., Gerdes, S., Olsen, G. J., . . . & Shukla, M. (2015). RASTtk: a modular and extensible implementation of the RAST algorithm for building custom annotation pipelines and annotating batches of genomes. Scientific reports, 5.
Brisbin, J.T., Gong, J. & Sharif, S. (2008). Interactions between commensal bacteria and the gut-associated immune system of the chicken[J]. Animal Health Research Reviews, 9(01): 101-110.
Brooks, J. P., McLaughlin, M. R., Scheffler, B., & Miles, D. M. (2010). Microbial and antibiotic resistant constituents associated with biological aerosols and poultry litter within a commercial poultry house. Science of the total environment, 408(20), 4770-4777.
Brown, S. A., & Riviere, J. E. (1991). Comparative pharmacokinetics of aminoglycoside antibiotics. Journal of Veterinary Pharmacology and Therapeutics, 14(1), 1-35.
Bryan, K. G., Harp, R. M., Lambert, B. D., Cadle, J. M., & Snider, W. G. (2015). The Effect of Supplemental Probiotics and Spray-Dried Egg Proteins on Piglet Growth Performance Characteristics. Texas Journal of Agriculture and Natural Resources, 28, 1-11.
Busse, H. J., C. Wostmann, and E. P. Bakker. 1992. The bactericidal action of streptomycin: membrane permeabilization caused by the insertion of mistranslated proteins into the cytoplasmic membrane of *Escherichia coli* and subsequent caging of the antibiotic inside the cells: degradation of these proteins. 551-561.
Byarugaba, D. K. (2010). Mechanisms of antimicrobial resistance. InAntimicrobial Resistance in Developing Countries (pp. 15-26). Springer New York.
Cameron, F. H., Obbink, D. J. G., Ackerman, V. P., & Hall, R. M. (1986). Nucleotide sequence of the AAD (2') aminoglycoside adenylyltransferase determinant aadB. Evolutionary relationship of this region with those surrounding aadA in R538-1 and dhfrII in R388. Nucleic acids research,14(21), 8625-8635.
Caporaso, J.G., Kuczynski, J., Stombaugh, J., Bittinger, K., Bushman, F.D., Costello, E.K., Fierer, N., Pena, A.G., Goodrich, J.K., Gordon, J.I., Huttley, G.A. (2010). QIIME allows analysis of high-throughput community sequencing data. Nature methods, 7(5):335-6.
Carattoli, A. (2011). Plasmids in Gram negatives: molecular typing of resistance plasmids. International Journal of Medical Microbiology, 301(8):654-8.
Carattoli, A. (2013). Plasmids and the spread of resistance. International Journal of Medical Microbiology, 303(6):298-304.
Cardenas, A. M., & Palzkill, T. (2015). Beta-Lactam Resistance. Encyclopedia of Metagenomics: Environmental Metagenomics, 45-53.
Casewell, M., Friis, C., Marco, E., McMullin, P., & Phillips, I. (2003). The European ban on growth-promoting antibiotics and emerging consequences for human and animal health. Journal of antimicrobial chemotherapy, 52(2), 159-161.
Castanon, J.I.R. (2007). Review: History of the use of antibiotic as growth promoters in European poultry feeds. Poultry Science. 86: 2466-2471.
Centers for Disease Control and Prevention (CDC). (2013). Antibiotic resistance threats in the United States 2013. http://www.cdc.gov/drugresistance/pdf/ar-threats-2013-508.pdf. Accessed Jul. 15, 2016.
Centers for Disease Control and Prevention (CDC). (2016) Get Smart: Know When Antibiotics Work, http://www.cdc.gov/getsmart/healthcare/. Accessed Jul. 15, 2016.
Chambers, H. F., and M. A. Sande. (1995). Antimicrobial agents: the aminoglycosides, p. 1103-1121. In J. G. Hardman, L. E. Limbird, P. B. Molinoff, R. W. Ruddon, and A. Goodman Gilman (ed.), The pharmacological basis of therapeutics. McGraw-Hill, New York, N.Y.
Chopra, I., & Roberts, M. (2001). Tetracycline antibiotics: mode of action, applications, molecular biology, and epidemiology of bacterial resistance.Microbiology and molecular biology reviews, 65(2), 232-260.
Claverys, J.P., Prudhomme, M., & Martin, B. (2006). Induction of competence regulons as a general response to stress in gram-positive bacteria. Microbiology, 60(1):451.
Collado, M. C., Grześkowiak, Ł., & Salminen, S. (2007). Probiotic strains and their combination inhibit in vitro adhesion of pathogens to pig intestinal mucosa. Current microbiology, 55(3), 260-265.
Collins, E.R., Barker, J.C., Carr, L.E., Brodie, H.L. & Martin, J.H. (1999). Poultry waste management handbook; Tables 1-1, 1-2, 1-5, 1-6 and 1-9, and Figure 2-1. NRAES-132. ISBN 0-935817-42-5. Ithaca, New York, USA, Natural Resource, Agriculture, and Engineering Service (NRAES).
Coloe, P.J., Bagust, T.J. & Ireland, L. (1984) Development of the normal gastrointestinal microflora of specific pathogen-free chickens. The Journal of Hygiene, 92(1):79-87.
Craig, N.L. (1997). Target site selection in transposition. Annual review of biochemistry, 66(1):437-74.
Cromwell, G.L. (2002). Why and how antibiotics are used in swine production. Animal Biotechnology, 13: 7-27.
D'Costa, V. M., King, C. E., Kalan, L., Morar, M., Sung, W. W., Schwarz, C., . . . & Golding, G. B. (2011). Antibiotic resistance is ancient. Nature,477(7365), 457-461.
Davey, P., Brown, E., Charani, E., Fenelon, L., Gould, I. M., Holmes, A., . . . & Wilcox, M. (2013). Interventions to improve antibiotic prescribing practices for hospital inpatients. The Cochrane Library.
Davies, J. (1994). Inactivation of antibiotics and the dissemination of resistance genes. Science, 264(5157), 375-382.
Davies, J. E. (1997). Origins, acquisition and dissemination. Antibiotic resistance: origins, evolution, selection and spread, 787, 15-35.
Delver, E.P., Kotova, V.U., Zavilgelsky, G.B., & Belogurov, A.A. (1991). Nucleotide sequence of the gene (ard) encoding the antirestriction protein of plasmid collb-P9. Journal of bacteriology, 173(18):5887-92.
Depaola, A., Peeler, J.T.&Rodrick, G.E. (1995). Effect of oxytetracycline-medicated feed on antibiotic resistance of gram-negative bacteria in catfish ponds. Applied and Environmental Microbiology. 61(6):2335-40.
Dethlefsen, L., McFall-Ngai, M. & Reiman, D.A. (2007). An ecological and evolutionary perspective on human-microbe mutualism and disease. Nature. 449(7164):811-8.
Diarra, M. S., Silversides, F. G., Diarrassouba, F., Pritchard, J., Masson, L., Brousseau, R., & Topp, E. (2007). Impact of feed supplementation with antimicrobial agents on growth performance of broiler chickens, Clostridium perfringens and Enterococcus counts, and antibiotic resistance phenotypes and distribution of antimicrobial resistance determinants in *Escherichia coli* isolates. Applied and environmental microbiology, 73(20), 6566-6576.
Diarrassouba, F., Diarra, M. S., Bach, S., Delaquis, P., Pritchard, J., Topp, E., & Skura, B. J (2007). Antibiotic resistance and virulence genes in commensal *Escherichia coli* and *Salmonella isolates* from commercial broiler chicken farms. Journal of Food Protection®, 70(6), 1316-1327.
Dibner, J. J., & Richards, J. D. (2005). Antibiotic growth promoters in agriculture: history and mode of action. Poultry science, 84(4), 634-643.
Ditu, L. M., Chifiriuc, M. C., Bezirtzoglou, E., Voltsi, C., Bleotu, C., Pelinescu, D., . . . & Lazar, V. (2011). Modulation of virulence and antibiotic susceptibility of enteropathogenic *Escherichia coli* strains by Enterococcus faecium probiotic strain culture fractions. Anaerobe, 17(6), 448-451.
Dmowski, M. & Jagura-Burdzy, G. (2013). Active stable maintenance functions in low copy-number plasmids of Gram-positive bacteria I. Partition systems. Polish Journal of Microbiology, 62(1):3-16.

(56) References Cited

OTHER PUBLICATIONS

Dolejska, M., Villa, L., Poirel, L., Nordmann, P. & Carattoli, A. (2013). Complete sequencing of an IncHI1 plasmid encoding the carbapenemase NDM-1, the ArmA 16S RNA methylase and a resistance nodulation cell division/multidrug efflux pump. Journal of Antimicrobial Chemotherapy, 68, 34-39.

Dorrestein, G. V., Van Gogh, H., & Rinzema, J. D. (1984). Pharmacokinetic aspects of penicillins, aminoglycosides and chloramphenicol in birds compared to mammals. A review. Veterinary quarterly, 6(4), 216-224.

Dotterud, C. K., Storrø, O., Johnsen, R., & Øien, T. (2010). Probiotics in pregnant women to prevent allergic disease: a randomized, double-blind trial. British Journal of Dermatology, 163(3), 616-623.

Dowling, P.M. (2006) Miscellaneous antimicrobials: Ionophores, nitrofurans, nitroimidazoles, rifamycins, and others. 2013 John Wiley & Sons, Inc. 315-332.

D'Souza, A. L., Rajkumar, C., Cooke, J., & Bulpitt, C. J. (2002). Probiotics in prevention of antibiotic associated diarrhoea: meta-analysis. Bmj, 324(7350), 1361.

Duffy, E.A., Lucia, L.M., Kells, J.M., Castillo, A., Pillai, S.D. & Acuff, G.R. (2005). Concentrations of *Escherichia coli* and genetic diversity and antibiotic resistance profiling of *Salmonella* isolated from irrigation water, packing shed equipment, and fresh produce in Texas. Journal of Food Protection. 68(1):70-9.

DuráN, G. M., & Marshall, D. L. (2005). Ready-to-eat shrimp as an international vehicle of antibiotic-resistant bacteria. Journal of Food Protection®, 68(11), 2395-2401.

Durso, L. M., Smith, D., & Hutkins, R. W. (2004). Measurements of fitness and competition in commensal *Escherichia coli* and *E. coli* O157: H7 strains.Applied and environmental microbiology, 70(11), 6466-6472.

Dworkin, R. J. (1999) Aminoglycosides for the treatment of gram-negative infections: therapeutic use, resistance and future outlook. Drug Resistance Update 2:173-179.

Dyda, F., Klein, D. C., & Hickman, A. B. (2000). GCN5-related N-acetyltransferases: a structural overview. Annual review of biophysics and biomolecular structure, 29(1), 81-103.

Economic and Social Committee of the European Union. (1998). Opinion on resistance to antibiotics as a threat to public health. No. ESC-98-016-EN. Accessed Jul. 2016.

Egea, P., López-Cerero, L., Torres, E., del Carmen Gómez-Sánchez, M., Serrano, L., Sánchez-Ortiz, M.D., Rodriguez-Baño, J. & Pascual, A. (2012). Increased raw poultry meat colonization by extended spectrum beta-lactamase-producing *Escherichia coli* in the south of Spain. International journal of food microbiology, 159(2):69-73.

Ehmann, D. E., Jahić, H., Ross, P. L., Gu, R. F., Hu, J., Kern, G., . . . & Fisher, S. L. (2012). Avibactam is a covalent, reversible, non-β-lactam β-lactamase inhibitor. Proceedings of the National Academy of Sciences, 109(29), 11663-11668.

Elliott, S. D. & Barnes, E. M. (1959). Changes in serological type and antibiotic resistance on Lancefield group D streptococci in chickens receiving dietary chlortetracycline. J. Gen.Microbiol. 20:426-433.

Esposito, E., Iacono, A., Bianco, G., Autore, G., Cuzzocrea, S., Vajro, P., . . . & Meli, R. (2009). Probiotics reduce the inflammatory response induced by a high-fat diet in the liver of young rats. The Journal of nutrition, 139(5), 905-911.

European Commission. (2005). Regulation 1831/2003/EC on additives for use in animal nutrition, replacing Directive 70/524/EEC on additives in feeding-stuffs. European Commission Press releases database.

Fabia, R., Ar'Rajab, A., Johansson, M. L., Willen, R., Andersson, R., Molin, G., & Bengmark, S. (1993). The effect of exogenous administration of Lactobacillus reuteri R2LC and oat fiber on acetic acid-induced colitis in the rat. Scandinavian journal of gastroenterology, 28(2), 155-162.

Fairchild, A. S., Smith, J. L., Idris, U., Lu, J., Sanchez, S., Purvis, L. B., . . . & Lee, M. D. (2005). Effects of orally administered tetracycline on the intestinal community structure of chickens and on tet determinant carriage by commensal bacteria and Campylobacter jejuni. Applied and environmental microbiology, 71(10), 5865-5872.

Fillgrove, K.L., Pakhomova, S., Newcomer, M.E. & Armstrong, R.N. (2003). Mechanistic diversity of fosfomycin resistance in pathogenic microorganisms. Journal of the American Chemical Society. 125,15730-15731.

Fluit, A. C., & Schmitz, F. J. (1999). Class 1 integrons, gene cassettes, mobility, and epidemiology. European Journal of Clinical Microbiology and Infectious Diseases, 18(11), 761-770.

Food and Agriculture Organization of the United Nation (FAO). (2013). Statistical Yearbook 2013: World Food and Agriculture. Food and Agriculture Organization of the United Nations, Rome, 289.p. 140.

Frazier, D. L., Jones, M. P., & Orosz, S. E. (1995). Pharmacokinetic considerations of the renal system in birds: part II. Review of drugs excreted by renal pathways. Journal of Avian Medicine and Surgery, 104-121.

Fridkin, S., Baggs, J., Fagan, R., Magill, S., Pollack, L. A., Malpiedi, P., . . . & Samore, M. H. (2014). Vital signs: improving antibiotic use among hospitalized patients. MMWR. Morbidity and mortality weekly report, 63(9), 194-200.

Fritsche, T. R., Castanheira, M., Miller, G. H., Jones, R. N. & Armstrong, E. S. (2008). Detection of methyltransferases conferring high-level resistance to aminoglycosides in Enterobacteriaceae from Europe, North America, and Latin America. Antimicrobial Agents Chemotherapy, 52, 1843-1845.

Fuller, R. (1992). History and development of probiotics. In Probiotics (pp. 1-8). Springer Netherlands.

Furrie, E., Macfarlane, S., Kennedy, A., Cummings, J. H., Walsh, S. V., O'neil, D. A., & Macfarlane, G. T. (2005). Synbiotic therapy (Bifidobacterium longum/Synergy 1) initiates resolution of inflammation in patients with active ulcerative colitis: a randomised controlled pilot trial. Gut, 54(2), 242-249.

Gao, W., Chua, K., Davies, J. K., Newton, H. J., Seemann, T., Harrison, P. F., . . . & Stinear, T. P. (2010). Two novel point mutations in clinical *Staphylococcus aureus* reduce linezolid susceptibility and switch on the stringent response to promote persistent infection. PLoS Pathog, 6(6), e1000944.

Giguere, S. (2013) Macrolides, azalides, and ketolides. In Antimicrobial Therapy in Veterinary Medicine. Eds Giguere, S., Prescott, J.F., Baggot, J.D., Walker, R.D. & Dowling, P.M., pp. 191-206. Blackwell Publishing, Ames, IA.

Giguère, S. (2013). Lincosamides, pleuromutilins, and streptogramins. Antimicrobial Therapy in Veterinary Medicine, Fifth Edition, 211-231.

Gionchetti, P., Rizzello, F., Lammers, K. M., Morselli, C., Sollazzi, L., Davies, S., Tambasco, R., Calabrese, C., & Campieri, M. (2006). Antibiotics and probiotics in treatment of inflammatory bowel. World J Gastroenterol, 12(21), 3306-3313.

Gish, Warren, and David J. States. "Identification of protein coding regions by database similarity search." Nature genetics 3.3 (1993): 266-272.

Goetting, V., Lee, K. A., & Tell, L. A. (2011). Pharmacokinetics of veterinary drugs in laying hens and residues in eggs: a review of the literature. Journal of veterinary pharmacology and therapeutics, 34(6), 521-556.

Gotteland, M., Brunser, O., & Cruchet, S. (2006). Systematic review: are probiotics useful in controlling gastric colonization by Helicobacter pylori?.Alimentary pharmacology & therapeutics, 23(8), 1077-1086.

Götz, A., Pukall, R., Smit, E., Tietze, E., Prager, R., Tschape, H., . . . & Smalla, K. (1996). Detection and characterization of broad-host-range plasmids in environmental bacteria by PCR. Applied and Environmental Microbiology,62(7), 2621-2628.

Graham, D.Y. & Fischbach, L. (2010). Helicobacter pylori treatment in the era of increasing antibiotic resistance. Gut, gut—2009, 59:1143e1153.

Grozdanov, L., Raasch, C., Schulze, J., Sonnenborn, U., Gottschalk, G., Hacker, J., & Dobrindt, U. (2004). Analysis of the genome structure of the nonpathogenic probiotic *Escherichia coli* strain Nissle 1917. Journal of bacteriology, 186(16), 5432-5441.

(56) References Cited

OTHER PUBLICATIONS

Gryczan, T. J., Grandi, G., Hahn, J., Grandi, R., & Dubnau, D. (1980). Conformational alteration of mRNA structure and the posttranscriptional regulation of erythromycin-induced drug resistance. Nucleic acids research,8(24), 6081-6097.

Hagedorn, C., Robinson, S. L., Filtz, J. R., Grubbs, S. M., Angier, T. A., & Reneau, R. B. (1999). Determining sources of fecal pollution in a rural Virginia watershed with antibiotic resistance patterns in fecal streptococci.Applied and Environmental Microbiology, 65(12), 5522-5531.

Hao, Q., Lu, Z., Dong, B. R., Huang, C. Q., & Wu, T. (2011). Probiotics for preventing acute upper respiratory tract infections. The Cochrane Library.

Hart, W. S., Heuzenroeder, M. W., & Barton, M. D. (2006). A study of the transfer of tetracycline resistance genes between *Escherichia coli* in the intestinal tract of a mouse and a chicken model. Journal of Veterinary Medicine, Series B, 53(7), 333-340.

Hasman, H., Mevius, D., Veldman, K., Olesen, I., & Aarestrup, F. M. (2005). β-Lactamases among extended-spectrum β-lactamase (ESBL)-resistant *Salmonella* from poultry, poultry products and human patients in the Netherlands. Journal of Antimicrobial Chemotherapy, 56(1), 115-121.

Hatch, R. A., & Schiller, N. L. (1998). Alginate Lyase Promotes Diffusion of Aminoglycosides through the Extracellular Polysaccharide of MucoidPseudomonas aeruginosa. Antimicrobial agents and chemotherapy,42(4), 974-977.

Hayes, J. R., English, L. L., Carr, L. E., Wagner, D. D., & Joseph, S. W. (2004). Multiple-antibiotic resistance of *Enterococcus* spp. isolated from commercial poultry production environments. Applied and Environmental Microbiology, 70(10), 6005-6011.

Hempel, S., Newberry, S. J., Maher, A. R., Wang, Z., Miles, J. N., Shanman, R., Johnsen, B.,& Shekelle, P. G. (2012). Probiotics for the prevention and treatment of antibiotic-associated diarrhea: a systematic review and meta-analysis. Jama,307(18), 1959-1969.

Heuer, H., Schmitt, H. & Smalla K. (2011). Antibiotic resistance gene spread due to manure application on agricultural fields. Current opinion in microbiology, 14(3):236-243.

Hill, C., Guarner, F., Reid, G., Gibson, G. R., Merenstein, D. J., Pot, B., . . . & Calder, P. C. (2014). Expert consensus document: The International Scientific Association for Probiotics and Prebiotics consensus statement on the scope and appropriate use of the term probiotic. Nature Reviews Gastroenterology & Hepatology, 11(8), 506-514.

Hilleringmann, M., Pansegrau, W., Doyle, M., Kaufman, S., MacKichan, M.L., Gianfaldoni, C., Ruggiero, P. & Covacci, A. (2006). Inhibitors of Helicobacter pylori ATPase Cagα block CagA transport and cag virulence. Microbiology, 152(10):2919-30.

Hooper, L.V. & Gordon, J.I. (2001). Commensal host-bacterial relationships in the gut. Science, 292(5519):1115-8.

Hooper, L.V. (2004). Bacterial contributions to mammalian gut development. Trends in microbiology, 12(3):129-34.

Hoveyda, N., Heneghan, C., Mahtani, K. R., Perera, R., Roberts, N., & Glasziou, P. (2009). A systematic review and meta-analysis: probiotics in the treatment of irritable bowel syndrome. Bmc Gastroenterology, 9(1), 1.

http://www.unsystem.org/SCN/archives/scnnews21/ch04.htm#TopOfPage. Nutrition and the Environment Overview, Rainer Gross and Noel Solomons. Accessed in Jul. 2016.

Hu, Y., Yang, X., Qin, J., Lu, N., Cheng, G., Wu, N., .Pan, Y., Li, J., Zhu, L., Wang, X. & Meng, Z. (2013). Metagenome-wide analysis of antibiotic resistance genes in a Targe cohort of human gut microbiota. Nature communications, 4.

Huang, Y., Zhang, L., Tiu, L., & Wang, H. H. (2015). Characterization of antibiotic resistance in commensal bacteria from an aquaculture ecosystem. Frontiers in microbiology, 6.

Illumina surport. (2013). 16S Metagenomic Sequencing Library Preparation. https://support.illumina.com/downloads/16s_metagenomic_sequencing_library_preparation.html.

Isolauri, E., Siitas, Y., Kankaanpää, P., Arvilommi, H., & Salminen, S. (2001). Probiotics: effects on immunity. The American journal of clinical nutrition,73(2), 444s-450s.

Jacoby, G.A., (2009). Amp C beta-lactamases. Clinical Microbiology Reviews, ;22(1):161-182.

Jernberg, C., Löfmark, S., Edlund, C., & Jansson, J. K. (2007). Long-term ecological impacts of antibiotic administration on the human intestinal microbiota. The ISME journal, 1(1), 56-66.

Johnson, T.J., Lang, K.S. (2012). IncA/C plasmids: An emerging threat to human and animal health? Mobile genetic elements, 2(1):55-8.

Johnston, B. C., Ma, S. S., Goldenberg, J. Z., Thorlund, K., Vandvik, P. O., Loeb, M., & Guyatt, G. H. (2012). Probiotics for the prevention of Clostridium difficile-associated diarrhea: a systematic review and meta-analysis. Annals of internal medicine, 157(12), 878-888.

Jongbloed, A.W. & Lenis, N.P. (1998). Environmental concerns about animal manure. Journal of Animal Science. 76(10):2641-8.

Kaatz, G. W., Thyagarajan, R. V., & Seo, S. M. (2005). Effect of promoter region mutations and mgrA overexpression on transcription of norA, which encodes a *Staphylococcus aureus* multidrug efflux transporter. Antimicrobial agents and chemotherapy, 49(1), 161-169.

Kannan, K., & Mankin, A. S. (2011). Macrolide antibiotics in the ribosome exit tunnel: species-specific binding and action. Annals of the New York Academy of Sciences, 1241(1), 33-47.

Kaplan, J. B. (2011). Antibiotic-induced biofilm formation. International journal of Artificial Organs, 34(9): 737-751.

Karami, N., Martner, A., Enne, V. I., Swerkersson, S., Adlerberth, I., & Wold, A. E. (2007). Transfer of an ampicillin resistance gene between two *Escherichia coli* strains in the bowel microbiota of an infant treated with antibiotics. Journal of antimicrobial chemotherapy, 60(5), 1142-1145.

Kassam, Z., Hundal, R., Marshall, J. K., & Lee, C. H. (2012). Fecal transplant via retention enema for refractory or recurrent Clostridium difficile infection. Archives of internal medicine, 172(2), 191-193.

Kim, S. R., & Komano, T. (1997). The plasmid R64 thin pilus identified as a type IV pilus. Journal of bacteriology, 179(11), 3594-3603.

Knapp, C. W., Dolfing, J., Ehlert, P. A., & Graham, D. W. (2009). Evidence of increasing antibiotic resistance gene abundances in archived soils since 1940. Environmental science & technology, 44(2), 580-587.

Kohanski, M. A., DePristo, M. A., & Collins, J. J. (2010). Sublethal antibiotic treatment leads to multidrug resistance via radical-induced mutagenesis.Molecular cell, 37(3), 311-320.

Kopecko, D. J. (1980). Specialized genetic recombination systems in bacteria: their involvement in gene expression and evolution. In Progress in molecular and subcellular biology (pp. 135-234). Springer Berlin Heidelberg.

Kroll, J., Klinter, S., Schneider, C., & Steinbüchel, A. (2010). Plasmid addiction systems: perspectives and applications in biotechnology. Microbial biotechnology, 3(6):634-57.

Kuitunen, M., Kukkonen, K., Juntunen-Backman, K., Korpela, R., Poussa, T., Tuure, T., Haahtela, T., & Savilahti, E. (2009). Probiotics prevent IgE-associated allergy until age 5 years in cesarean-delivered children but not in the total cohort.Journal of Allergy and Clinical Immunology, 123(2), 335-341.

Lakhotia, R. L., Stephens, J. F. (1973). Drug resistance and R factors among enterobacteria isolated from eggs. Poultry science, 52(5): 1955-1962.

Lavigne, J. P., Sotto, A., Nicolas-Chanoine, M. H., Bouziges, N., Pagès, J. M., & Davin-Regli, A. (2013). An adaptive response of Enterobacter aerogenes to imipenem: regulation of porin balance in clinical isolates.International journal of antimicrobial agents, 41(2), 130-136.

Laxminarayan, R., Duse, A., Wattal, C., Zaidi, A. K., Wertheim, H. F., Sumpradit, N., . . . & Greko, C. (2013). Antibiotic resistance—the need for global solutions. The Lancet infectious diseases, 13(12), 1057-1098.

Leach, D. & Symonds, N. (1979). The isolation and characterisation of a plaque-forming derivative of bacteriophage Mu carrying a

(56) References Cited

OTHER PUBLICATIONS fragment of Tn3 conferring ampicillin resistance. Molecular and General Genetics, 172(2):179-84.

Leclercq, R. & Courvalin, P. (1991). Bacterial resistance to macrolide, lincosamide, and streptogramin antibiotics by target modification. Antimicrobial Agents and Chemotherapy 35, 1267-72.

Levings, R.S., Partridge, S.R., Lightfoot, D., Hall, R.M., & Djordjevic, S.P. (2005) New integron-associated gene cassette encoding a 3-Naminoglycoside acetyltransferase. Antimicrobial Agents Chemotherapy, 49:1238-1241.

Levy, S.B. (1978). Emergence of antibiotic-resistant bacteria in the intestinal flora of farm inhabitants. Journal of Infectious Diseases, 137:688-690.

Levy, S.B., Marshall, B., Schluederberg, S., Rowse, D.& Davis, J. (1988). High frequency of antimicrobial resistance in human fecal flora. Antimicrobial agents and chemotherapy, 32(12):1801-6.

Lewicki, J., Reeves, P.T. & Swan, G.E. (2008) Residue Evaluation of Certain Veterinary Drugs, 70th meeting of the Joint FAO/WHO Expert Committee on Food Additives, 243-279.

Lewis, K. (2013). Platforms for antibiotic discovery. Nature reviews Drug discovery, 12(5), 371-387.

Li D, Yang M, Hu J, Zhang J, Liu R, Gu X, Zhang Y, Wang Z. (2009). Antibiotic-resistance profile in environmental bacteria isolated from penicillin production wastewater treatment plant and the receiving river. Environmental microbiology, 11(6):1506-17.

Li, X. & Wang, H. H. (2010). Tetracycline resistance associated with commensal bacteria from representative ready-to-consume deli and restaurant foods. Journal of Food Protection, 73(10): 1841-1848.

Li, X., Li, Y., Alvarez, V., Harper, W. J., & Wang, H. H. (2011). Effective antibiotic resistance mitigation during cheese fermentation. Applied and environmental microbiology, 77(20), 7171-7175.

Lievin-Le Moal, V., Amsellem, R., Servin, A. L., & Coconnier, M. H. (2002). Lactobacillus acidophilus (strain LB) from the resident adult human gastrointestinal microflora exerts activity against brush border damage promoted by a diarrhoeagenic *Escherichia coli* in human enterocyte-like cells.Gut, 50(6), 803-811.

Lin, J., Hunkapiller, A. A., Layton, A. C., Chang, Y. J., & Robbins, K. R. (2013). Response of intestinal microbiota to antibiotic growth promoters in chickens. Foodborne pathogens and disease, 10(4), 331-337.

Linton, A. H., Howe, K., Richmond, M. H., Clements, H. M., Osborne, A. D., & Handley, B. (1978). Attempts to displace the indigenous antibiotic resistant gut flora of chicken by feeding sensitive strains of *Escherichia coli* prior to slaughter. Journal of Applied Bacteriology, 45(2), 239-247.

Liu, B., Pop, M. (2009). ARDB-Antibiotic Resistance Genes Database. Nucleic Acids Research, 37(Database issue):D443-7.

Looft, T., Johnson, T.A., Allen, H.K., Bayles, D.O., Alt, D.P., Stedtfeld, R.D., Sul, W.J., Stedtfeld, T.M., Chai, B., Cole, J.R. & Hashsham, S.A.(2012). In-feed antibiotic effects on the swine intestinal microbiome. Proceedings of the National Academy of Sciences, 109(5):1691-6.

Lu, J., Idris, U., Harmon, B., Hofacre, C., Maurer, J.J. & Lee, M.D. (2003). Diversity and succession of the intestinal bacterial community of the maturing broiler chicken. Applied Environmental Microbiology, 69(11):6816-24.

Lujan, S.A., Guogas, L.M., Ragonese, H., Matson, S.W. & Redinbo, M.R. (2007).Disrupting antibiotic resistance propagation by inhibiting the conjugative DNA relaxase. Proceedings of the National Academy of Sciences, 104(30):12282-7.

Luo, N., Pereira, S., Sahin, O., Lin, J., Huang, S., Michel, L., & Zhang, Q. (2005). Enhanced in vivo fitness of fluoroquinolone-resistant Campylobacter jejuni in the absence of antibiotic selection pressure. Proceedings of the National Academy of Sciences of the United States of America, 102(3), 541-546.

Lynch III, J. P., Clark, N. M., & Zhanel, G. G. (2013). Evolution of antimicrobial resistance among Enterobacteriaceae (focus on extended spectrum β-lactamases and carbapenemases). Expert opinion on pharmacotherapy, 14(2), 199-210.

Mack, D. R., Michail, S., Wei, S., McDougall, L., & Hollingsworth, M. A. (1999). Probiotics inhibit enteropathogenic E. coliadherence in vitro by inducing intestinal mucin gene expression. American Journal of Physiology-Gastrointestinal and Liver Physiology, 276(4), G941-G950.

Madden, Thomas L., Roman L. Tatusov, and Jinghui Zhang. "[9] Applications of network BLAST server." Methods in enzymology. vol. 266. Academic Press, 1996. 131-141.

Madsen, K. L., Doyle, J. S., Jewell, L. D., Tavernini, M. M., & Fedorak, R. N. (1999). *Lactobacillus* species prevents colitis in interleukin 10 gene-deficient mice. Gastroenterology, 116(5), 1107-1114.

Madsen, K., Cornish, A., Soper, P., McKaigney, C., Jijon, H., Yachimec, C., . . . & De Simone, C. (2001). Probiotic bacteria enhance murine and human intestinal epithelial barrier function. Gastroenterology, 121(3), 580-591.

Majiduddin, F. K., Materon, I. C., & Palzkill, T. G. (2002). Molecular analysis of beta-lactamase structure and function. International journal of medical microbiology, 292(2), 127-137.

Malani, A. N., Richards, P. G., Kapila, S., Otto, M. H., Czerwinski, J., & Singal, B. (2013). Clinical and economic outcomes from a community hospital's antimicrobial stewardship program. American journal of infection control, 41(2), 145-148.

Mao, Y., Nobaek, S., Kasravi, B., Adawi, D, Stenram, U., Molin, G, & Jeppsson, B. (1996). The effects of Lactobacillus strains and oat fiber on methotrexate-induced enterocolitis in rats. Gastroenterology, 111(2), 334-344.

Maravic, G. (2004). Macrolide resistance based on the Erm-mediated rRNA methylation. Current Drug Targets-Infectious Disorders, 4(3), 193-202.

Marshall, B.M., Ochieng, D.J. & Levy, S.B. (2009) Commensals: underappreciated reservoir of antibiotic resistance. Microbe, 4(5):231-8.

Martínez, J. L. (2008). Antibiotics and antibiotic resistance genes in natural environment. Science, 321(5887): 365-367.

Mathew, A.G., Cissell, R. & Liamthong, S. (2007). Antibiotic resistance in bacteria associated with food animals: a United States perspective of livestock production. Foodborne Pathogens and Disease, 4(2):115-33.

Matsuoka, M., Endou, K., Kobayashi, H., Inoue, M., & Nakajima, Y. (1998). A plasmid that encodes three genes for resistance to macrolide antibiotics in *Staphylococcus aureus*. FEMS Microbiology Letters, 167(2), 221-227.

McArthur, A. G., Waglechner, N., Nizam, F., Yan, A., Azad, M. A., Baylay, A. J., . . . & Kalan, L. (2013). The comprehensive antibiotic resistance database.Antimicrobial agents and chemotherapy, 57(7), 3348-3357.

McFarland, L. V. (2006). Meta-analysis of probiotics for the prevention of antibiotic associated diarrhea and the treatment of Clostridium difficile disease. The American journal of gastroenterology, 101(4), 812-822.

McKay, G.A., & Wright, G.D. (1995). Kinetic mechanism of aminoglycoside phosphotransferase type IIIa: evidence for a Theorell-Chance mechanism. Journal of Biological Chemistry, 270:24686-24692.

Mead, G.C. (1989). Microbes of the avian cecum: types present and substrates utilized. Journal of Experimental Zoology. 3(Suppl.):48-54.

Meier, A., Kirschner, P., Bange, F. C., Vogel, U., & Böttger, E. C. (1994). Genetic alterations in streptomycin-resistant *Mycobacterium tuberculosis*: mapping of mutations conferring resistance. Antimicrobial agents and chemotherapy, 38(2), 228-233.

Melancon, P., W. E. Tapprich, and L. Brakier-Gingras. (1992). Single-base mutations at position 2661 of *Escherichia coli* 23S rRNA increase efficiency of translational proofreading. J. Bacteriol. 174:7896-7901.

Mennigen, R., Nolte, K., Rijcken, E., Utech, M., Loeffler, B., Senninger, N., & Bruewer, M. (2009). Probiotic mixture VSL# 3 protects the epithelial barrier by maintaining tight junction protein expression and preventing apoptosis in a murine model of colitis. American journal of physiology—Gastrointestinal and liver physiology, 296(5), G1140-G1149.

(56) References Cited

OTHER PUBLICATIONS

Modi, S.R., Lee, H.H., Spina, C.S. & Collins, J.J. (2013). Antibiotic treatment expands the resistance reservoir and ecological network of the phage metagenome. Nature, 499(7457):219-22.

Moore, P. A., Daniel, T. C., Sharpley, A. N., & Wood, C. W. (1995). Poultry manure management: Environmentally sound options. Journal of soil and water conservation, 50(3), 321-327.

Moore, P. R., A. Evenson, T. D. Luckey, E. McCoy, E. A. Elvehjem, and E. B. Hart. (1946). Use of sulphasuccidine, streptothricin and streptomycin in nutrition studies with the chick. J. Biol. Chem, 165:437-441.

Moubareck, C., Lecso, M., Pinloche, E., Butel, M. J., & Doucet-Populaire, F. (2007). Inhibitory impact of bifidobacteria on the transfer of β-lactam resistance among Enterobacteriaceae in the gnotobiotic mouse digestive tract. Applied and environmental microbiology, 73(3), 855-860.

Musa, H. H., & Seri, H. (2009). The potential benefits of probiotics in animal production and health. 313-321.

Muyzer, G., De Waal, E. C., & Uitterlinden, A. G. (1993). Profiling of complex microbial populations by denaturing gradient gel electrophoresis analysis of polymerase chain reaction-amplified genes coding for 16S rRNA. Applied and environmental microbiology, 59(3): 695-700.

Naderi, A., Kasra-Kermanshahi, R., Gharavi, S., Fooladi, A. A. I., Alitappeh, M. A., & Saffarian, P. (2014). Study of antagonistic effects of Lactobacillus strains as probiotics on multi drug resistant (MDR) bacteria isolated from urinary tract infections (UTIs). Iranian journal of basic medical sciences, 17(3), 201.

Nadkarni, M. A., F. E. Martin, N. A. Jacques, and N. Hunter. (2002). Determination of bacterial load by real-time PCR using a broad-range (universal) probe and primers set. Microbiology 148:257-266.

Nagy, Z. & Chandler, M. (2004). Regulation of transposition in bacteria. Research in microbiology, 155(5):387-98.

Ng, S. C., Hart, A. L., Kamm, M. A., Stagg, A. J., & Knight, S. C. (2009). Mechanisms of action of probiotics: recent advances. Inflammatory bowel diseases, 15(2), 300-310.

Nissle A. On the fundamentals for new causal control of pathological intestinal microflora [Ueber die Grundlagen einer neuen ursaechlichen Bekaempfung der pathologischen Darmflora]. (1961). Deutsche Medizinische Wochenschrift. 1181-1184. Abstract in English (machine translation).

Noguchi, N., Katayama, J., & O'Hara, K. (1996). Cloning and nucleotide sequence of the mphB gene for macrolide 2'-phosphotransferase II in Escherichia coli. FEMS microbiology letters, 144(2-3), 197-202.

Norton, M. D., Spilkia, A. J., & Godoy, V. G. (2013). Antibiotic resistance acquired through a DNA damage-inducible response in Acinetobacter baumannii. Journal of bacteriology, 195(6), 1335-1345.

Novotny, C., Knight, W.S. & Brinton, C.C. (1968). Inhibition of bacterial conjugation by ribonucleic acid and deoxyribonucleic acid male-specific bacteriophages. Journal of bacteriology. 95(2):314-26.

Nunes, R. V., Scherer, C., Pozza, P. C., Eyng, C., Bruno, L. D. G., & Vieites, F. M. (2012). Use of probiotics to replace antibiotics for broilers. Revista Brasileira de Zootecnia, 41(10), 2219-2224.

O'Hara, K., Kanda, T., Ohmiya, K., Ebisu, T. & Kono M. (1989). Purification and characterization of macrolide 2V-phosphotransferase from a strain of Escherichia coli that is highly resistant to erythromycin, Antimicrobial Agents Chemotherapy, 33, 1354 1357.

Olliver, A., Vallé, M., Chaslus-Dancla, E. & Cloeckaert, A. (2004). Role of an acrR mutation in multidrug resistance of in vitro-selected fluoroquinolone-resistant mutants of Salmonella enterica serovar Typhimurium. FEMS Microbiolial Letters, 238, 267-272.

Ondov, B. D., Bergman, N. H., & Phillippy, A. M. (2011). Interactive metagenomic visualization in a Web browser. BMC bioinformatics, 12(1), 1.

Otte, J. M., & Podolsky, D. K. (2004). Functional modulation of enterocytes by gram-positive and gram-negative microorganisms. American Journal of Physiology-Gastrointestinal and Liver Physiology, 286(4), G613-G626.

Ounissi, H., & Courvalin, P. (1985). Nucleotide sequence of the gene ereA encoding the erythromycin esterase in Escherichia coli. Gene, 35(3), 271-278.

Overbeek, R., Olson, R., Pusch, G. D., Olsen, G. J., Davis, J. J., Disz, T., . . . & Vonstein, V. (2014). The SEED and the Rapid Annotation of microbial genomes using Subsystems Technology (RAST). Nucleic acids research, 42(D1), D206-D214.

Pallen, M.J. & Wren, B.W. (2007). Bacterial pathogenomics. Nature, 449(7164):835-42.

Patterson, J. A. & Burkholder, K. M. (2003). Application of prebiotics and probiotics in poultry production. Poultry science, 82(4): 627-631.

Pearson, William R. "[5] Rapid and sensitive sequence comparison with FASTP and FASTA." (1990): 63-98.

Pelicano, E. R. L., De Souza, P. A., De Souza, H. B. A., Leonel, F. R., Zeola, N. M. B. L., & Boiago, M. M. (2004). Productive traits of broiler chickens fed diets containing different growth promoters. Revista Brasileira de Ciência Avícola, 6(3), 177-182.

Perreten, V., & Boerlin, P. (2003). A new sulfonamide resistance gene (sul3) in Escherichia coli is widespread in the pig population of Switzerland.Antimicrobial agents and chemotherapy, 47(3), 1169-1172.

Petri, W. A. J. (2006). Antimicrobial agents: sulfonamides, trimethoprim-sulfamethoxazole, quinolones, and agents for urinary tract infections. In: Brunton, L.L., Lazo, J.S., Parker, chapter 52. 1463-1476.

Poole, K. (2004). Resistance to beta-lactam antibiotics. Cellular and Molecular Life Sciences, 61(17):2200-2223.

Price, L.B., Lackey, L.G., Vailes, R. & Silbergeld, E. (2007). The persistence of fluoroquinolone-resistant Campylobacter in poultry production Environmental[J]. Health Perspectives, 1035-1039.

Rasko, D.A., Moreira, C.G., Li, D.R., Reading, N.C., Ritchie, J.M., Waldor, M.K., Williams, N., Taussig, R., Wei, S., Roth, M. & Hughes, D.T. (2008). Targeting QseC signaling and virulence for antibiotic development. Science. 321(5892):1078-80.

Rea, M. C., Clayton, E., O'Connor, P. M., Shanahan, F., Kiely, B., Ross, R. P., & Hill, C. (2007). Antimicrobial activity of lacticin 3147 against clinical Clostridium difficile strains. Journal of Medical Microbiology, 56(7), 940-946.

Resta-Lenert, S., & Barrett, K. E. (2003). Live probiotics protect intestinal epithelial cells from the effects of infection with enteroinvasive Escherichia coli (EIEC). Gut, 52(7), 988-997.

Roberts, M.C. (2008). Update on macrolide-lincosamide-streptogramin, ketolide, and oxazolidinone resistance genes. FEMS microbiology letters, 282(2):147-59.

Roe, M. T., and S. D. Pillai. (2003). Monitoring and identifying antibiotic resistance mechanisms in bacteria. Poultry Science.82:622-626.

Rolain, J.M. (2013). Food and human gut as reservoirs of transferable antibiotic resistance encoding genes. Frontiers in microbiology, 4:173.

Ross, J. I., Eady, E. A., Cove, J. H., Cunliffe, W. J., Baumberg, S., & Wootton, J. C. (1990). Inducible erythromycin resistance in staphlyococci is encoded by a member of the ATP-binding transport super-gene family. Molecular microbiology, 4(7), 1207-1214.

Salyers, A. A., & Amabile-Cuevas, C. F. (1997). Why are antibiotic resistance genes so resistant to elimination?. Antimicrobial agents and chemotherapy,41(11), 2321.

Sarmah, A.K., Meyer, M.T. & Boxall, A.B. (2006). A global perspective on the use, sales, exposure pathways, occurrence, fate and effects of veterinary antibiotics (VAs) in the environment. Chemosphere. 65(5):725-59.

Schnappinger, D., & Hillen, W. (1996). Tetracyclines: antibiotic action, uptake, and resistance mechanisms. Archives of microbiology, 165(6), 359-369.

Schultz, M., Veltkamp, C., Dieleman, L. A., Grenther, W. B., Wyrick, P. B., Tonkonogy, S. L., & Sartor, R. B. (2002). Lactobacillus plantarum 299V in the treatment and prevention of spontaneous colitis in interleukin-10-deficient mice. Inflammatory bowel diseases, 8(2), 71-80.

(56) References Cited

OTHER PUBLICATIONS

Schwarz, S., Kehrenberg, C., Doublet, B., & Cloeckaert, A. (2004). Molecular basis of bacterial resistance to chloramphenicol and florfenicol. FEMS microbiology reviews, 28(5), 519-542.
Scott, K. P., Gratz, S. W., Sheridan, P. O., Flint, H. J., & Duncan, S. H. (2013). The influence of diet on the gut microbiota. Pharmacological research, 69(1), 52-60.
Sengelov, G., Agersø, Y., Halling-Sørensen, B., Baloda, S. B., Andersen, J. S., & Jensen, L. B. (2003). Bacterial antibiotic resistance levels in Danish farmland as a result of treatment with pig manure slurry. Environment international, 28(7), 587-595.
Shen, J., Zuo, Z. X., & Mao, A. P. (2014). Effect of probiotics on inducing remission and maintaining therapy in ulcerative colitis, Crohn's disease, and pouchitis: meta-analysis of randomized controlled trials. Inflammatory bowel diseases, 20(1), 21-35.
Sherman, P. M., Johnson-Henry, K. C., Yeung, H. P., Ngo, P. S., Goulet, J., & Tompkins, T. A. (2005). Probiotics reduce enterohemorrhagic *Escherichia coli* O157: H7-and enteropathogenic *E. coli* O127: H6-induced changes in polarized T84 epithelial cell monolayers by reducing bacterial adhesion and cytoskeletal rearrangements. Infection and immunity, 73(8), 5183-5188.
Shoemaker, N. B., Vlamakis, H., Hayes, K., & Salyers, A. A. (2001). Evidence for Extensive Resistance Gene Transfer among*Bacteroides* spp. and among *Bacteroides* and Other Genera in the Human Colon. Applied and environmental microbiology, 67(2), 561-568.
Shore, A. C., Deasy, E. C., Slickers, P., Brennan, G., O'Connell, B., Monecke, S., . . . & Coleman, D. C. (2011). Detection of staphylococcal cassette chromosome mec type XI carrying highly divergent mecA, mecI, mecR1, blaZ, and ccr genes in human clinical isolates of clonal complex 130 methicillin-resistant *Staphylococcus aureus*. Antimicrobial agents and chemotherapy, 55(8), 3765-3773.
Silver, L. L. (2011). Challenges of antibacterial discovery. Clinical microbiology Yeviews, 24(1), 71-109.
Singh, P., Karimi, A., Devendra, K., Waldroup, P. W., Cho, K. K., & Kwon, Y. M. (2013). Influence of penicillin on microbial diversity of the cecal microbiota in broiler chickens. Poultry science, 92(1), 272-276.
Skold, O. (2000). Sulfonamide resistance: mechanisms and trends. Drug Resistance Updates, 3(3), 155-160.
Sköld, O. (2001). Resistance to trimethoprim and sulfonamides. Veterinary research.32(3-4):261-73.
Smillie, C., Garcillán-Barcia, M.P., Francia, M.V., Rocha, E.P., & de la Cruz, F. (2010). Mobility of plasmids. Microbiology and Molecular Biology Reviews, 74(3):434-52.
Smith, D. L., Dushoff, J., Perencevich, E. N., Harris, A. D., & Levin, S. A. (2004). Persistent colonization and the spread of antibiotic resistance in nosocomial pathogens: resistance is a regional problem. Proceedings of the National Academy of Sciences of the United States of America, 101(10), 3709-3714.
Smith, D. L., Levin, S. A., & Laxminarayan, R. (2005). Strategic interactions in multi-institutional epidemics of antibiotic resistance. Proceedings of the National Academy of Sciences of the United States of America, 102(8), 3153-3158.
Smith, H. W. (1970). The transfer of antibiotic resistance between strains of enterobacteria in chicken, calves and pigs. Journal of medical microbiology, 3(1): 165-180.
Sommer, F. & Bäckhed, F. (2013). The gut microbiota—masters of host development and physiology. Nature Reviews Microbiology, 11(4): 227-238.
Starr, M. P., & Reynolds, D. M. (1951). Streptomycin resistance of coliform bacteria from turkeys fed streptomycin. American Journal of Public Health and the Nations Health, 41(11_Pt_1), 1375-1380.
Sullivan, Å., Johansson, A., Svenungsson, B., & Nord, C. E. (2004). Effect of Lactobacillus F19 on the emergence of antibiotic-resistant microorganisms in the intestinal microflora. Journal of Antimicrobial Chemotherapy, 54(4), 791-797.
Sundqvist, M., Geli, P., Andersson, D.I., Sjölund-Karlsson, M., Runehagen, A., Cars, H., Abelson-Storby, K., Cars, O. & Kahlmeter, G. (2010). Little evidence for reversibility of trimethoprim resistance after a drastic reduction in trimethoprim use. Journal of antimicrobial chemotherapy. 65(2):350-60.
Tamber, S., & Hancock, R. E. (2003). On the mechanism of solute uptake in Pseudomonas. Frontiers in bioscience: a journal and virtual library, 8, s472-83.
Tängdén, T., Adler, M., Cars, O., Sandegren, L., & Löwdin, E. (2013). Frequent emergence of porin-deficient subpopulations with reduced carbapenem susceptibility in ESBL-producing *Escherichia coli* during exposure to ertapenem in an in vitro pharmacokinetic model. Journal of Antimicrobial Chemotherapy, dkt044.
Tannock, G. W., Tiong, S., Priest, P., Munro, K., Taylor, C., Richardson, A., & Schultz, M. (2011). Testing probiotic strain *Escherichia coli* Nissle 1917 (Mutaflor) for its ability to reduce carriage of multidrug-resistant *E. coli* by elderly residents in long-term care facilities. Journal of medical microbiology,60(3), 366-370.
Ten Bruggencate, S. J. M., Girard, S. A., Floris-Vollenbroek, E. G. M., Bhardwaj, R., & Tompkins, T. A. (2015). The effect of a multi-strain probiotic on the resistance toward *Escherichia coli* challenge in a randomized, placebo-controlled, double-blind intervention study. European journal of clinical nutrition, 69(3), 385-391.
Tenson, T., Lovmar, M., & Ehrenberg, M. (2003). The mechanism of action of macrolides, lincosamides and streptogramin B reveals the nascent peptide exit path in the ribosome. Journal of molecular biology, 330(5), 1005-1014.
Threlfall, E. J., Ward, L. R., Frost, J. A., & Willshaw, G. A. (2000). The emergence and spread of antibiotic resistance in food-borne bacteria.International journal of food microbiology, 62(1), 1-5.
Torok, V. A., Allison, G. E., Percy, N. J., Ophel-Keller, K., & Hughes, R. J. (2011). Influence of antimicrobial feed additives on broiler commensal posthatch gut microbiota development and performance. Applied and environmental microbiology, 77(10), 3380-3390.
Trebichavsky, I., Splichal, I., Rada, V. & Splichalova, A. (2010). Modulation of natural immunity in the gut by *Escherichia coli* strain Nissle 1917. Nutrition reviews, 68(8):459-64.
Tsafnat, G., Copty, J., & Partridge, S. R. (2011). RAC: repository of antibiotic resistance cassettes. Database, 2011, bar054. http://rac.aihi.mq.edu.au/rac/ Accessed in Jul. 2016.
Tu, D., G. Blaha, P.B. Moore & T.A. Steitz. (2005). Structures of MLSBK antibiotics bound to mutated large ribosomal subunits provide a structural explanation for resistance. Cell , 121: 257-270.
Tuomola, E. M., Ouwehand, A. C., & Salminen, S. J. (1999). The effect of probiotic bacteria on the adhesion of pathogens to human intestinal mucus.FEMS Immunology & Medical Microbiology, 26(2), 137-142.
Turner, J. (2000): Factory farming and the environment. Scn News United Nations System's Forum on Nutrition, vol. 21.
U.S. Census Bureau. (2011). Broiler and Turkey Production by State: 2008 to 2010. https://www.census.gov/compendia/statab/2012/tables/12s0878.pdf. Accessed Jul. 2016.
U.S. Food and Drug Administration (2010). Draft guidance #209. Available at http://www.fda.gov/downloads/animalveterinary/guidancecomplianceenforcement/guidanceforindustry/ucm216936.pdf. Accessed Jul. 2016.
U.S. Food and Drug Administration (2012). Antibacterial Drug Usage Analysis—U.S. Food and Drug Administration. https://search.usa.gov/search?utf8=%E2%9C%93&affiliate=fda&sort_by=&query=UCM319435, Accessed Jul. 2016.
U.S. Food and Drug Administration, and Center for Veterinary Medicine. (2013). Draft guidance #213. Available at https://www.fda.gov/media/83488/download.
U.S. Food and Drug Administration, and Center for Veterinary Medicine. (2013). Proposed rule: Veterinary Feed Directive. Available at https://www.federalregister.gov/articles/2013/12/12/2013-29696/veterinary-feed-directive. Accessed Jul. 2016.
U.S. Food and Drug administration. (2013). 2011 Summary Report on Antimicrobials Sold or Distributed for Use in Food-Producing Animals. http://www.fda.gov/downloads/ForIndustry/UserFees/AnimalDrugUserFeeActADUFA/UCM338170.pdfAccessedJul. 2016.
U.S. Food and Drug administration. (2014).2012 Summary Report on Antimicrobials Sold or Distributed for Use in Food-Producing

(56) References Cited

OTHER PUBLICATIONS

Animals. http://www.fda.gov/downloads/ForIndustry/UserFees/AnimalDrugUserFeeActADUFA/UCM416983.pdf. Accessed Jul. 2016.
U.S. Food and Drug administration. (2015). 2013 Summary Report on Antimicrobials Sold or Distributed for Use in Food-Producing Animals. http://www.fda.gov/downloads/ForIndustry/UserFees/AnimalDrugUserFeeActADUFA/UCM440584.pdf. Accessed Jul. 2016.
U.S. Food and Drug administration. (2015). 2014 Summary Report on Antimicrobials Sold or Distributed for Use in Food-Producing Animals. http://www.fda.gov/downloads/ForIndustry/UserFees/AnimalDrugUserFeeActADUFA/UCM476258.pdf. Accessed Jul. 2016.
Unemo, M., Golparian, D., Nicholas, R., Ohnishi, M., Gallay, A., & Sednaoui, P. (2012). High-level cefixime-and ceftriaxone-resistant Neisseria gonorrhoeae in France: novel penA mosaic allele in a successful international clone causes treatment failure. Antimicrobial agents and chemotherapy,56(3), 1273-1280.
Vaden, S.L. & Riviere, J.E. (2001) Penicillins and related beta-lactam antibiotics. In Veterinary Pharmacology and Therapeutics. Ed. Adams, H.R., pp. 818-827. Iowa State University Press, Ames, IA.
Van Boeckel, T. P., Brower, C., Gilbert, M., Grenfell, B. T., Levin, S. A., Robinson, T. P., & Laxminarayan, R. (2015). Global trends in antimicrobial use in food animals. Proceedings of the National Academy of Sciences,112(18), 5649-5654.
Van den Bogaard, A. E., London, N., Driessen, C., & Stobberingh, E. E. (2001). Antibiotic resistance of faecal *Escherichia coli* in poultry, poultry farmers and poultry slaughterers. Journal of Antimicrobial Chemotherapy, 47(6), 763-771.
Van den Bogaard, A.E., Bruinsma, N. and Stobberingh, E.E., (2000). The effect of banning avoparcin on VRE carriage in the Netherlands. Journal of Antimicrobial Chemotherapy, 46(1), pp. 146-148.
Van Leeuwen, F.X.R. (1991) In Toxicological evaluation of certain veterinary drug residues in food. 29 The Joint FAO/WHO Expert Committee on Food Additive☐.
Van, T.T., Chin, J., Chapman, T., Tran, L.T. & Coloe, P.J. (2008). Safety of raw meat and shellfish in Vietnam: an analysis of *Escherichia coli* isolations for antibiotic resistance and virulence genes. International journal of food microbiology, 124(3):217-23.
Vaughan, R. B. (1965). The romantic rationalist: A study of Elie Metchnikoff. Medical history, 1;9(3):201-15.
Vetting, M. W., Hegde, S. S., Wang, M., Jacoby, G. A., Hooper, D. C., & Blanchard, J. S. (2011). Structure of QnrB1, a plasmid-mediated fluoroquinolone resistance factor. Journal of Biological Chemistry, 286(28), 25265-25273.
Videnska, P., Faldynova, M., Juricova, H., Babak, V., Sisak, F., Havlickova, H., & Rychlik, I. (2013). Chicken faecal microbiota and disturbances induced by single or repeated therapy with tetracycline and streptomycin. BMC veterinary research, 9(1), 1.
Vogelman, B., Craig, W.A. (1986). Kinetics of antimicrobial activity. The Journal of pediatrics, 108(5):835-40.
Voulgari, E., Poulou, A., Koumaki, V. & Tsakris, A. (2013). Carbapenemase-producing Enterobacteriaceae: now that the storm is finally here, how will timely detection help us fight back? Future Microbiology, 8, 27-39.
Vuotto, C., Longo, F., & Donelli, G. (2014). Probiotics to counteract biofilm-associated infections: promising and conflicting data. International journal of oral science, 6(4), 189-194.
Wang, H. H., Manuzon, M., Lehman, M., Wan, K., Luo, H., Wittum, T. E., . . . & Bakaletz, L. O. (2006). Food commensal microbes as a potentially important avenue in transmitting antibiotic resistance genes. FEMS Microbiology Letters, 254(2), 226-231.
Wang, H.H. (2009). Commensal bacteria, microbial ecosystems and horizontal gene transmission: adjusting our focus for strategic breakthroughs against antibiotic resistance. In Foodborne Microbes: Shaping the Host Ecosystems (Jaykus L, Wang HH, Schlesinger L., eds). p. 267-281. ASM Press.

Waters, A. E., Contente-Cuomo, T., Buchhagen, J., Liu, C. M., Watson, L., Pearce, K., . . . & Keim, P. S. (2011). Multidrug-resistant *Staphylococcus aureus* in US meat and poultry. Clinical Infectious Diseases, 52(10), 1227-1230.
Waxman, D. J., & Strominger, J. L. (1983). Penicillin-binding proteins and the mechanism of action of beta-lactam antibiotics1. Annual review of biochemistry, 52(1), 825-869.
Webber, M. A., Talukder, A., & Piddock, L. J. (2005). Contribution of mutation at amino acid 45 of AcrR to acrB expression and ciprofloxacin resistance in clinical and veterinary *Escherichia coli* isolates. Antimicrobial agents and chemotherapy, 49(10), 4390-4392.
Wegener, H.C., Aarestrup, F.M., Jensen, L.B., Hammerum, A.M. & Bager, F. (1999). Use of antimicrobial growth promoters in food animals and Enterococcus faecium resistance to therapeutic antimicrobial drugs in Europe. Emerging infectious diseases, 5(3):329.
Wei, S., Morrison, M., & Yu, Z. (2013). Bacterial census of poultry intestinal microbiome. Poultry science, 92(3): 671-683.
Williams, C.M., Barker, J.C. & Sims, J.T. (1999). Management and utilization of poultry wastes; Tables 2, 3, 4, 5, 6 and 7. Rev. Environ. Contam. Toxicol., 162: 105-157.
Wise, R. (2007). An overview of the Specialist Advisory Committee on Antimicrobial Resistance (SACAR). Journal of Antimicrobial Chemotherapy,60(suppl 1), i5-i7.
World Health Organization (WHO). (2014). Antimicrobial resistance: global report on surveillance 2014.
World Health Organization. (1997). The medical impact of the use of antimicrobials in food animals: Report of a WHO meeting, Berlin, Germany. http://whqlibdoc.who.int/hq/1997/WHO_EMC_ZOO_97.4.pdf Accessed Jul. 2016.
Wright, G. D. (2005). Bacterial resistance to antibiotics: enzymatic degradation and modification. Advanced Drug Delivery Reviews, 57, 1451-1470.
Yamamoto, T., Watanabe, M., Matsumoto, K., & Sawai, T. (1983). Tn2610, a transposon involved in the spread of the carbenicillin-hydrolyzing β-lactamase gene. Molecular and General Genetics MGG, 189(2), 282-288.
Yu, Z., and M. Morrison. 2004. Improved extraction of PCR-quality community DNA from digesta and fecal samples[J]. BioTechniques. 36:808-812.
Zhang, J., and T. L. Madden. "PowerBlast: A network application for automated analysis of large genomic sequences." Genome Res 7 (1997): 649-656.
Zhang, L., Huang, Y., Zhou, Y., Buckley, T., & Wang, H. H. (2013). Antibiotic administration routes significantly influence the levels of antibiotic resistance in gut microbiota. Antimicrobial agents and chemotherapy, 57(8), 3659-3666.
Zhang, L., Kinkelaar, D., Huang, Y., Li, Y., Li, X., & Wang, H. H. (2011). Acquired antibiotic resistance: are we born with it? Applied and environmental microbiology, 77(20), 7134-7141.
Zhang, Q., Lambert, G., Liao, D., Kim, H., Robin, K., Tung, C. K., . . . & Austin, R. H. (2011). Acceleration of emergence of bacterial antibiotic resistance in connected microenvironments. Science, 333(6050), 1764-1767.
Zhao, S., White, D. G., McDermott, P. F., Friedman, S., English, L., Ayers, S., . . . & Walker, R. D. (2001). Identification and Expression of Cephamycinasebla CMY Genes in *Escherichia coli* and *Salmonella* Isolates from Food Animals and Ground Meat. Antimicrobial agents and chemotherapy, 45(12), 3647-3650.
Zhou, W., Wang, Y. & Lin, J. (2012). Functional cloning and characterization of antibiotic resistance genes from the chicken gut microbiome. Applied and environmental microbiology, 78(8):3028-32.
Ziv, G., Neumann, J., Fridman, J., Ziv, E., Singer, N., & Meshorer, A. (1979). Effects of probenecid on blood levels and tissue distribution of ampicillin in fowls and turk eys. Avian diseases, 927-939.
Zoetendal, E.G., Cheng, B., Koike, S. & Mackie R.I. (2004). Molecular microbial ecology of the gastrointestinal tract: from phylogeny to function[J]. Current issues in intestinal microbiology, 5(2): 31-48.
Zyrek, A. A., Cichon, C., Helms, S., Enders, C., Sonnenborn, U., & Schmidt, M. A. (2007). Molecular mechanisms underlying the probiotic effects of *Escherichia coli* Nissle 1917 involve ZO-2 and

(56) References Cited

OTHER PUBLICATIONS

PKCζ redistribution resulting in tight junction and epithelial barrier repair. Cellular microbiology, 9(3), 804-816.

\* cited by examiner

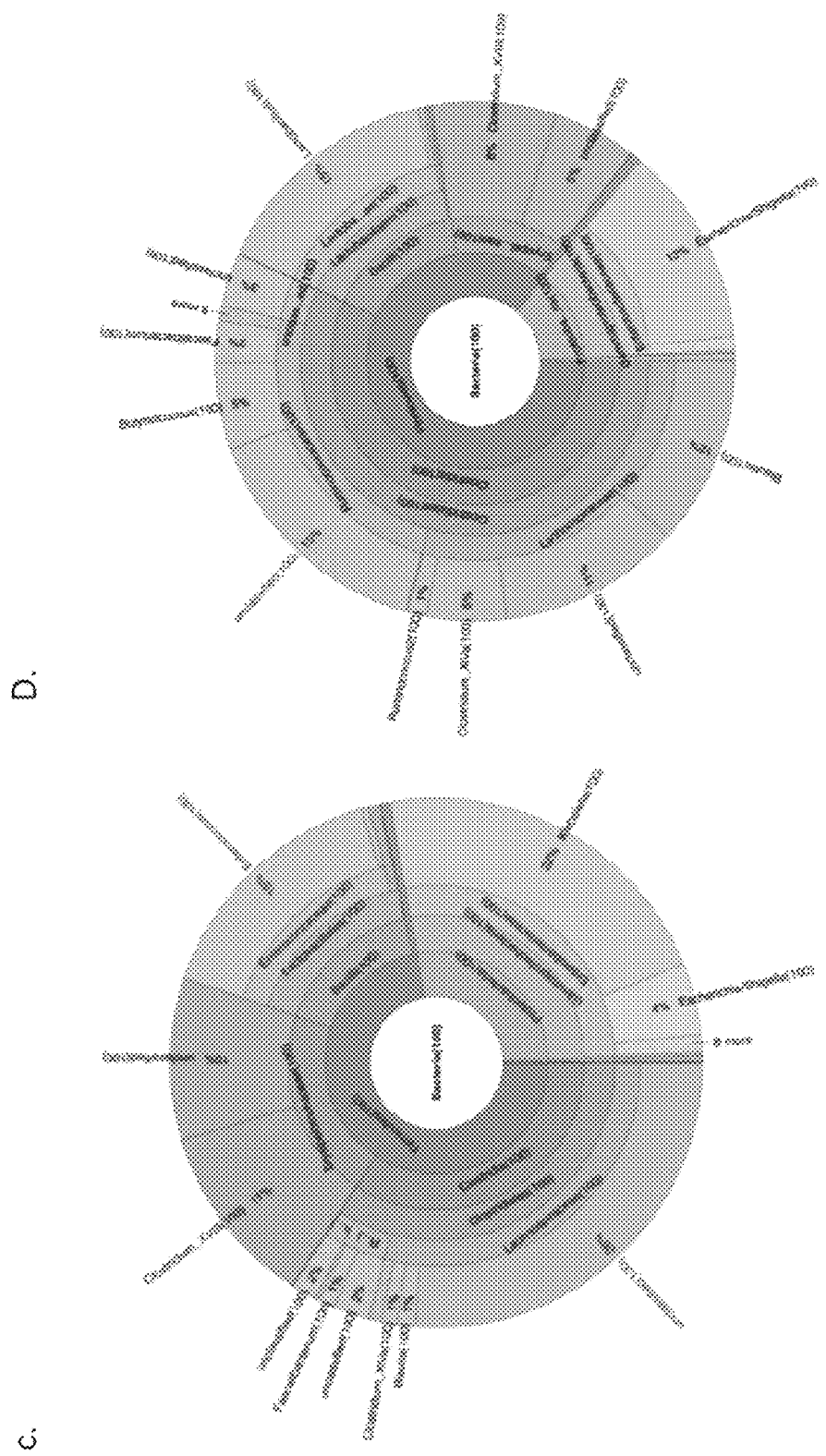
FIGURE 7C-D

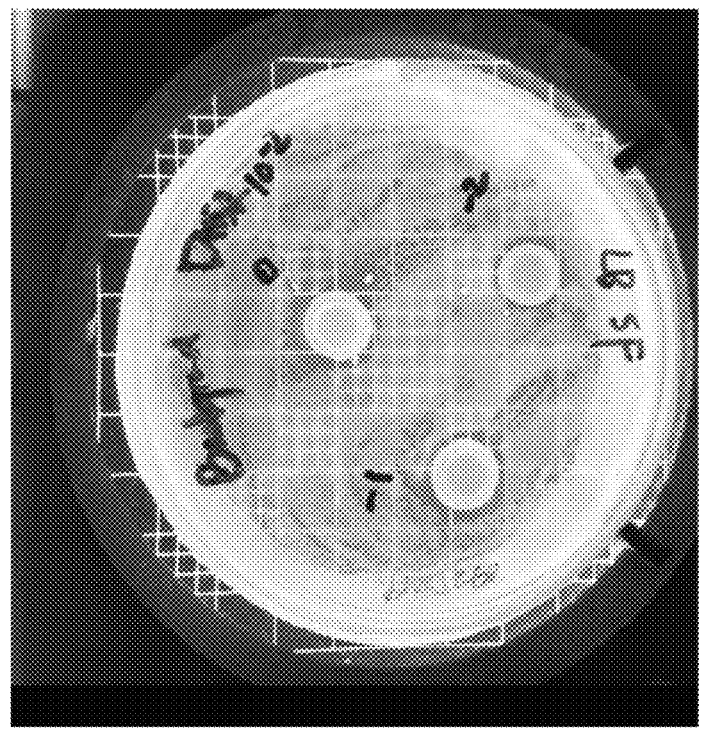
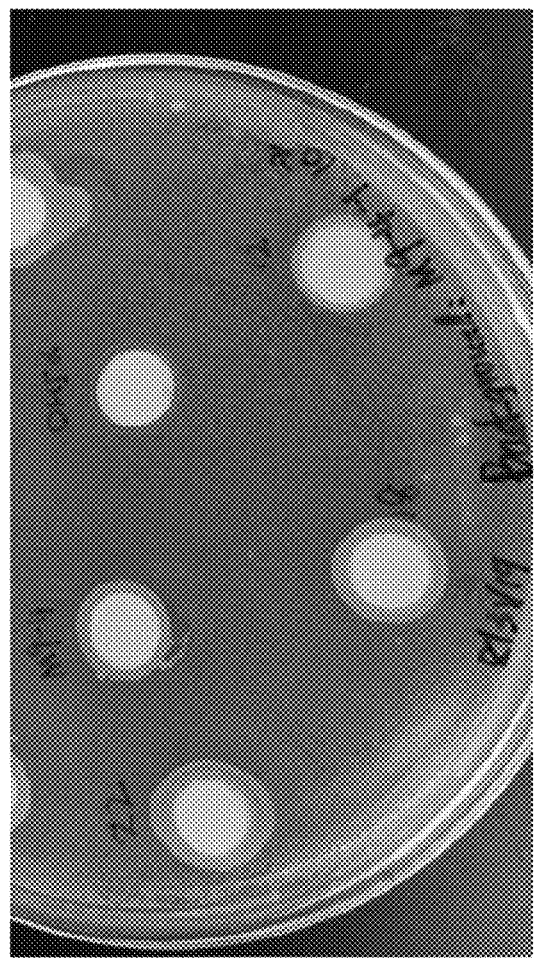
FIGURE 8A-B

METHODS AND COMPOSITIONS TO MODULATE ANTIBIOTIC RESISTANCE AND GASTROINTESTINAL MICROBIOTA

CROSS-REFERENCE TO RELATED APPLICATIONS

This application claims benefit of U.S. Provisional Application No. 62/729,031, filed Sep. 10, 2018, both of which are hereby incorporated herein by reference in their entirety.

STATEMENT REGARDING FEDERALLY SPONSORED RESEARCH

This invention was made with government support under Grant No. 31-6025986 awarded by the US-UK Global Innovation Initiative through the U.S. Department of State. The Government has certain rights in the invention.

FIELD

The disclosure generally relates to the uses of bacterial strain isolates, and to improving the quality of intestinal microbiota and reducing the amount of antibiotic resistant bacteria therein.

BACKGROUND

The impact of antibiotics on the gastrointestinal (GI) tract is complicated partially due to the complexity of GI microbiota and the lack of appropriate markers to monitor. While pathogens have been the focus of antibiotic resistance studies for decades, pathogenic bacteria in particular constitute a very small percentage in GI microbiota (Laxminarayan et al., 2013). Targeting certain groups of commensal bacteria and tracking their dynamics during antibiotic treatment is a more promising strategy to explore antibiotic-GI tract interactions.

The rapid emergence and dissemination of antibiotic resistance (AR) is a critical threat to public health. Unnecessary use of antibiotics should be limited, particularly antibiotic growth-promoters in food-producing animal farming. Probiotics are an alternative to antibiotic use. The antimicrobial and microbiota-modulation activity of probiotics can hinder colonization of pathogenic bacteria, improve overall gut health, and potentially reduce the applied dosage of antibiotic (Vuotto et al., 2014). While the mainstream probiotics are primarily intended to modulate gut microbiota for controlling infections by pathogens and growth promotion, certain probiotic strains are also able to reduce the colonization of ART bacteria. For example, probiotic *E. coli* Nissle 1917 was observed to prevent the colonization of multidrug-resistant *E. coli* in human gut (Tannock et al., 2011). Other observed AR reduction activities include increasing strain susceptibility, inhibiting resistant gene transfer and performing antagonistic activity against AR strains (Moubareck et al., 2007; Ditu et al., 2011; Naderi et al., 2014). However, the mechanisms of mitigating AR by probiotics are not fully understood.

During early development of chickens hatched in a teaching farm, ampicillin resistance encoded by the $bla_{CMY-2}$ gene has low abundance. However, the composition of GI microbiota is dynamic, affected not only by antibiotics but also by microorganisms ingested through oral routes (such as food, feed, water, etc.), as well as other host factors. Since antibiotic resistant (AR) bacteria are found in poultry gut microbiota with or without direct exposure to antibiotics, the large quantity of feces containing AR bacteria from poultry production represents an important contamination source impacting the environmental AR gene pool. Thus, targeted strategies to minimize the prevalence of AR in food-producing animal GI microbiota are essential for effective mitigation of AR in the poultry production system.

Probiotic development can include identifying novel probiotic candidates from commensal bacteria in gut microbiota, which may have better colonization capabilities and individual-specific benefits (Hill et al., 2014). The GI microbiota, including the pool of AR bacteria (sometimes referred to as resistome), are established at very early stage of life, which may be a desirable stage for effective probiotic intervention.

The compositions and methods disclosed herein address these and other needs.

SUMMARY

Disclosed herein is a feed composition comprising *Lactobacillus crispatus* WZ-12 or a derivative thereof and an ingestible food product; wherein the composition comprises *Lactobacillus crispatus* WZ-12 or a derivative thereof in an amount sufficient for use as a probiotic treatment of a subject. Also disclosed is a pharmaceutical composition and an ingestible food product comprising the compositions disclosed herein.

Further disclosed is a method of modulating gut microbiota in a subject comprising administering a composition comprising *Lactobacillus crispatus* WZ-12 or a derivative thereof to the subject.

Disclosed herein is a bacterial strain comprising a *Lactobacillus crispatus* WZ-12, *Lactobacillus salivarius* 1-14, or *Lactobacillus reuteri* 2-2 derivative engineered to comprise a derivative genome which differs from a parental genome of the parental strain by at least one nucleotide, and which improves one or more probiotic qualities of the engineered bacterial strain compared to the parental strain.

Additional aspects and advantages of the disclosure will be set forth, in part, in the detailed description and any claims which follow, and in part will be derived from the detailed description or can be learned by practice of the various aspects of the disclosure. The advantages described below will be realized and attained by means of the elements and combinations particularly pointed out in the appended claims. It is to be understood that both the foregoing general description and the following detailed description are exemplary and explanatory only and are not restrictive of the disclosure.

BRIEF DESCRIPTION OF THE DRAWINGS

The accompanying drawings, which are incorporated in and constitute a part of this specification, illustrate certain examples of the present disclosure and together with the description, serve to explain, without limitation, the principles of the disclosure. Like numbers represent the same element(s) throughout the figures.

FIG. 5A) Phylum level; FIG. 5B) Class level. The treatments include Lane 1 (no, cocktail, no): no ESBL *E. coli* inoculation for 4 days, then inoculated with probiotic cocktail but no Tween 80; Lane 2 (no; no, no): no *E. coli*, no probiotics, no Tween 80; Lane 3: (probiotics, *E. coli*, no): probiotic cocktail for 4 days, followed by *E. coli*, but no Tween 80); Lane 4 (Yes, CG12, no): *E. coli* for 4 days, followed by *Lb. crispatus* (WZ12) for 4 days but no Tween 80; Lane 5 (yes, cocktail, no): *E. coli* for 4 days, followed by probiotic cocktail for 4 days, no Tween; Lane 6 ((yes, cocktail, yes): *E. coli* for 4 days, followed by probiotic cocktail for 4 days, with Tween 80; Lane 7 (Yes, no, no): *E. coli* for 4 days, saline for 4 days (no probiotics no Tween); Lane 8 (yes, no, yes): ESBL *E. coli* for 4 days, no probiotics but with Tween 80 for 4 days.

FIG. 6A) Phylum level; FIG. 6B) Class level. Group 1: probiotic cocktail treatment throughout, *E. coli* exposure from Day 5 for 4 days and then oral Amp; Group 2: probiotic/peanut butter treatment throughout followed by *E. coli* exposure and then oral Amp; Group 3: inoculated (*E coli*) then exposed to oral Amp, Group 4: noninoculated then exposed to oral Amp, Group 5: noninoculated then exposed to injective Amp, Group 6: noninoculated then exposed to saline; Group 7: inoculated (*E coli*) then exposed to injective Amp.

FIG. 7A-E shows a krona chart of the composition of fecal microbiota on Day 25 in pooled samples. (A) NI-Saline-PO; (B) NI-Amp-IM; (C) NI-Amp-PO; (D) Amp-IM; (E) Amp-PO.

FIG. 8A-B shows growth inhibition tests. A). The "bully" *E. coli* of 0, 10-1, 10-2 dilutions inoculated on the LB plate covered with DH5α. B). Multiple DH5α derivatives M9-4-1 are no longer inhibited (clear inhibition zone) by the "bully" strain M9-4 but with white growth ring.

DETAILED DESCRIPTION

Figure 1:
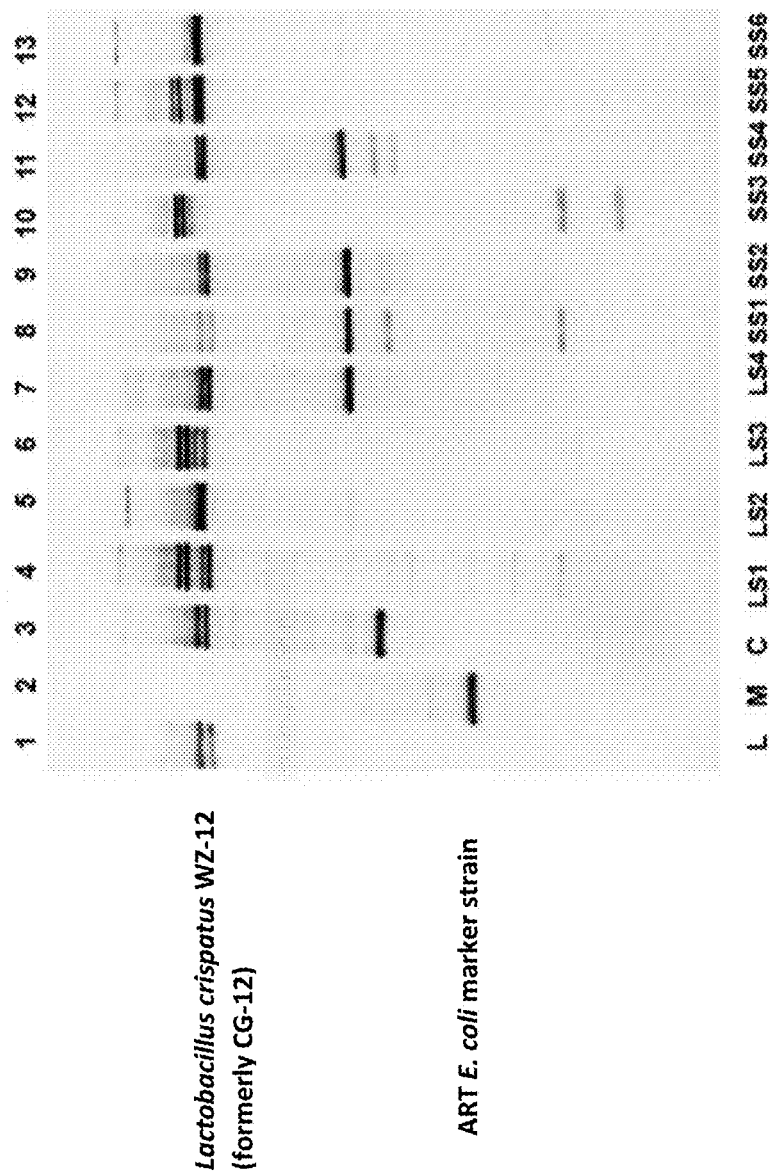
FIG. 1 is an image showing predominant 16S rRNA genes in total fecal DNA from chicken after 3 days of inoculation with *Lactobacillus crispatus* WZ-12 (alternatively referred to herein as *Lactobacillus crispatus* CG-12). Lane 1: *Lactobacillus crispatus* WZ-12; Lane 2: $bla_{CMY-2}$+*E. coli* marker strain; Lane 3: sample from control group; Lane 4-7: 4 individual samples from Lc-Saline group; Lane 8-13: 6 individual samples from Saline-Saline group.

The following description of the disclosure is provided as an enabling teaching of the disclosure in its best, currently known embodiment(s). To this end, those skilled in the relevant art will recognize and appreciate that many changes can be made to the various embodiments of the invention described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

Terminology

Unless defined otherwise, all technical and scientific terms used herein have the same meaning as commonly understood to one of ordinary skill in the art to which this invention belongs. The following definitions are provided for the full understanding of terms used in this specification.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular bacterial strain is disclosed and discussed and a number of modifications that can be made to the bacterial strain are discussed, specifically contemplated is each and every combination and permutation of the bacterial strain and the modifications that are possible unless specifically indicated to the contrary. Thus, if a class of bacterial strains A, B, and C are disclosed as well as a class of bacterial strains D, E, and F and an example of a combination of bacterial strains, or, for example, a combination of bacterial strains comprising A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

It is understood that the compositions disclosed herein have certain functions. Disclosed herein are certain structural requirements for performing the disclosed functions, and it is understood that there are a variety of structures which can perform the same function which are related to the disclosed structures, and that these structures will ultimately achieve the same result.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

As used in the specification and claims, the singular form "a," "an," and "the" include plural references unless the context clearly dictates otherwise. For example, the term "an agent" includes a plurality of agents, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

As utilized herein, "probiotic" refers to microorganisms that form at least a part of the transient or endogenous flora and thereby exhibit a beneficial prophylactic and/or therapeutic effect on the host organism. Probiotics are generally known to be clinically safe (i.e., non-pathogenic) by those individuals skilled in the art.

The term "probiotic composition" refers to a composition comprising a probiotic bacterium in a pharmaceutically or nutraceutically acceptable carrier that allows high cell viability after oral administration. For example, in some cases, the probiotic bacterium is lyophilized. In some cases, the probiotic bacterium is encapsulated in a gel matrix.

The term "probiotic bacterium" denotes a natural or recombinant bacterium which ingested live in adequate quantities can exert beneficial effects on the human health. They are now widely used as a food additive for their health-promoting effects. Health benefits are a result of, for example, production of nutrients and/or co-factors by the probiotic, competition of the probiotic with pathogens and/or stimulation of an immune response in the subject by the probiotic.

The term "intestinal diseases," as used herein, is intended to refer to bacterial infectious or inflammatory diseases in the intestine. Examples of the intestinal diseases include, but are not limited to, infectious diarrhea caused by pathogenic microorganisms (*E. coli, salmonella*, and *clostridium*), gastroenteritis, inflammatory bowel diseases, psychogenic enteritis syndrome, overgrowth of microorganisms in the small intestine, and the like.

As used herein, the terms "pathogen" and "parasite" are used interchangeably in the context of a deleterious organism growing in the gastrointestinal tract and/or feces of an animal, although it appreciated that these terms have distinctive meanings.

The term "encapsulate" refers to the coating of a probiotic or a plurality of probiotics in a composition. In one example, the probiotic is encapsulated in a composition that protects the probiotic from gastric conditions and, for example, that releases the probiotic in the intestine, such as the small intestine, of a subject.

The term "nutraceutically acceptable" refers to those compounds, materials, compositions, and/or dosage forms which are compatible with the other ingredients of the formulation and suitable for ingestion by mammals, such as humans.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "prevent" refers to a treatment that forestalls or slows the onset of a disease or condition or reduces the severity of the disease or condition. Thus, if a treatment can treat a disease in a subject having symptoms of the disease, it can also prevent that disease in a subject who has yet to suffer some or all of the symptoms.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician. The subject can be livestock, such as pigs, cows, goats, or poultry.

The term "therapeutically effective" refers to the amount of the composition used is of sufficient quantity to ameliorate one or more causes or symptoms of a disease or disorder. Such amelioration only requires a reduction or alteration, not necessarily elimination.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "probiotic bacterium" denotes a bacterium which ingested live in adequate quantities can exert beneficial effects on the human health.

By "normal gut flora" is meant a population of microbes that is substantially similar to the population of microbes present in the gut of a healthy control subject.

By "ameliorate" is meant decrease, suppress, attenuate, diminish, arrest, or stabilize the development or progression of a disease.

The term "comprising" as used herein is synonymous with "including" or "containing," and is inclusive or open-ended and does not exclude additional, unrecited members, elements or method steps.

As used herein, the term "in vivo" refers to events that occur within an organism (e.g., animal, plant, or microbe).

As used herein, the term "isolated" refers to a substance or entity that has been (1) separated from at least some of the components with which it was associated when initially produced (whether in nature or in an experimental setting), and/or (2) produced, prepared, and/or manufactured by the hand of man. Isolated substances and/or entities may be separated from at least about 10%, about 20%, about 30%>, about 40%>, about 50%>, about 60%), about 70%, about 80%>, about 90%>, or more of the other components with which they were initially associated. In some embodiments, isolated agents are more than about 80%, about 85%, about 90%, about 91%, about 92%, about 93%, about 94%, about 95%, about 96%), about 97%), about 98%>, about 99%, or more than about 99% pure. As used herein, a substance is "pure" if it is substantially free of other components.

The term "isolated bacterium" or "isolated polypeptide" is a polypeptide or bacteria that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or bacteria may also be rendered substantially free of naturally associated components by isolation, using protein purification techniques well known in the art.

As used herein, a "modified derivative" refers to polypeptides or fragments thereof that are substantially homologous in primary structural sequence to a reference polypeptide sequence but which include, e.g., in vivo or in vitro chemical and biochemical modifications or which incorporate amino acids that are not found in the reference polypeptide. Such modifications include, for example, acetylation, carboxylation, phosphorylation, glycosylation, ubiquitination, labeling, e.g., with radionuclides, and various enzymatic modifications, as will be readily appreciated by those skilled in the art. A variety of methods for labeling polypeptides and of substituents or labels useful for such purposes are well known in the art, and include radioactive isotopes such as I, P, S, and H, ligands that bind to labeled antiligands (e.g., antibodies), fluorophores, chemiluminescent agents, enzymes, and antiligands that can serve as specific binding pair members for a labeled ligand. The choice of label depends on the sensitivity required, ease of conjugation with the primer, stability requirements, and available instrumentation. Methods for labeling polypeptides are well known in the art. See, e.g., Ausubel et al, Current Protocols in Molecular Biology, Greene Publishing Associates (1992, and Supplements to 2002).

As used herein, "polypeptide mutant" or "mutein" refers to a polypeptide whose sequence contains an insertion, duplication, deletion, rearrangement or substitution of one or more amino acids compared to the amino acid sequence of a reference protein or polypeptide, such as a native or wild-type protein. A mutein may have one or more amino acid point substitutions, in which a single amino acid at a position has been changed to another amino acid, one or more insertions and/or deletions, in which one or more amino acids are inserted or deleted, respectively, in the sequence of the reference protein, and/or truncations of the amino acid sequence at either or both the amino or carboxy termini. A mutein may have the same or a different biological activity compared to the reference protein.

In some embodiments, a mutein has, for example, at least 85% overall sequence homology to its counterpart reference protein. In some embodiments, a mutein has at least 90% overall sequence homology to the wild-type protein. In other embodiments, a mutein exhibits at least 95% sequence identity, or 98%, or 99%, or 99.5% or 99.9% overall sequence identity.

The term "polynucleotide", "nucleic acid molecule", "nucleic acid", or "nucleic acid sequence" refers to a polymeric form of nucleotides of at least 10 bases in length. The term includes DNA molecules (e.g., cDNA or genomic or synthetic DNA) and RA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation.

A "synthetic" RNA, DNA or a mixed polymer is one created outside of a cell, for example one synthesized chemically.

As used herein, an endogenous nucleic acid sequence in the genome of an organism (or the encoded protein product of that sequence) is deemed "recombinant" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "recombinant" because it is separated from at least some of the sequences that naturally flank it.

A nucleic acid is also considered "recombinant" if it contains any modifications that do not naturally occur to the corresponding nucleic acid in a genome. For instance, an endogenous coding sequence is considered "recombinant" if it contains an insertion, deletion or a point mutation introduced artificially, e.g., by human intervention.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence. The term "degenerate oligonucleotide" or "degenerate primer" is used to signify an oligonucleotide capable of hybridizing with target nucleic acid sequences that are not necessarily identical in sequence but that are homologous to one another within one or more particular segments.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32, and even more typically at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, Methods Enzymol. 183:63-98 (1990). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., J. Mol. Biol. 215:403-410 (1990); Gish and States, Nature Genet. 3:266-272 (1993); Madden et al, Meth. Enzymol. 266: 131-141 (1996); Altschul et al, Nucleic Acids Res. 25:3389-3402 (1997); Zhang and Madden, Genome Res. 7:649-656 (1997)), especially blastp or tblastn (Altschul et al, Nucleic Acids Res. 25:3389-3402 (1997)).

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 76%, 80%>, 85%, or at least about 90%>, or at least about 95%, 96%, 97%, 98% or 99% of the nucleotide bases, as measured by any well-known algorithm of sequence identity, such as FASTA, BLAST or Gap, as discussed above.

Compositions

Antibiotic resistance is a major challenge to human health worldwide. The broad use of antibiotic resistance is considered the reason that led to the problem seen today. But innovative research discovered multiple key risk factors. Targeted mitigation of all is essential to achieve effective control of the antibiotic resistance problem, and also to protect human health and food animal production.

In contrast to general belief, it has been found that antibiotic resistant bacteria were abundant in feces from chicks hatched at teaching farm never been exposed to antibiotic treatments. The data illustrated that even if antibiotics were banned from applications in food animal production, the resistant bacteria population already existed in the system won't disappear without specific efforts. Animal feces is the largest reservoir for antibiotic resistant bacteria and resistance genes. Thus, targeted reduction of the antibiotic resistant gut bacteria becomes a priority for control the problem in food animal production.

Lactobacillus crispatus strain WZ-12 (alternatively referred to herein as Lactobacillus crispatus strain CG-12 herein) and multiple E. coli strains were originally isolated from gastrointestinal (GI) tracts of chickens. Being part of the natural microbiota, Lactobacillus crispatus WZ-12 has good colonization fitness in the chicken GI tract, especially during the early establishment of GI microbiota.

Lactobacillus crispatus WZ-12 strain is sensitive to ampicillin and doesn't carry the ampicillin resistance (AR) gene. It is also susceptible to many other antibiotics tested. In vitro assessments showed that Lactobacillus crispatus WZ-12 can inhibit the growth of various bacteria including ampicillin resistant E. coli. Thus, establishment of Lactobacillus crispatus WZ-12 in chicken GI tract at early stage of life may hinder the colonization of antibiotic resistant strains, resulting in a reduced antibiotic resistant population in the chicken GI tract and improve the gut health of the animals. This is critically important for mitigation of AR in the ecosystem.

Lactobacillus crispatus WZ-12 derivatives with increased minimum inhibitory concentration for multiple antibiotics are also contemplated in the present invention. Live cultures in various forms of Lactobacillus crispatus WZ-12 can be commercialized as a probiotic strain or part of the probiotic mix to poultry modulate gut health, improve animal health, and mitigate antibiotic resistance.

Also disclosed herein is a probiotic composition comprising the E. coli strain M9-4-1. The probiotic composition can further comprise Lactobacillus crispatus WZ-12, as well as other known probiotics, such as other strains of bacteria.

Further disclosed is a feed composition comprising Lactobacillus crispatus WZ-12 or a derivative thereof and E. coli strain M9-4-1 or a derivative thereof and an ingestible food product; wherein the composition comprises Lactobacillus crispatus WZ-12 or a derivative thereof and E. coli strain M9-4-1 or a derivative thereof in an amount sufficient for use as a probiotic treatment of a subject.

It is understood that the compositions (comprising e.g., a probiotic bacteria) of the present disclosure can be used in combination with the various compositions, methods, products, and applications disclosed herein.

Disclosed herein is a feed composition comprising Lactobacillus crispatus WZ-12 or a derivative thereof and an ingestible food product; wherein the composition comprises Lactobacillus crispatus WZ-12 or a derivative thereof in an amount sufficient for use as a probiotic treatment of a subject. Lactobacillus crispatus WZ-12 can be given alone, or with Lactobacillus salivarius 1-14 and/or Lactobacillus reuteri 2-2, for example. The bacterial strains disclosed herein (Lactobacillus crispatus WZ-12, Lactobacillus salivarius 1-14, and Lactobacillus reuteri 2-2 or derivatives thereof, for example) may be used alone or in together as a "probiotic" when given to humans or animals. The compositions disclosed herein can be embedded in the ingestible food product, so that the composition is coated or in a gel or other form that can be delivered in the ingestible food product to the subject. In one embodiment, the ingestible food product can retain the viability of the culture. An example of this is an emulsion of peanut butter comprising the composition disclosed herein.

By "Lactobacillus crispatus WZ-12 or a derivative thereof" is meant that the Lactobacillus crispatus WZ-12 may be genetically altered from its naturally occurring state, so that it possesses qualities or genetic elements which are not naturally occurring. For example, the bacteria may be recombinantly engineered to express nonendogenous genes, or may be engineered so that certain native genes are not expressed. The bacteria may be one that has been cultivated in the laboratory so that certain properties are enhanced, or may be genetically modified.

The microbes disclosed herein can be used or alone or in combination with antibiotic compounds or other functional anti-microbial drugs and supplements so as to form therapeutic compositions for use in ameliorating and/or controlling the colonization of pathogenic bacteria with the gastrointestinal tract of both humans and animals. In addition, these non-pathogenic, probiotic bacteria may be co-administered with an anti-fungal agent and/or an antibiotic to ameliorate the growth of the mycotic or bacterial pathogen in question. The compositions of the present invention may or may not be compounded with additional ingredients.

In brief, the present invention utilizes antibiotic-susceptible or antibiotic-tolerant but without transmissible AR genes, non-pathogenic bacteria to mitigate the growth and subsequent establishment of antibiotic-resistant, pathogenic microbes within, for example, the gastrointestinal tract. An example of an antibiotic resistant bacteria includes the ampicillin-resistant *E. coli* strains described herein. The antibiotic resistant bacteria can be multidrug resistant as well. Also disclosed herein are various therapeutic compositions, methods for using said therapeutic compositions, and systems for containing and administering/delivering said therapeutic compositions. Therefore, the probiotic treatment disclosed herein can be effective in reducing an amount of antibiotic resistant bacteria in a gut microbiota of the subject. By "reducing" is meant a 5, 10, 15, 20, 25, 30, 35, 40, 45 50, 55, 60, 65, 70, 75, 80, 85, 90, 95, or 100% reduction in the amount of antibiotic resistant bacteria present in the gut microflora of a subject after having been administered the compositions disclosed herein.

In addition, the present invention also discloses compositions and methodologies for the utilization of these compositions, comprising non-pathogenic, probiotic lactic acid-producing bacteria, in the mitigation of the deleterious physiological effects of gastrointestinal tract pathogens, including antibiotic-resistant gastrointestinal tract pathogens, in both humans and animals, by the colonization (or more-correctly, re-colonization) of the gastrointestinal tract with probiotic microorganisms, following the administration of antibiotics, anti-fungal, anti-viral, and similar agents. The compositions disclosed herein demonstrate beneficial function within the gastrointestinal tract; and are non-pathogenic.

Throughout this specification the compositions of present invention may be referred to as a probiotic composition, a *lactobacillus* containing composition, a dietary supplement, or a food additive or ingestible product. All of these aforementioned terms mean a composition, regardless of form or the presence or absence of other ingredients, that contains viable or non-viable *Lactobacillus crispatus* WZ-12 or a derivative thereof as determined using the methods detailed herein.

The compositions disclosed herein may be taken orally as a bolus in the form of a gelatin capsule, pressed tablet, or gel cap. In another embodiment, the compositions of the present invention may be taken orally in the form of a liquid beverage. The liquid beverage may contain other ingredients such as, but not limited to flavor enhancers, sweeteners, viscosity enhancers and other food additives. The present invention may also be taken together with other foods either separately or compounded therewith.

In some embodiments, the composition is a foodstuff. In this regard, the term "foodstuff" as used herein includes liquids (e.g., drinks), semi-solids (e.g., gels, jellies, yogurt, etc.) and solids. Exemplary foodstuffs include dairy products, such as fermented milk products, unfermented mild products, yogurt, frozen yogurt, cheese, fermented cream, milk-based desserts milk powder, milk concentrate or cheese spread. Other products are also contemplated, such as soy-based products, oat-based products, peanut-based products, chocolate-based products, infant formula, and toddler formula.

The composition can also be presented in the form of a capsule, tablet, dried power, syrup, emulsion, etc. For example, the composition can be a pharmaceutical composition. Such a composition can comprise a pharmaceutically acceptable carrier, e.g., to facilitate the storage, administration, and/or the biological activity of the probiotic (see, e.g., Remington's Pharmaceutical Sciences, 16th Ed., Mac Publishing Company (1980). Suitable carriers for the present disclosure include those conventionally used, e.g., water, saline, aqueous dextrose, lactose, a buffered solution, starch, cellulose, glucose, lactose, sucrose, gelatin, malt, rice, flour, and the like. In some embodiments, the carrier provides a buffering activity to maintain the probiotic at a suitable pH to thereby exert a biological activity.

In a liquid therapeutic composition, the food-grade bacterium can be in suspension in a liquid that ensures physiological conditions for a probiotic bacterium. In a solid therapeutic composition, the food-grade bacterium can be present in free, preferably lyophilized form, or in immobilized form. For example, the food-grade bacterium can be enclosed in a gel matrix which provides protection for the cells.

The compositions disclosed herein can also be given to livestock in the form of a feed additive. For use as a feed additive, the composition may be formulated into a liquid with a high concentration of from 20 to 90%, or may be prepared as a powder or granules or emulsion. The feed additive may include at least one selected from the group consisting of an organic acid such as citric acid, fumaric acid, adipic acid, lactic acid, or malic acid, a phosphate salt such as sodium phosphate, potassium phosphate, acidic pyrophosphate, or polyphosphate (polymerized phosphate), and a natural antioxidant such as polyphenol, catechin, a-tocopherol, rosemary extract, vitamin C, green tea extract, licorice extract, chitosan, tannic acid, or phytic acid, various fatty acids, proteins, carbohydrates. The composition used as livestock feed may be formulated into various forms that are commonly used in the art with ingredients commonly used in livestock feed.

The feed additive and livestock feed may include grains such as powdered or pulverized wheat, oats, barley, corn, or rice; plant protein livestock feed containing rape, bean, or sunflower as a main ingredient; animal protein livestock feed such as blood powder, meat powder, bone powder, or fish powder; sugar; and dairy products such as powdered milk and whey powder. The feed additive and livestock feed may further include nutrient supplements, digestion- and absorption-assisting agents, growth promoting substances, or the like.

The livestock feed additive may be administered, alone or in combination with another edible excipient, to animals. In addition, the livestock feed additive may be administered as a top dressing to the livestock feed or as a mixture with the livestock feed, or in separate oral form. If the feed additive is administered separately from the livestock feed, it is combined with a pharmaceutically acceptable vehicle to prepare an immediate release or sustained release formulation. The edible vehicle may be solid or liquid, such as corn starch, lactose, sucrose, bean flake, peanut oil, olive oil, sesame oil, or propylene glycol. When a solid vehicle is used, the feed additive may be in the form of tablets, capsules, powder, troches or lozenges, or a non-dispersed top dressing. As for a liquid vehicle, the feed additive may be in the form of gelatin soft capsules, a syrup suspension, an emulsion, or a solution.

The livestock feed may include protein-containing organic cereal flour that is commonly used to satisfy the dietary demand of animals. The protein-containing cereal flour may comprise corn, bean flour, or a corn/bean flour mix.

In addition, the feed additive and livestock feed may include a supplement such as a preservative, a stabilizer, a wetting agent, an emulsifier, and a solubilizer. The feed additive may be added to the livestock feed in an infiltration, spraying, or mixing manner.

The compositions of the present invention can be administered to any animal in need of thereof including, but not limited to mammals, birds, reptiles and fish. Typical applications include administering the probiotic compositions of the present invention to humans, horses, swine (pigs), cows, sheep, dogs, cats, rabbits, chickens, turkeys, pheasants, quail, parakeets, parrots, and other wild and domesticated animals.

In one embodiment of the present invention, the composition is given as a dietary supplement. For example, when given to humans, the compositions disclosed herein can be given as a dietary supplement. Th dietary supplement, in one example, can comprise a gelatin capsule filled with the bacterial strain(s) disclosed herein. In another embodiment, the dietary supplement is in the form of a liquid preparation. In yet another embodiment of the present invention, the dietary supplement is in the form of an anal or vaginal suppository. When used as a suppository it may be formed into a convenient bolus and may contain non-toxic lubricants, stabilizers, waxes and the like to ease in the administration. In another embodiment of the present invention the lactobacillus dietary supplement may be compounded with foods such as, but not limited to dairy products, grains, breads, meats, fruits, vegetables, rice and the like. The form the lactobacillus dietary supplement of the present invention assumes is not important and is non-limiting.

It should also be noted that the present invention is not limited solely to oral administration of the compositions disclosed herein. For example, antibiotic and anti-fungal resistance is also associated with topical and intra-vaginal medications. Thus, in an additional embodiment, the co-administration of a beneficial bacterial culture with a vaginal anti-fungal medication would effectively aid in the mitigation of the mycotic or bacterial pathogen in question and repopulate the vagina and reduce the incidence of relapse. It should be noted that it has been demonstrated that the absence of lactic acid-producing bacteria within the vagina is the most common etiology of vaginal yeast infections and bacterial vaginosis.

In an additional embodiment, skin creams, lotions, gels and the like could similarly contain a beneficial biorational component that would be effective in controlling pathogenic organisms on the skin and further reduce the emergence of antibiotic resistant pathogens. By way of example, but not of limitation, the cells, spores or extracellular materials from such beneficial biorational bacteria could be incorporated into these skin products for this express purpose. Burn patients usually are given antibiotics to reduce the incidence of opportunistic infection. Pathogenic *Pseudomonas*, *Staphylococcus*, and/or Enterococci are frequently associated with infections of severe burns. Hence, the salves, lotions, gels and the like combined with the beneficial, biorational microorganisms or their extracellular products, as disclosed in the present invention, would be effective in achieving a state of proper biodiversity to the skin in burn cases, as, generally, such biodiversity is not associated with pathogenic overgrowth.

In one embodiment of the present invention the composition is freeze dried using standard methods known to those having ordinary skill in the art of food science. In another embodiment the composition of the present invention the composition is air-dried. In yet another embodiment the composition is a paste. In still another embodiment the composition of the present invention is a liquid.

In yet another specific embodiment, the *Lactobacillus crispatus* WZ-12 composition may be incorporated into an aqueous solution (e.g., physiological saline) for administration as a colonic, via an enema or the like) so as to directly administer the probiotic bacteria to the colon. This method of administration is highly efficacious for utilization of vegetative bacterial cells as they are not exposed to the highly acidic environment of the stomach as is the case during oral administration.

The composition comprising *Lactobacillus crispatus* WZ-12 or a derivative thereof can comprise *Lactobacillus crispatus* WZ-12 or a derivative thereof in an amount from $1 \times 10^4$ to $1 \times 10^7$ colony forming units per milliliter. For example, the amount can be $1 \times 10^4$, $1 \times 10^5$, $1 \times 10^6$, or $1 \times 10^7$, or any amount in between, above, or below. The *Lactobacillus crispatus* WZ-12 compositions disclosed herein can contain sufficient colony-forming units (CFU) to compete with undesirable microorganisms, such as *E. coli* and *Salmonella*. The total amount consumed will depend on the individual needs of the animal and the weight and size of the animal. The preferred dosage for any given application can be easily determined by titration. Titration is accomplished by preparing a series of standard weight doses each containing from approximately $10^5$ to $10^{11}$ bacteria per gram. A series of doses are administered beginning at 0.5 grams and continuing up to a logical endpoint determined by the size of the animal and the dose form. The appropriate dose is reached when the minimal amount of lactobacilli composition required to achieve the desired results is administered. The appropriate dose is also known to those skilled in the art as an "effective amount" of the probiotic compositions of the present invention.

The growth of the lactobacilli species disclosed herein to form cell cultures, cell pastes, and spore preparations is generally well-known within the art. It should be noted that the exemplary culture and preparative methods which are described herein may be readily utilized and/or modified for growth and preparation of other bacteria disclosed in the present invention.

The formulation for the composition disclosed herein may also include other probiotic agents or nutrients which promote spore germination and/or bacterial growth. For example, the *Lactobacillus crispatus* WZ-12 strain disclosed herein can be combined with a therapeutically-effective dose of an antibiotic. The therapeutic composition of the present invention may also contain approximately 1 to approximately 250 mg of the selected antibiotic per unit of composition. In preferred embodiments of the present invention, the *Lactobacillus crispatus* WZ-12 strain can combined with a therapeutic dose of an antibiotic such as Gentamicin; Vancomycin; Oxacillin; Tetracyclines; Nitrofurantoin; Chloramphenicol; Clindamycin; Trimethoprim-Sulfamethoxasole; a member of the Cephlosporin antibiotic family (e.g., Cefaclor, Cefadroxil, Cefixime, Cefprozil, Ceftriaxone, Cefuroxime, Cephalexin, Loracarbef, and the like); a member of the Penicillin family of antibiotics (e.g., Ampicillin, Amoxicillin/Clavulanate, Bacampicillin, Cloxicillin, Penicillin VK, and the like); with a member of the Fluoroquinolone family of antibiotics (e.g., Ciprofloxacin, Grepafloxacin, Levofloxacin, Lomefloxacin, Norfloxacin, Ofloxacin, Sparfloxacin, Trovafloxacin, and the like); or a member of the Macrolide antibiotic family (e.g., Azithromycin, Erythromycin, and the like).

The *Lactobacillus crispatus* WZ-12 strain can also be combined with a therapeutically-effective dose of an anti-fungal agent. The therapeutic composition of the present invention may also contain approximately 1 to 250 mg of the selected anti-fungal agent per unit of therapeutic composition. Typical anti-fungal agents which may be utilized include, but are not limited to: Clotrimazole, Fluconazole, Itraconazole, Ketoconazole, Miconazole, Nystatin, Terbinafine, Terconazole, Tioconazole, and the like.

The *Lactobacillus crispatus* WZ-12 compositions of the present invention may also include known antioxidants, buffering agents, and other agents such as coloring agents, flavorings, vitamins or minerals. For example, a preferred therapeutic composition may also contain one or more of the following minerals: calcium citrate (15-350 mg); potassium gluconate (5-150 mg); magnesium citrate (5-15 mg); and chromium picollinate (5-200 μg). In addition, a variety of salts may be utilized, including calcium citrate, potassium gluconate, magnesium citrate and chromium picollinate. Thickening agents may be added to the compositions such as polyvinylpyrrolidone, polyethylene glycol or carboxymethylcellulose. Preferred additional components of a therapeutic composition of this invention can include assorted colorings or flavorings, vitamins, fiber, enzymes and other nutrients. Preferred sources of fiber include any of a variety of sources of fiber including, but not limited to: *psyllium*, rice bran, oat bran, corn bran, wheat bran, fruit fiber and the like. Dietary or supplementary enzymes such as lactase, amylase, glucanase, catalase, and the like enzymes can also be included. Chemicals used in the present compositions can be obtained from a variety of commercial sources, including Spectrum Quality Products, Inc (Gardena, Calif.), Sigma Chemicals (St. Louis, Mich.), Seltzer Chemicals, Inc., (Carlsbad, Calif.) and Jarchem Industries, Inc., (Newark, N.J.).

The various active agents (e.g., probiotic bacteria, antibiotics, anti-fungal agents, bifidogenic oligosaccharides, and the like) are combined with a carrier which is physiologically compatible with the gastrointestinal tissue of the species to which it is administered. Carriers can be comprised of solid-based, dry materials for formulation into tablet, capsule or powdered form; or the carrier can be comprised of liquid or gel-based materials for formulations into liquid or gel forms. The specific type of carrier, as well as the final formulation depends, in part, upon the selected route(s) of administration.

The *Lactobacillus crispatus* WZ-12 composition of the present invention may also include a variety of carriers and/or binders. A preferred carrier is micro-crystalline cellulose (MCC) added in an amount sufficient to complete the one gram dosage total weight. Particularly preferred formulations for a therapeutic composition of this invention will be described, infra. Carriers can be solid-based dry materials for formulations in tablet, capsule or powdered form, and can be liquid or gel-based materials for formulations in liquid or gel forms, which forms depend, in part, upon the routes of administration.

Typical carriers for dry formulations include, but are not limited to: trehalose, malto-dextrin, rice flour, micro-crystalline cellulose (MCC) magnesium sterate, inositol, FOS, GOS, dextrose, sucrose, and like carriers. Where the composition is dry and includes evaporated oils that produce a tendency for the composition to cake (adherence of the component spores, salts, powders and oils), it is preferred to include dry fillers which distribute the components and prevent caking. Exemplary anti-caking agents include MCC, talc, diatomaceous earth, amorphous silica and the like, and are typically added in an amount of from approximately 1% to 95% by weight. It should also be noted that dry formulations which are subsequently rehydrated (e.g., liquid formula) or given in the dry state (e.g., chewable wafers, pellets or tablets) are preferred to initially hydrated formulations. Dry formulations (e.g., powders) may be added to supplement commercially available foods (e.g., liquid formulas, strained foods, or drinking water supplies). Similarly, the specific type of formulation depends upon the route of administration.

Suitable liquid or gel-based carriers include but are not limited to: water and physiological salt solutions; urea; alcohols and derivatives (e.g., methanol, ethanol, propanol, butanol); glycols (e.g., ethylene glycol, propylene glycol, and the like). Preferably, water-based carriers possess a neutral pH value (i.e., pH 7.0). The compositions may also include natural or synthetic flavorings and food-quality coloring agents, all of which must be compatible with maintaining viability of the microorganism. Well-known thickening agents may also be added to the compositions such as corn starch, guar gum, xanthan gum, and the like. By way of example and not of limitation, preferred inhibitors include: hyper-saline carriers, methylparaben, guargum, polysorbates, preservatives, and the like.

Preservatives may also be included within the carrier including methylparaben, propylparaben, benzyl alcohol and ethylene diamine tetraacetate salts. Well-known flavorings and/or colorants may also be included within the carrier. The compositions of the present invention may also include a plasticizer such as glycerol or polyethylene glycol (with a preferred molecular weight of MW=800 to 20,000). The composition of the carrier can be varied so long as it does not interfere significantly with the pharmacological activity of the active ingredients.

When used as a dietary supplement or foodstuff, the composition can include any of a variety of nutritional agents, as are well known, including vitamins, minerals, essential and non-essential amino acids, carbohydrates, lipids, foodstuffs, dietary supplements, and the like. Preferred compositions comprise vitamins and/or minerals in any combination. Vitamins for use in a composition of this invention can include vitamins B, C, D, E, folic acid, K, niacin, and like vitamins. The composition can contain any or a variety of vitamins as may be deemed useful for a particularly application, and therefore, the vitamin content is not to be construed as limiting. Typical vitamins are those, for example, recommended for daily consumption and in the recommended daily amount (RDA), although precise amounts can vary. The composition would preferably include a complex of the RDA vitamins, minerals and trace minerals as well as those nutrients that have no established RDA, but have a beneficial role in healthy human or animal physiology. The preferred mineral format would include those that are in either the gluconate or citrate form because these forms are more readily metabolized by lactobacilli. In a related embodiment, the invention contemplates a composition comprising a viable *Lactobacillus crispatus* WZ-12 composition in combination with any material to be adsorbed, including but not limited to nutrient supplements, foodstuffs, vitamins, minerals, medicines, therapeutic compositions, antibiotics, hormones, steroids, and the like compounds where it is desirable to insure efficient and healthy absorption of materials from the gastrointestinal track into the blood. The amount of material included in the composition can vary widely depending upon the material and the intended purpose for its absorption, such that the invention is not to be considered as limiting. Other components of the compositions of the present invention can be a bifidogenic oligosaccharide, as described herein.

As mentioned above, the composition disclosed herein can comprise more than one probiotic bacteria. For example, the composition can comprise *Lactobacillus salivarius* 1-14 or a derivative thereof, or *Lactobacillus reuteri* 2-2 or a derivative thereof. The composition can comprise two or more bacteria selected from the group consisting of *Lactobacillus crispatus* WZ-12 or a derivative thereof, *Lactobacillus salivarius* 1-14 or a derivative thereof, or *Lactobacillus reuteri* 2-2 or a derivative thereof.

Methods

Disclosed herein is a method of modulating gut microbiota in a subject comprising administering a composition comprising *Lactobacillus crispatus* WZ-12 or a derivative thereof to the subject. The disclosed methods of treatment function so as to inhibit the growth of the pathogenic bacteria which are associated with gastrointestinal infections, as well as to concomitantly mitigate the deleterious physiological effects/symptoms of these pathogenic infections.

The amount of antibiotic resistant bacteria in a gut microbiota of the subject can be determined after the administration step. For example, such determination can comprise measuring an amount of $bla_{CMY-2}$ or other antibiotic resistance gene(s) in a fecal sample of the subject.

The compositions disclosed herein can be used to modulate gut microflora in a variety of ways, which can be customized to the subject receiving the treatment. For example, the treatment can occur in 2, 3, 4, 5, 6, 7, or more doses. The doses can be given once every day, or can be administered multiple times throughout the same day. One of skill in the art will appreciate that the doses can be administered in a variety of ways. The compositions disclosed herein can be administered in utero, or in the case of fowl, in ovo, or can be given upon birth, or 1, 2, 3, 4, 5, 6, 7, or more days after birth. The compositions can be administered to adults as a routine additive, or can be administered on an as-needed basis.

Disclosed herein is a bacterial strain comprising a *Lactobacillus crispatus* WZ-12, *Lactobacillus salivarius* 1-14, or *Lactobacillus reuteri* 2-2 derivative engineered to comprise a derivative genome which differs from a parental genome of the parental strain by at least one nucleotide, and which improves one or more probiotic qualities of the engineered bacterial strain compared to the parental strain. In one example, the derivative lacks a mobile genetic element present in the parental strain. The mobile genetic element can comprise a phage polynucleotide or an integron polynucleotide encoding one or more polypeptides capable of facilitating horizontal gene transfer. The derivative can lack a polynucleotide encoding an antibiotic resistance polypeptide present in the parental strain.

The derivative can have the improved quality comprises increased modulation of a gut microbiota in a subject as compared to the parental strain. The increased modulation can comprise colonizing the gut microbiota of the subject for a greater duration than the parental strain. The increased modulation can comprise reducing the amount of antibiotic resistant bacteria in the gut microbiota of the subject more than the parental strain.

Probiotic lactic acid bacterium, including *Lactobacillus crispatus*, are generally regarded as safe by those skilled within the art (i.e., GRAS Certified by the FDA) and, therefore, suitable for direct ingestion in food stuffs or as a food supplement. The methods of the present invention comprise administration of a therapeutic composition containing *Lactobacillus crispatus* WZ-12 or a derivative thereof to the gastrointestinal tract of a human or animal, to treat or prevent bacterial infection. Administration is preferably made using a liquid, powder, solid food and the like formulation compatible with oral administration, all formulated to contain a therapeutic composition of the present invention by use of methods well-known within the art.

The methods of the present invention include administration of *Lactobacillus crispatus* WZ-12 or a derivative thereof to a human or animal, so as to treat or prevent the colonization of antibiotic-resistant pathogens with the gastrointestinal tract. In particular, for VRE, VISA, PRP, and other pathogens, the methods include administering to the patient, for example, *Lactobacillus crispatus* WZ-12 or a derivative thereof in food or as a food supplement. Oral administration is preferably in an aqueous suspension, emulsion, powder or solid, either already formulated into a food, or as a composition which is added to food by the user prior to consumption. Administration to the gastrointestinal tract may also be in the form of an anal suppository (e.g., in a gel or semi-solid formulation). All such formulations are made using standard methodologies.

Administration of a therapeutic composition is preferably to the gastrointestinal tract using a gel, suspension, aerosol spray, capsule, tablet, powder or semi-solid formulation (e.g., a suppository) containing a therapeutic composition of the present invention, all formulated using methods well-known within the art. Of course, the specific route, dosage and timing of the administration will depend, in part, upon the particular pathogen and/or condition being treated, as well as the extent of said condition.

The present invention further contemplates a therapeutic system for treating, reducing and/or controlling pathogenic bacterial infections. Typically, the system is in the form of a package containing a therapeutic composition of the present invention, or in combination with packaging material. The packaging material includes a label or instructions for use of the components of the package. The instructions indicate the contemplated use of the packaged component as described herein for the methods or compositions of the invention.

By way of example, and not of limitation, a system can comprise one or more unit dosages of a therapeutic composition according to the present invention. Alternatively, the system can alternately contain bulk quantities of a therapeutic composition. The label contains instructions for using the therapeutic composition in either unit dose or in bulk forms as appropriate, and may also include information regarding storage of the composition, disease indications, dosages, routes and modes of administration and the like information.

EXAMPLES

To further illustrate the principles of the present disclosure, the following examples are put forth so as to provide those of ordinary skill in the art with a complete disclosure and description of how the compositions, articles, and methods claimed herein are made and evaluated. They are intended to be purely exemplary of the invention and are not intended to limit the scope of what the inventors regard as their disclosure. These examples are not intended to exclude equivalents and variations of the present invention which are apparent to one skilled in the art. Unless indicated otherwise, temperature is ° C. or is at ambient temperature, and pressure is at or near atmospheric. There are numerous variations and combinations of process conditions that can be used to optimize product quality and performance. Only reasonable and routine experimentation will be required to optimize such process conditions.

Example 1

Abstract

The gastrointestinal (GI) microbiota consists of a large number of bacterial cells, but less than 1% are cultivable. Nevertheless, cultivable bacteria provide important information on GI ecology, including the profile of antibiotic resistance (AR). This example identifies several culture-recovered commensal bacterial strains isolated from chicken feces, and examines their potential contribution to AR ecology. Three $Amp^r$ $E.$ $coli$ ($E.$ $coli$ CA-1 or y M9-1 elsewhere, $E.$ $coli$ CA-4 or elsewhere M9-4 and $E.$ $coli$ CA-20 or M9-12 elsewhere) strains were identified as resistant to β-lactam, erythromycin, daptomycin, vancomycin and linezolid antibiotics, but susceptible to tetracycline and quinolone antibiotics. $Lactobacillus$ $crispatus$ WZ-12 (sometimes referred to simply as "WZ-12") was isolated and susceptible to most antibiotics examined, but resistant to quinolone and daptomycin. The result was consistent with data by whole genome sequence analysis.

Materials and Methods

Bacterial strains. Multiple $Amp^r$ strains from feces of broiler chickens without antibiotic treatment were recovered on Columbia blood Agar base (Becton, 100 Dickinson and Company, Franklin Lakes, N.J.) supplemented with 5% defibrinated sheep blood (Thermo Scientific™, Grand Island, N.Y.). The strains were maintained in Columbia broth (Becton Dickinson and Company, Franklin Lakes, N.J.), and propagated by aerobic growth at 37° C., and further subjected to strain identification and Minimum Inhibition Concentration (MIC) assessments.

Multiple commensal bacterial strains from chicken feces were recovered from Columbia blood Agar base (Becton, 100 Dickinson and Company, Franklin Lakes, N.J.) supplemented with 5% defibrinated sheep blood (Thermo Scientific™, Grand Island, N.Y.), and maintained in Columbia broth (Becton Dickinson and Company, Franklin Lakes, N.J.) and propagated by anaerobic growth at 37° C. The strains were subjected to antibiotic susceptibility assessment followed by strain identification.

Screening of antibiotic susceptible commensal strains. Recovered commensal strain isolates (over 1000 colonies) were spotted on Columbia broth (Becton, 100 Dickinson and Company, Franklin Lakes, N.J.) agar plates containing each of the four antibiotics for rapid assessment of phenotypic resistance profiles. Screened antibiotics included 16 μg/mL tetracycline (Sigma-Aldrich, St. Louis, Mo., USA), 100 μg/mL erythromycin (Fisher Scientific, Waltham, Mass., USA), 32 μg/mL ampicillin (Sigma-Aldrich), and 152 μg/mL sulfamethoxazole (Sigma-Aldrich) with 8 μg/mL trimethoprim (Sigma-Aldrich).

Strain identification. Phylotype identity and AR determinants were examined by conventional PCR. Primers used for identification and gene screening are listed in Table 1 and were synthesized by Sigma-Aldrich. The sequence of the 16S rRNA amplicon was confirmed by DNA sequencing at the Plant Microbe Genomics Facility of the Ohio State University and compared with published AR gene sequences deposited in the NCBI database. An API® 50CH (Biomerieus, Durham, N.C., US) identification strip was used for further identification of $Lactobacillus$.

TABLE 1

Primers used in strain identification.

| Primer | Sequence | Amplicon size | Reference |
|---|---|---|---|
| $bla_{CMY-2}$ FP | GACAGCCTCTTTC TCCACA | 1,143 bp | (Zhao and others, 2001) |
| $bla_{CMY-2}$ RP | TGGAACGAAGGCT ACGTA | | |
| 16S-357F-GC | CGCCCGCCGCGCG CGGCGGGCGGGGC GGGGGCACGGGGG GCCTACGGGAGGC AGCAG | 233 bp | (Muyzer and others, 1993) |
| 16S-518R | ATTACCGCGGCTG CTGG | | |

FP: forward primer;
RP: reversed primer (SEQ ID NOS: 1-6, respectively)

Minimum inhibition concertation (MIC) assessment. A TREK Sensititre diagnostic system (Thermo scientific, Oakwood Village, Ohio, USA) was used to assess the AR phenotype and MIC of isolated strains. Cation-adjusted Mueller Hinton Broth (Becton, Dickinson and Company, MD, USA) was used as basic medium.

Shotgun whole genome sequencing, assembly and annotation. DNA of $Lactobacillus$ $crispatus$ WZ-12 was extracted from a colony using an UltraClean® Microbial DNA Isolation Kit (Mo Bio Laboratories Inc; Carlsbad, Calif., USA). DNA was sent to the Nationwide Children's hospital (Columbus, Ohio USA) for sequencing on an Illumina HiSeq 2500 system (Illumina Inc; San Diego, Calif., USA). Assembly of bacterial genome was performed using CLC Genomics Workbench 9.0 (CLC bio; Katrinebjerg, Denmark). Reference mapping of reads was performed using the genome of the $Lactobacillus$ $crispatus$ ST1 (GenBank accession no. FN692037.1). The assembled contigs were aligned to the Comprehensive Antibiotic Resistance Database (CARD) to search for AR determinants (McArthur et al., 2013). Annotation of the assembled contigs was performed on the RAST (Rapid Annotation using Subsystem Technology) server (Aziz et al., 2008; Overbeek et al., 2014; Brettin et al., 2015).

Results

Identification and characterization of $E.$ $coli$ strains. NCBI blast results of the 16S rRNA sequence from the $Amp^r$ strains showed that all three strains of interest had 100% query coverage and over 98% sequence identity to the $E.$ $coli$ 16S rRNA sequences in NCBI database. The three strains were designated as $E.$ $coli$ CA-1 (M9-1 elsewhere), $E.$ $coli$ CA-4 (M9-4 elsewhere), $E.$ $coli$ CA-20 (M-12 elsewhere). All three $E.$ $coli$ strains were $bla_{CMY-2}^+$ by conventional PCR. The bla gene encodes β-lactamase, an enzyme which cleaves β-lactam antibiotics, thereby conferring resistance to this class of antibiotics (including ampicillin). MIC assessments results of the $E.$ $coli$ strains were listed in Table 2. The MIC profiles of $E.$ $coli$ CA-1 AND $E.$ $coli$ CA-4 were highly identical. Three $Amp^r$ $E.$ $coli$ had high resistance to β-lactam antibiotics (except for ceftriaxone), for example penicillin, ampicillin and oxacillin. Only $E.$ $coli$ CA-20 had some resistant to ceftriaxone. The $E.$ $coli$ strains were also resistant to erythromycin and some peptide antibiotics (daptomycin, vancomycin and linezolid). But they had low MIC values for tetracycline and quinolones, indicating susceptibility to these two categories of antibiotics.

Identification and characterization of commensal *Lactobacillus* strains. Among over 1,000 strains examined, a strain was isolated which was susceptible to ampicillin, tetracycline, erythromycin and sulfonamide/trimethoprim. The strain was named CG-12 (referred to herein as WZ-12, alternatively) and originated from Leghorn chicken. CG-12 was identified to be *Lactobacillus* by 16S rRNA gene sequence assessment without a confirmed species. The API® 50CH result indicated the tested susceptible strain had 99.9% possibility to be *Lactobacillus crispatus*. This strain was thus designated as *Lactiobacillus crispatus* CG-12. *Lactobacillus crispatus* CG-12 was $bla_{CYM-2}^-$ by PCR, indicating the absence of a β-lactam resistance gene. *Lactobacillus crispatus* CG-12 had low MIC values for most tested antibiotics (Table 2), but was resistant to daptomycin and quinolone (levofloxacin, gatifloxacin and ciprofloxacin).

TABLE 2

MIC of selected antibiotics for *E. coli* CA-1, *E. coli* CA-4, *E. coli* CA-20 and *Lactobacillus crispatus* CG-12.

| Antibiotic | E.coli CA-1 | E.coli CA-4 | E.coli CA-20 | L. crispatus CG-12 |
|---|---|---|---|---|
| ERY | >4 | >4 | >4 | <0.25 |
| CLI | >2 | >2 | >2 | <0.12 |
| SYN | >4 | >4 | >4 | 0.25 |
| DAP | >8 | >8 | >8 | 4 |
| VAN | >128 | >128 | >128 | <1 |
| TET | <2 | <2 | <2 | <2 |
| AMP | >16 | >16 | >16 | 0.5 |
| GEN | 4 | 4 | 8 | 16 |
| LEVO | <0.25 | <0.25 | <0.25 | >8 |
| LZD | >8 | >8 | >8 | 2 |
| AXO | <8 | <8 | 16 | <8 |
| STR | <1000 | <1000 | <1000 | <1000 |
| PEN | >8 | >8 | >8 | 0.5 |
| RIF | 4 | >4 | 4 | 1 |
| GAT | <1 | <1 | <1 | 4 |
| CIP | <0.5 | <0.5 | <0.5 | >2 |
| SXT | <0.5/9.5 | <0.5/9.5 | <0.5/9.5 | 2/38 |
| OXA+ | >8 | >8 | 8 | <0.25 |

MIC values are expressed in µg/mL. ERY: erythromycin; CLI: clindamycin; SYN: quinupristin/dalfopristin; DAP: daptomycin; VAN: vancomycin; TET: tetracycline; AMP: ampicillin; GEN: gentamicin; LEVO: levofloxacin; LZD: linezolid; AXO: ceftriaxone; STR: streptomycin; PEN: penicillin; RIF: rifampin; GAT: gatifloxacin; CIP: ciprofloxacin; SXT: sulfamethoxazole/trimethoprim; OXA+: oxacillin+2% NaC.

Whole genome sequence assessment of *Lactobacillus crispatus* CG-12. A total of 63 contigs longer than 1,000 bps were assembled from sequence data with a total length of 2,046,783 bp. Compared to a Genebank reference strain (*Lactobacillus crispatus* ST1, Genebank sequence No. FN692037.1), full length chromosomal genome (2,043,161 bp), the sequence coverage was nearly complete.

Two AR-related gene sequences were detected in the scaffold genome when compared to CARD database. A 346 bp sequence that had 77% identity to *Staphylococcus aureus* parE gene was observed on Contig 11 (153,379 bp). It encoded DNA topoisomerase IV subunit B, which conferrs resistance to aminocoumatin and fluoroquinolones. Another 737 bp sequence that had 73% identity to *Staphylococcus aureus* rpoC was located on Contig 22 (65,018 bp). It encoded DNA-directed RNA polymerase β-subunit and confers resistance to distamycin. These results were consistent with MIC tests.

RAST server annotations indicated there were phage-related genes in the genome of *Lactobacillus crispatus* CG-12. Phage related genes include phage replication initiation protein, phage anti-repressor protein, phage integrase, phage immunity repressor, among others.

Discussion and Conclusions

Strain identification is important in the study of antibiotic resistance in commensal microbiota. Bacterial strain prevalence and AR profile is a good indication of the overall AR status in the microbiota.

Three $Amp^r$ isolates were identified and determined to be *Escherichia coli*. The AR gene $bla_{CMY-2}$ was detected in all three strains. These *E. coli* strains had high resistance to β-lactam antibiotics according to the MIC test. Similarity in MIC profile observed between *E. coli* CA-1 and *E. coli* CA-4 indicated these two strains may be identical.

An ampicillin-susceptible strain CG-12 was identified as *Lactobacillus crispatus*. *Lactobacillus crispatus* is a commensal bacterial species prevalent in neonatal GI microbiota. *Lactobacillus crispatus* CG-12 was susceptible to most tested antibiotics but has relatively high resistance to quinolone antibiotics and daptomycin. This result is consistent with whole genome sequence analysis, as sequences with high homology to the parE and rpoC genes were observed in the CG-12 genome. Other beta-lactam resistance genes were not observed. The presence of phage-related genes indicates that gene transfer activity was potentially involved during the evolution of this strain.

The three $bla_{CMY-2}^+$ *E. coli* strains have high resistance to β-lactams and can be used as indicators for responses to ampicillin selective pressure. The commensal $bla_{CMY-2}^-$ *Lactobacillus crispatus* CG-12 has low resistance to most commonly used antibiotics and no $Amp^r$ gene was detected on its genome. Thus, CG-12 is useful for probiotic methods of countering AR strains in GI microbiota.

Example 2

Abstract

Antibiotic-susceptible *Lactobacillus crispatus* strain CG-12 was isolated and characterized for antibiotic susceptibility profiles and whole genome sequencing. In vitro studies showed the strain can inhibit the growth of $bla_{CMY-2}^+$ *E. coli* strains, isolated from natural chicken fecal microbiota. *Lactobacillus crispatus* CG-12 was examined in vivo using a chicken model to test colonization resistance against $bla_{CMY-2}^+$ *E. coli* in gut microbiota. *Lactobacillus crispatus* CG-12 reduced the prevalence of the $bla_{CMY-2}$ gene in newly established GI microbiota. Pre-inoculation of *Lactobacillus crispatus* CG-12 at an early stage didn't prevent colonization by AR *E. coli*. 10 days of inoculation of *Lactobacillus crispatus* CG-12 had little effect on eliminating the particularly targeted (inoculated) AR bacteria and reducing AR proliferation during antibiotic challenge. Post-antibiotic administration of *Lactobacillus crispatus* CG-12 did not significantly recover the diversified constitution of GI microbiota. Thus, administration of *Lactobacillus crispatus* CG-12 significantly reduced the early establishment of the $bla_{CMY-2}$ gene pool, but had limited impact on AR *E. coli* from colonization to proliferation. This example shows that *Lactobacillus crispatus* was prevalent in neonatal GI microbiota of chicken, and that antibiotic-susceptible *Lactobacillus crispatus* CG-12 reduced early establishment of the AR gene pool.

Materials and Methods

Bacterial strains and culture preparation. Three $bla_{CMY-2}^+$ *Escherichia coli* strains were isolated from feces of two 4-day-old broiler chickens. *E. coli* strains were incubated separately in Columbia Broth (Becton, 100 Dickinson and Company, Franklin Lakes, N.J.) at 37° C. *Lactobacillus crispatus* CG-12 was isolated from feces of 3-week-old Leghorn chickens, and was incubated in MRS broth (Becton, 100 Dickinson and Company, Franklin Lakes, N.J.) at 37° C. For inocula preparations, 1 mL of overnight culture was precipitated by centrifugation (8000×g, 1 minute), washed and re-suspended in 1 mL saline. A cocktail of three *E. coli* strains for inoculation was prepared by mixing the cell suspension of designated strains and standardized to $10^6$ CFU/mL per each strain.

Growth inhibition assessments: Agar diffusion. Bacterial competition assays were performed in a 1×3 matrix format by an agar diffusion technique (Durso et al., 2004). Supernatant producer and receptor strains were grown overnight in MRS at 37° C. anaerobically. Producer strain culture was centrifuged at 10000×g for 5 min, and the supernatants were filtered by 0.22 mm filter to remove remaining cells. Receptor strain cells were inoculated into tempered soft Columbia agar (20 µl of cells culture into 3 mL soft agar) and overlaid onto Columbia agar plates. Three sterile 6-mm-diameter paper disks were placed on the agar in each plate, and 25 µl of each supernatant was inoculated onto each disk. Plates were incubated anaerobically overnight at 37° C. Zones of clearance were recorded in millimeters.

Growth inhibition assessments: Efficacy of inhibition by metabolites. Overnight cultures of three *E. coli* strains ($10^6$ CFU/mL) were mixed at equal volume as the *E. coli* mix. Overnight cultures of *Lactobacillus crispatus* CG-12 ($10^6$ CFU/mL, 10 µl) were inoculated into 10 mL MRS broth and incubated anaerobically overnight at 37° C. The culture was centrifuged at 10,000×g for 5 min, and the supernatant was filtered by 0.22 mm filter to remove remaining cells. The inhibition volume of this supernatant against AR *E. coli* culture was tested in a series of modulated MRS media listed in Table 3. The media was modulated based on an assumption that 40% nutrient in the supernatant was depleted. Another set of 1×MRS media was modified in pH. The pH was identical to each supernatant-modified media. This set of media was used to evaluate the impact of pH on the inhibition activity.

TABLE 3

Modulated media used for growth inhibition test.

| Supernatant % | Supernatant (mL) | 3× MRS (mL) | 1× MRS (mL) | pH | Total (mL) |
|---|---|---|---|---|---|
| 0% | — | — | — | 6.42 | 5 |
| 5% | 0.25 | 0.05 | 4.7 | 5.87 | 5 |
| 10% | 0.5 | 0.1 | 4.4 | 5.49 | 5 |
| 20% | 1 | 0.2 | 3.8 | 5.03 | 5 |
| 40% | 2 | 0.4 | 2.6 | 4.58 | 5 |
| 50% | 2.5 | 0.5 | 2 | 4.42 | 5 |

The chicken model. All procedures were approved by the Institutional Animal Care and Use Committee (protocol No. 2012A00000061, The Ohio State University, Columbus, Ohio). Leghorn chicken were hatched and maintained at the Ohio Agricultural Research and Development Center (OARDC) poultry research teaching farm (two birds per cage with separate feed and water supply, controlled temperature, filtered air in the room and sterilized feed). Chicken fecal samples were collected on-site and examined for the presence of $bla_{CMY-2}$ gene pools and microbial profile. Beginning on Day 5 post-hatch, chicken were inoculated with a $bla_{CMY-2}^+$ *E. coli* cocktail (0.2 mL/bird, $10^6$ CFU/mL) every 24 hours for 4 consecutive days via gavage feeding using 20 ga×1.5 inch animal feeding needle (Fine Science Tools, Foster City, Calif., USA). Chickens in non-inoculated control groups were fed with 0.2 mL of saline by the same method. Chickens were then set in cages for 11 days before antibiotic treatment, allowing the microbiota to stabilize.

*Lactobacillus crispatus* and antibiotic administration. *Lactobacillus crispatus* CG-12 was susceptible to ampicillin. To monitor the impact of CG-12 on AR profiles during common ampicillin administration practice, low veterinary Amp dosages (30 mg/kg body weight per day) were selected instead of 300 mg/kg/day. *Lactobacillus crispatus* CG-12 was administrated in three periods: 1) Day 2 to Day 4 post-hatch; 2) throughout the stabilization; and 3) post-antibiotic challenge on Day 25 to Day 28. During these periods, chickens were inoculated with a *Lactobacillus crispatus* CG-12 suspension (0.2 mL/bird, $10^6$ CFU/mL) every 24 hours for 4 consecutive days via gavage feeding using 20 ga×1.5 inch animal feeding needle (Fine Science Tools, Foster City, Calif., USA). Chickens were grouped and treated as shown in Table 4. Each group contained at least 6 chickens.

TABLE 4

Leghorn chicken groups subjected to inoculation and antibiotic administration treatments.

| Group | Pre-AR inoculation L. crispatus inocula | $bla_{CMY-2}^+$ E. coli inocula | Pre-antibiotic L. crispatus inocula | Amp (30 mg/kg) | Pre-AR inoculation L. crispatus inocula |
|---|---|---|---|---|---|
| Lc-Saline | + | + | — | — | — |
| Saline-saline | — | + | — | — | — |
| Lc-Amp | — | + | + | + | — |
| Saline-Amp | — | + | — | + | — |
| Amp-Lc | — | + | — | + | + |
| Amp-Saline | — | + | — | + | — |

—: saline administered at same column.
LC: *Lactobacillus crispatus* CG-12.
Amp: ampicillin.

Sample collection. Fresh feces were collected from each chicken on-site in the rearing facility. Fecal samples were collected at the 1st and last day of *Lactobacillus* inoculation, once a day during the antibiotic administration period, and once every three days during antibiotic withdrawal period up to 14 days from initial antibiotic exposure.

DNA extraction. Total DNA from chicken fecal samples for real-time quantitative PCR (qPCR) and denaturing gradient gel electrophoresis (DGGE) analyses were extracted according to a published method (Yu and Morrison 2004).

Real-time quantitative PCR. TaqMan real-time PCR protocol was used to assess $bla_{CMY-2}$ and 16S rRNA gene pools in total DNA extracted from chicken fecal samples, as described previously (Zhang et al., 2013). The sequences of the primers were 5'-GCCGTTGATGATCGAATC-3' (SEQ ID NO: 7) and 5'-GCGTATTGGCGATATGTAC-3' (SEQ ID NO: 8), with $bla_{CMY-2}$ probe 5'-6FAM AGTTCAG-CATCTCCCAGCCTAATCC-BHQ1-3' (SEQ ID NO: 9) (Zhang et al., 2013). The primers were synthesized by Sigma-Aldrich (St. Louis, Mo., USA), and the probe was synthesized by Biosearch Technology Inc. (Novato, Calif., USA). Each sample was assessed and analyzed in duplicates on a CFX96 system (Bio-Rad, Hercules, Calif., USA).

DGGE analysis. The 16S rRNA V3 region was used for amplification of partial 16S rRNA gene following a published procedure (Muyzer et al., 1993). The sequences of PCR primers used were 16S-357F-GC and 16S-518R; products were loaded on to an 8% acrylamide gel with a urea gradient from 40% to 60%. Electrophoresis was performed at 60° C., 83 V for 16 h using the Dcode system for DGGE (Bio-Rad, Hercules, Calif., USA). The finishing gel was stained with 0.01% ethidium bromide and imaged under ChemiDoc XRS system (Bio-Rad, Hercules, Calif., USA).

For analysis of the impact of Lactobacillus crispatus CG-12 on AR establishment (Day 5) and $bla_{CMY-2}^+$ colonization in GI microbiota (Day 9), and fecal DNA of 6 chickens from Saline-Saline group (SS1-SS6), 4 chickens from the Lc-Saline group (LS1-LS4) and 1 control subject (C) at Day 5 post-hatch were used as the template to amplify the 16S rRNA gene V3 region.

To analyze the predominant bacterial population in GI microbiota after antibiotic administration, chickens orally administered 30 mg/kg body weight/day Amp were used as the template to amplify the 16S rRNA gene V3 region. The fecal DNA of 4 chickens from Lc-Amp group (LA1-LA4), 4 chickens from Saline-Amp group (SA1-SA4) were used as templates to amplify the 16S rRNA gene V3 region.

16S Metagenomic Analysis. For microbiota analysis, three chickens were randomly selected from group Amp-Lc and Amp-Saline. Fecal DNA of Day 25 and Day 28 from each chicken was subjected to analysis. The V3/V4 portion of the 16S rRNA gene of the subjects were amplified by PCR following the standard protocol of 16S Metagenomic Sequencing Library Preparation (Illumina support, 2013), and the products were sequenced on an Illumina Miseq sequencer at OARDC Molecular and Cellular Image Center. Paired-end joining and quality filtering were performed with Qiime (Caporaso et al., 2010). Only sequences longer than 450 bp with Phred quality score higher than 19 were used for phylotype analysis. Operational Taxonomic Units (OTUs) were picked using an open-reference OTU picking process with 97% sequence similarity. 10% of the sequences that failed to hit the reference database were subjected to de novo clustering. Other quality control perimeters were set as default. Phylogenetic analysis and taxonomic assignments of the V3 and V4 portion of the 16S rRNA gene were made using Greengenes database (version 13_8). Additional phylotype comparisons and analysis were performed with the QIIME diversity analyses module.

Statistics. One-way ANOVA analysis of the population size of AR gene pools was performed in SAS (version 9.4), to compare difference between the three batches of chickens. Significance was declared at $P<0.05$.

Results

Growth inhibition assessments. The supernatant of Lactobacillus crispatus CG-12 formed inhibition zones with 8-9 mm in diameters on all E. coli plates, while no inhibition zone of E. coli supernatant was observed on cultured plates of Lactobacillus crispatus CG-12 (Table 5).

TABLE 5

The growth of $bla_{CMY-2}^+$ E. coli (CFU/mL) in modulated MRS media.

| | % Supernatant | pH | CFU/mL | Log$_{10}$ (CFU/mL) |
|---|---|---|---|---|
| Control | 0 | 6.4 | $6.7 \times 10^8$ | 8.8 |
| 20% Supernatant | 20 | 5.3 | $5.7 \times 10^5$ | 5.8 |
| pH 5.3 | 0 | 5.3 | $2.7 \times 10^6$ | 6.4 |

TABLE 5-continued

The growth of $bla_{CMY-2}^+$ E. coli (CFU/mL) in modulated MRS media.

| | % Supernatant | pH | CFU/mL | Log$_{10}$ (CFU/mL) |
|---|---|---|---|---|
| 40% Supernatant | 40 | 4.6 | <10 | <1 |
| pH 4.6 | 0 | 4.6 | $7.8 \times 10^2$ | 2.9 |
| 50% Supernatant | 50 | 4.4 | <10 | <1 |
| pH 4.4 | 0 | 4.4 | <10 | <1 |

CFU: colony forming unit

In the 0% supernatant-modified media, the overnight culture of E. coli had a total count of 8.8 log$_{10}$ CFU/mL. The 20% supernatant supplement reduced the E. coli count by 3 logs, ending with 5.8 log$_{10}$ CFU/mL. The corresponding 1×MRS (pH 5.0) had 6.4 log$_{10}$ CFU/mL of E. coli. With 40% supernatant, less than 1 log$_{10}$ CFU/mL was detected in the supernatant-modified media, while 2.9 log$_{10}$ CFU/mL was observed in the corresponding pH-modified media.

Early colonization of Lactobacillis crispatus and reduced AR gene pool in GI tract of chickens. Six chickens from the Saline-Saline group, four chickens from the Lc-Saline group and one free of any treatment were randomly picked to study the constitution of gut microbiota. DGGE analysis showed Lactobacillus crispatus was among the most predominant populations at Day 5 post-hatch, regardless of Lactobacillus crispatus CG-12 inocula (FIG. 1).

The $bla_{CMY-2}$ gene pool and 16S rRNA pool were analyzed via qPCR. Seven chickens from the Saline-saline group and eight from the Lc-Saline group were subjected to assessment. The ratio of $bla_{CMY-2}$ copies to 16S rRNA copies was calculated [($bla_{CMY-2}$/16S) %] to show the prevalence of $bla_{CMY-2}$ in the total bacterial load. In the Saline-Saline group, 6 out of 7 chickens had a ($bla_{CMY-2}$/16S) % ratio larger than 0.77, with only one exception (0.12). There were two subjects in this group that had an extremely high prevalence of the $bla_{CMY-2}$ gene, accounting for 7.14% and 54.96% of the total 16S copies. In the Lc-Saline groups, however, the ($bla_{CMY-2}$/16S) % ratio was generally low in all subjects: A ($bla_{CMY-2}$/16S) % ratio lower than 0.20 was detected in 7 out of 8 subjects; the highest one was 0.55, which was still lower than the average ratio in the Saline-Saline group.

Figure 2:
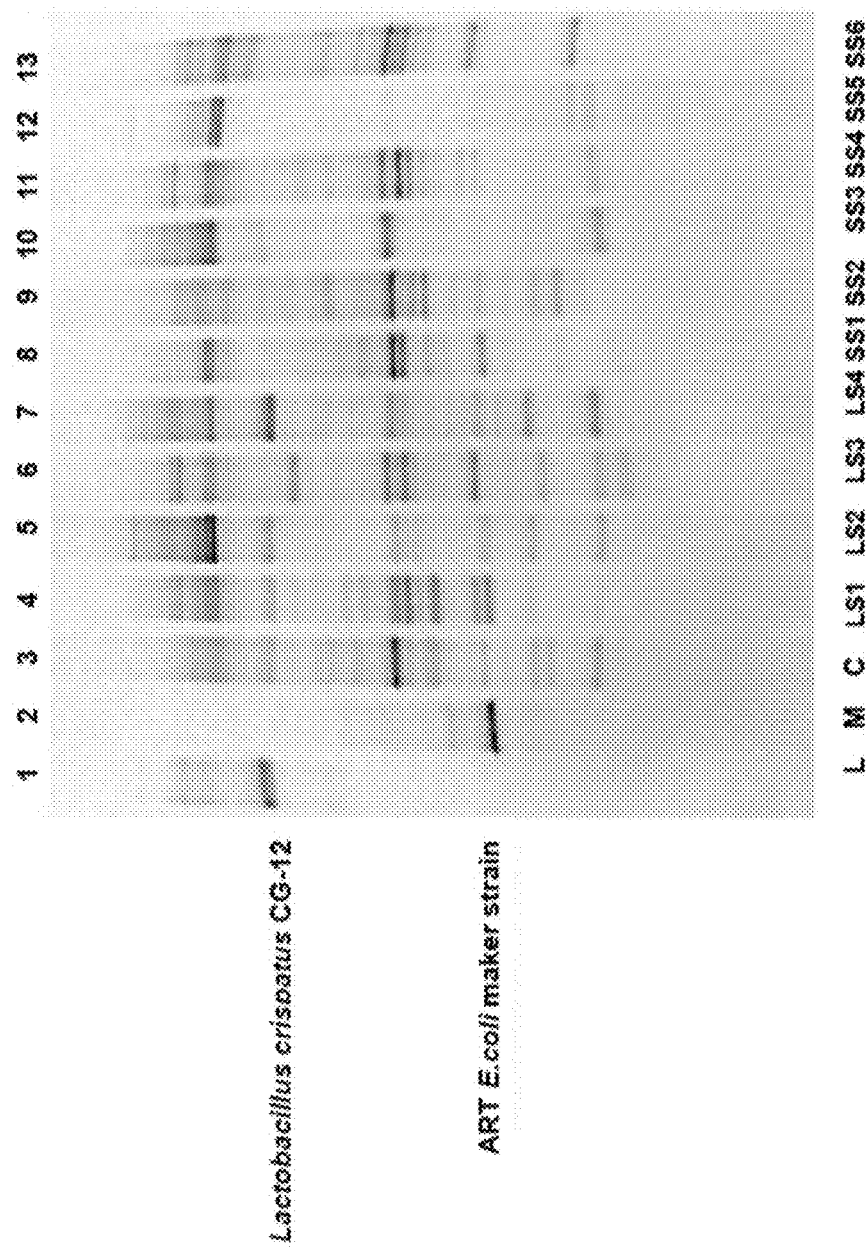
FIG. 2 is an image showing predominant 16S rRNA genes in total fecal DNA from chicken after 4 days of inoculation with $bla_{CMY-2}$+*E. coli* following *lactobacillus* inocula. Lane 1: *Lactobacillus crispatus* WZ-12; Lane 2: $bla_{CMY-2}$+*E. coli* marker strain. Lane 3: sample from control group; Lane 4-7: 4 individual samples from Lc-Saline group; Lane 8-13: 6 individual samples from Saline-Saline group.

Insignificant inhibition of the colonization of $bla_{CMY-2}^+$ marker strains. In the preliminary study, six chickens from the Saline-Saline group, four chickens from the Lc-Saline group and one free of any treatment were randomly picked to study the constitution of gut microbiota on Day 9, right after inoculation with $bla_{CMY-2}^+$ E. coli. DGGE analysis showed the Lactobacillus crispatus population was better maintained in the Lc-Saline group, but colonization of $bla_{CMY-2}^+$ E. coli was not affected by pre-inoculation with the Lactobacillus strain (FIG. 2). The AR gene pool increased from 8.8±0.3 log$_{10}$ (gene copies/g) to 9.9±0.6 log$_{10}$ (gene copies/g) in the Saline-Saline group, and from 8.2±0.2 log$_{10}$ (gene copies/g) to 9.8±1.0 log$_{10}$ (gene copies/g) in the Lc-Saline group. Overall, the $bla_{CMY-2}$ gene pool had about a 1 log increase from Day 5 to Day 9 regardless of inoculation with $bla_{CMY-2}^+$ E. coli, and the E. coli inocula did not significantly increase its prevalence in gut microbiota.

Insignificant reduction of AR gene pool during antibiotic treatment. Four chickens from the Saline-Amp group and eight from the Lc-Amp group were subjected to assessment of the $bla_{CMY-2}$ and 16S rRNA gene pool, to show the prevalence of the $bla_{CMY-2}$ gene on Day 21 (during treatment) and Day 25 (after treatment). A large prevalence of $bla_{CMY-2}$ gene pool was detected in both groups on Day 21: $bla_{CMY-2}$ and 16S rRNA gene pool was 8.7±0.8 $\log_{10}$ (gene copies/g) and 8.5±0.7 $\log_{10}$ (gene copies/g) in the Saline-Amp group. In the Lc-Amp group, $bla_{CMY-2}$ and 16S rRNA gene pool was 10.0±1.0 $\log_{10}$ (gene copies/g) and 9.2±1.07 $\log_{10}$ (gene copies/g). On Day 25, the $bla_{CMY-2}$ and 16S rRNA gene pools were 9.8±0.9 $\log_{10}$ (gene copies/g) and 10.5±1.0 $\log_{10}$ (gene copies/g), respectively the in Saline-Amp group; while in the Lc-Amp group, the $bla_{CMY-2}$ and 16S rRNA gene pools were 9.2±0.9 $\log_{10}$ (gene copies/g) and 10.4±0.8 $\log_{10}$ (gene copies/g), respectively. The overall prevalence of $bla_{CMY-2}$ decreased from Day 21 to Day 25, but no significant difference was observed between these two treatment groups.

Figure 3A:
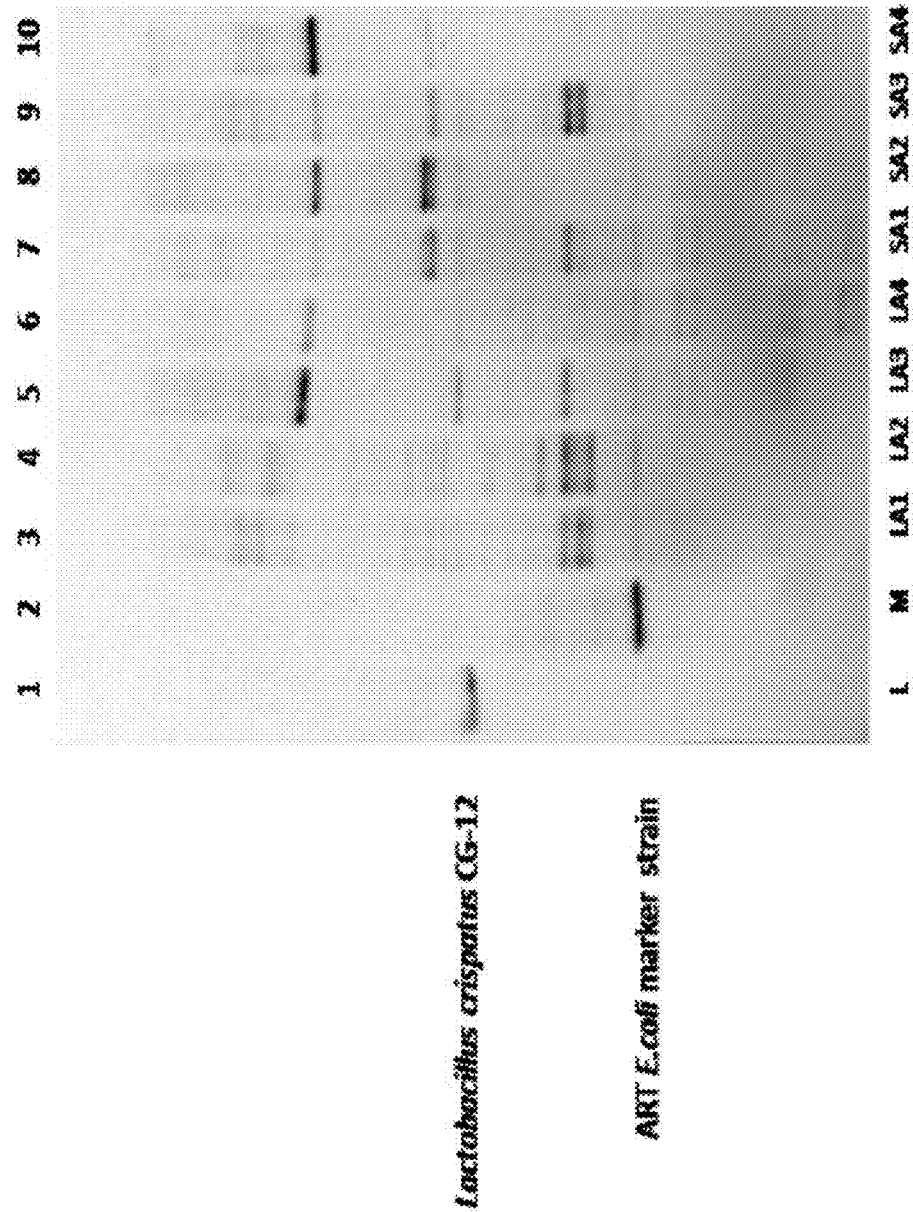
FIG. 3A-C are images showing predominant bacterial population in chicken GI microbiota before, during and after antibiotic administration. The predominant GI bacterial population is shown for Day 20 before antibiotic treatment (FIG. 3A); on Day 21 during antibiotic treatment (FIG. 3B); and on Day 25 after antibiotic treatment (FIG. 3C). For each of FIG. 3A-3C, Lane 1: *Lactobacillus crispatus* WZ-12; Lane 2: $bla_{CMY-2}$+*E. coli* marker cocktail; Lane 3-6: 4 individual samples from Lc-Amp group; Lane 7-10: 4 individual samples from Saline-Amp group.
Figure 3B:
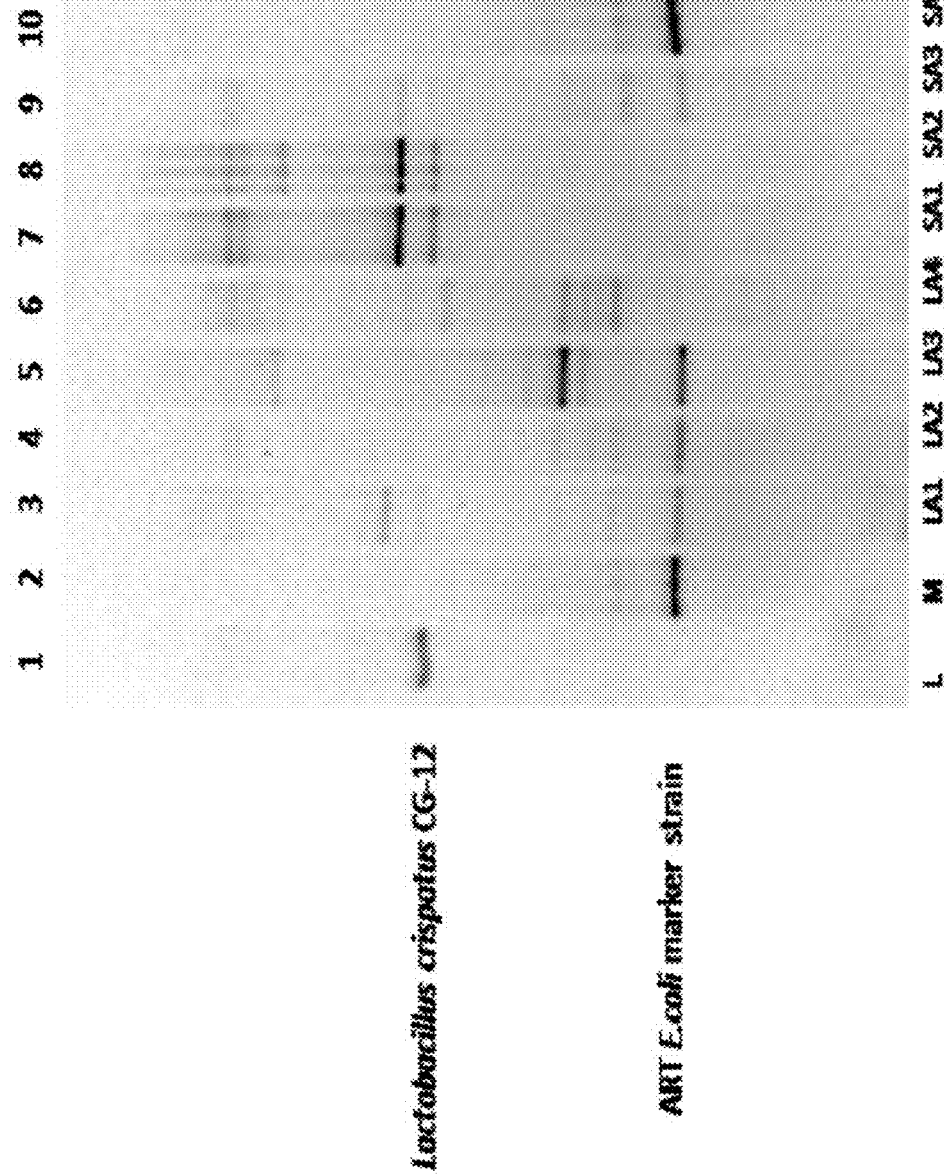
Figure 3C:
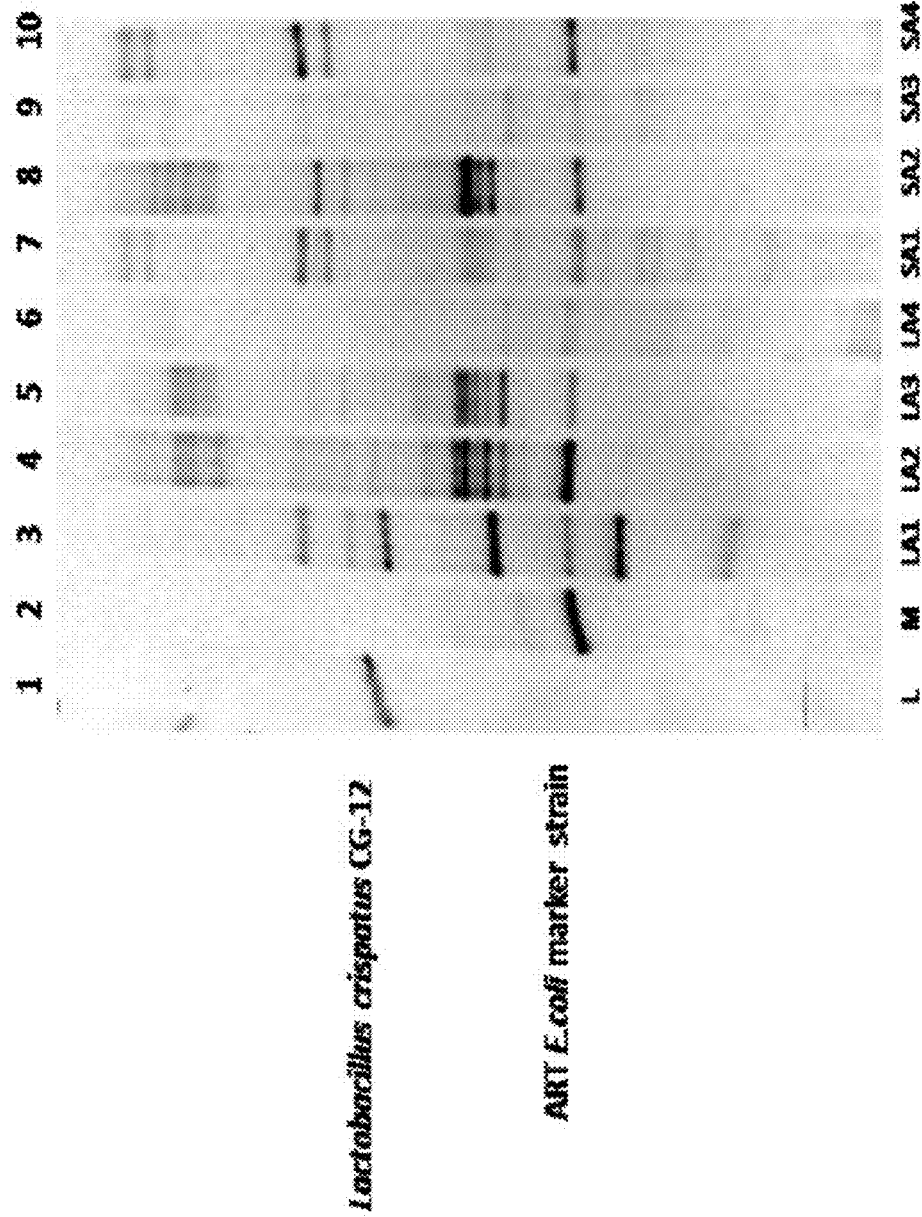

The predominance of the $bla_{CMY-2}{}^+E.\ coli$ marker was not reduced by pre-antibiotic inoculation with *Lactobacillus crispatus* CG-12 (FIG. 3A-3C). The selective enrichment of *E. coli* on Day 21 was more significant in the Lc-Amp group (FIG. 3B).

A possible explanation for these results is that because *Lactobacillus crispatus* CG-12 was susceptible to Amp, this strain may have been selectively eliminated during antibiotic treatment and therefore made no contribution in the treatment groups.

Figure 4:
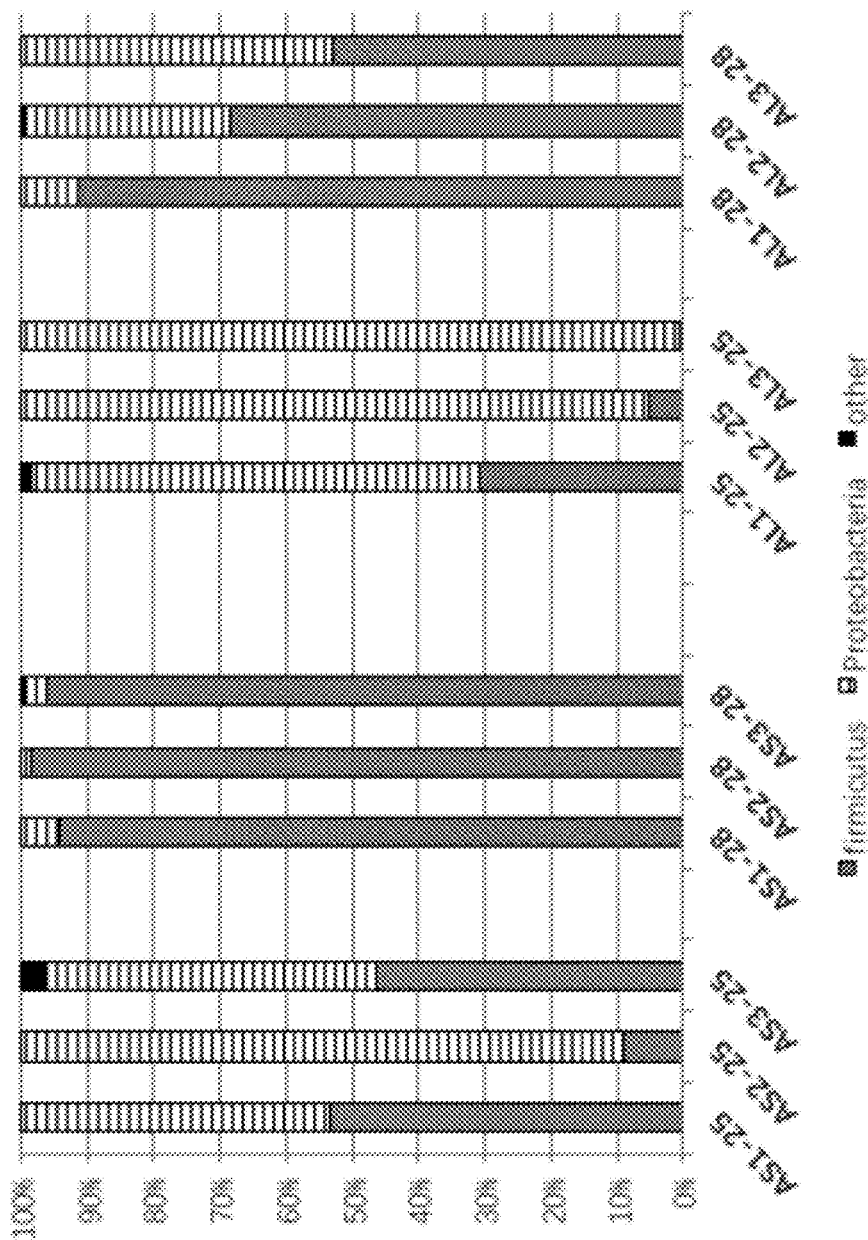
FIG. 4 is a graph showing the phylum distribution of GI microbiota at post-antibiotic treatment. Firmicutus and proteobacteria comprised the largest groups of GI microbiota, although other bacterial species not within these two groups were identified. Sets of columns on the left and second from left: 3 samples from Amp-Saline (AS) group on Day 25 (left) and Day 28 (second from left). Sets of columns third and fourth from the left: 3 samples from Amp-Lc (AL) group on Day 25 (third from left) and Day 28 (fourth from left).

The post-antibiotic change of microbiota constitution. Three randomly selected chickens from the Amp-Lc and the Amp-Saline groups were subjected to 16S rRNA phylotyping analysis to illustrate the impact of post-antibiotic inoculation of *Lactobacillus crispatus* CG-12 (FIG. 4).

Discussion and Conclusion

The bacteria competition test showed that *Lactobacillus crispatus* CG-12 has good in vitro inhibition capabilities against $bla_{CMY-2}{}^+E.\ coli$. Inhibition was largely due to the ability of CG-12 to produce lactic acid and reduce the pH, as media modified to have the same pH exhibited similar growth inhibition. Except for lactic acid, *Lactobacillus crispatus* CG-12 may also produce other inhibitory substances which contribute to the reduction of *E. coli* in 20% and 40% supernatant-modified media compared to corresponding pH-modified media.

The in vivo colonization of *Lactobacillus crispatus* CG-12 against $bla_{CMY-2}{}^+E.\ coli$ was further evaluated in poultry GI microbiota. *Lactobacillus crispatus* CG-12 is a commensal bacterial species isolated from chicken GI microbiota, which has good colonization fitness in chicken gut. Analysis of the constitution of GI microbiota on Day 5 shown that *Lactobacillus crispatus* was the predominate population at early chicken growth stages, in agreement with previous isolate-based research (Lu et al., 2003). The predominance implied a favored environment for *Lactobacillus crispatus* in chicken GI tracts at this stage of growth. The decrease in the $bla_{CMY-2}$ gene pool indicated successful colonization of $bla_{CMY-2}{}^-$ *Lactobacillus crispatus* CG-12 in the GI microbiota. It is possible that well-colonized $bla_{CMY-2}{}^-$ *Lactobacillus crispatus* CG-12 compete with homogeneous and heterogeneous bacteria and contribute to a reduction of AR bacteria and AR genes.

*Lactobacillus crispatus* lost its prevalence during chicken maturation, and other *Lactobacillus* and Firmicutes population become dominant during the natural transition of GI microbiota (Lu et al., 2003). The ineffectiveness of *Lactobacillus crispatus* CG-12 to reduce the AR gene pool and AR bacteria during Weeks 2-3 may be due to loss of predominance in the GI microbiota. As *Lactobacillus crispatus* CG-12 was susceptible to ampicillin, it was also likely selectively eliminated by antibiotic treatments in Week 4. Furthermore, the targeted AR bacterial *E. coli* strains were distantly related to *Lactobacillus crispatus* CG-12. The *E. coli* strains may locate in distant niches in the gut, making it more difficult for *Lactobacillus crispatus* CG-12 to eliminate. Early studies on displacement of indigenous AR *E. coli* were achieved by using susceptible strains from the same species (Linton et al., 1978). Future trials to use commensal or probiotic stains for clonal decontamination should take into consideration the ecological position of the targeted strains.

The constitution of GI microbiota recovered fast once the antibiotic selective pressure was removed. The dominance of Firmicutes recovered within three days without any intervention. Inoculation of *Lactobacillus crispatus* CG-12 did not accelerate recovery; rather the prevalence of Proteobacteria was even higher in the inoculated group.

In conclusion, inoculation of *Lactobacillus crispatus* CG-12 is a promising strategy to reduce early colonization of AR in chicken GI microbiota.

Example 3

Competition Test Against Resistant *Escherichia coli* Strains

Four previously identified $Amp^r$ (ESBL) *Escherichia coli* strains were introduced to the study to serve as antibiotic resistant bacteria marker, including strain M9-1 (CA-1 previously), M9-4 (CA-4), M9-12 (CA-20) and 933-36, all were previously recovered from poultry, identified with high MIC (>256 µg/mL) and were found to grow well in MRS broth. The competence of probiotic strains against these $Amp^r$ *Escherichia coli* strains was examined with the following set up, 1) a quantity of $10^5$ cells from one probiotic strain is inoculated with $10^5$ or $10^6$ cells of one $Amp^r$ *Escherichia coli* strain (ratio of 1:1 and 1:10) in MRS broth and then incubated at 37° C. for 24 hours. The culture was then recovered and inoculated on MRS agar supplemented with 32 µg/mL ampicillin and then incubated anaerobically at 37° C. for 48 hours. The growth performance of isolates on the agar was recorded. A complete inhibition is defined as absolutely no growth on the MRS agar supplemented with ampicillin (designated as "I"). A partial inhibition is defined as attenuated growth of $Amp^r$ *Escherichia coli* strain on the MRS agar (designated as "P"). No inhibition is defined as complete growth of $Amp^r$ *Escherichia coli* strain on the MRS agar (designated as "N"). The competition test result is included in Table 6.

TABLE 6

Competition test between probiotic strains and $Amp^r$ (ESBL) *Escherichia coli* strains

| | M9-1(CA-1) | | M9-4 (CA-4) | | M9-12(CA-20) | | 933-36 | |
|---|---|---|---|---|---|---|---|---|
| | 1:1 | 1:10 | 1:1 | 1:10 | 1:1 | 1:10 | 1:1 | 1:10 |
| 1-1 | P | N | N | N | N | N/A | N | N |
| 1-3 | P | N | N | N | N | N/A | N | N |
| 1-9 | P | N | N | N | N | N/A | N | N |
| 1-14 | I, c | I, c | I, c | I, c | I, s | N/A | I, s | I, c |
| 1-22 | N | N | P | N | N | N/A | N | N |
| 1-31 | P | N | I, s | I, s | I, s | N/A | I, s | N |
| 1-35 | P | N | P | N | N | N/A | N | N |
| 2-2 | I, c | N | I, c | I, s | I, c | N/A | I, c | N |
| 2-26 | P | N | P | N | N | N/A | N | N |

In addition, some inhibition effect can be divided as bacteriostatic effect (designated with "s") and bactericidal effect (designated with "c"), with bacteriostatic effect defined as significant recovery of $Amp^r$ *Escherichia coli* strain on MRS agar supplemented with ampicillin after a week of shelf storage; while bactericidal effect defined as no recovery of Amp$^r$ *Escherichia coli* strain under the same conditions.

In summary, besides CG-12 (now designated as WZ-12), three more LAB strains, 1-14, 1-31, and 2-2, especially exhibited a broad spectrum inhibition to the multidrug resistant *E. coli* strains tested.

Example 4

Genome Sequencing of Isolates.

In addition to CG-12 (now designated as WZ-12), 16S rRNA sequencing further identified three probiotic strains. Two of strains were *Lactobacillus salivarius* (1-14) and *Lactobacillus reuteri* (2-2). The third strain turned out to be *Streptococcus alactolyticus*. Previous literatures illustrated the application of *Lactobacillus salivarius* CTC2197, as well as certain strains of *Lb. reuteri* and *Streptococcus alactolyticus* as probiotics to inhibit certain foodborne pathogens in poultry, and mostly in swine.

To further validate the novelty of our isolates, two of the *Lactobacillus* strains were further subjected to full genome sequencing for genetic identification to clear up the background for potential patenting as backup strains for CG-12 (WZ-12). The genome accession numbers for the three probiotic strains used in this study include: OSU_LbSal_1.14", accession number QOZV00000000; "OSU_LbReu_2.2_v1", accession number QOWD00000000; and WZ-12 (previously CG-12, 721-12), accession number QKVQ00000000.

Animal Studies. The probiotics as disclosed herein were applied to chickens raised in a poultry facility, with the aim to examine the effectiveness of the treatment phenotypically and genetically (fecal microbiota) and physiologically (chickens); and to adjust receipt and procedure of feeding if necessary.

Figures 5A, 5B:
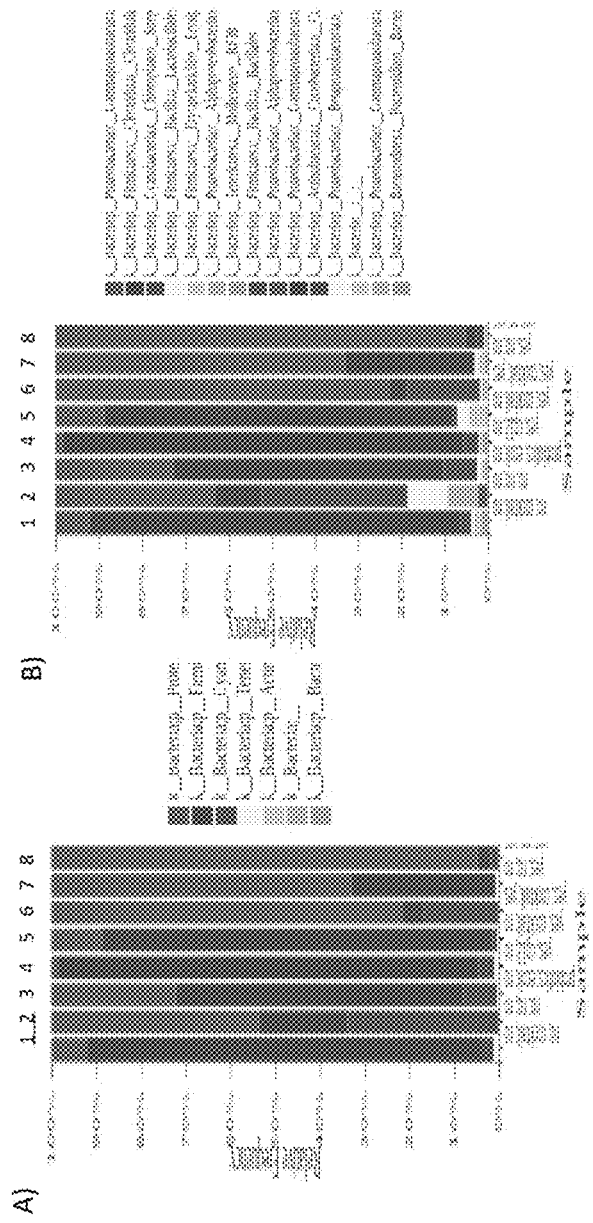
FIGS. 5A and 5B show the impact of probiotic treatment on bacterial population in pooled feces of chickens.
Figures 6A, 6B:
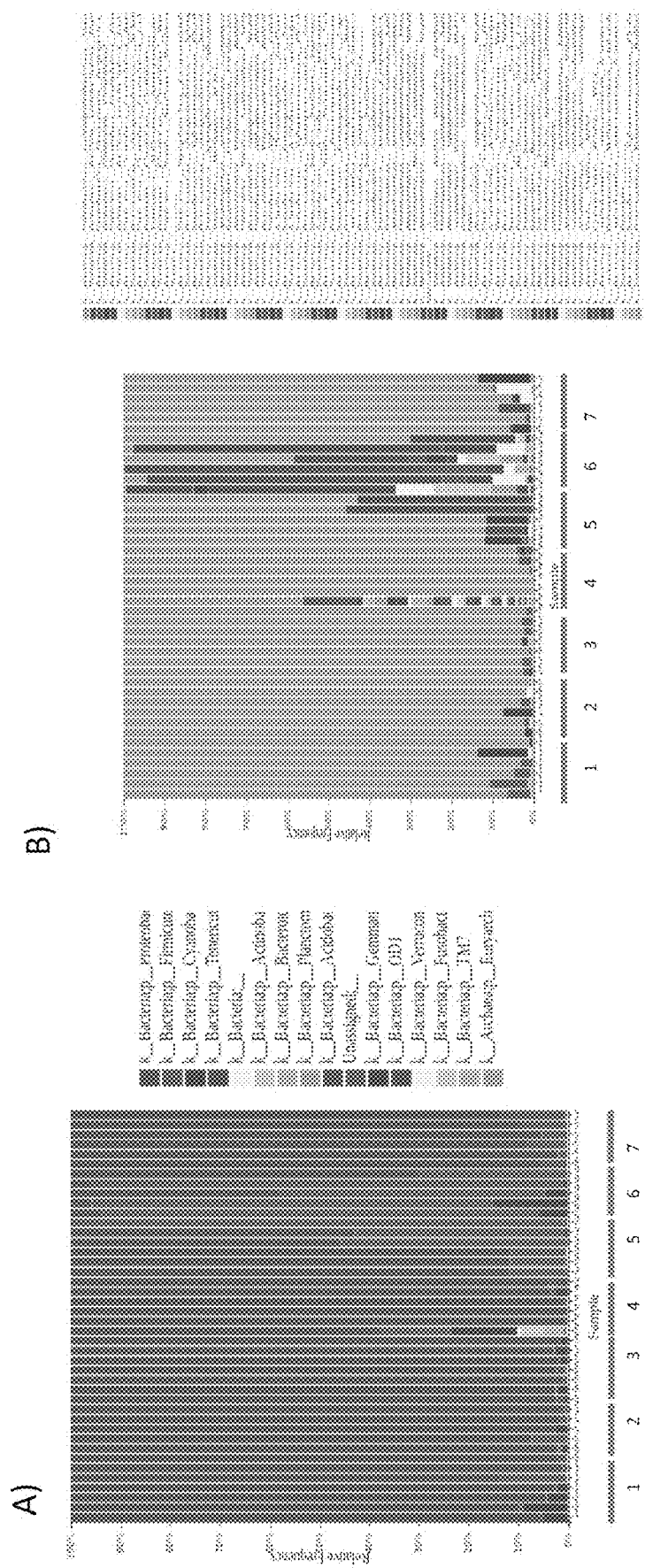
FIGS. 6A and 6B show probiotics and ESBL inoculation on the profiles of poultry fecal microbiota followed by oral or injective antibiotic treatment.

Treatments effective in modulating gut microbiota. The metagenomics assessment #1 (FIGS. 5A and B) illustrated bacterial population in pooled feces of chickens treated with ESBL *E. coli* with or without probiotic protection, without antibiotic applications. The results suggested that without any inoculation, proteobacteria (gram-negative bacteria including *E. coli* etc.), Cynobacteria and Firmicutes were the dominant population (FIG. 5A, Lane 2). Feeding probiotics cocktail (*Lb. crispatus* WZ12, *Lb. salivarius* 1-14 and *Lb. reuteri* 2-2) made Firmicutes (the phylum including Bacilli, Clostridia etc., such as *Lactobacillus*) the absolute dominant population in fecal microbiota (FIG. 5A, Lane 1), significantly reduced Proteobacteria (including previously inoculated *E. coli*) in the poultry fecal/gut microbiota. Inoculating *Lactobacillus* probiotic cocktail before exposure to ESBL *E. coli* also reduced the amount of (colonization of) Proteobacteria in fecal microbiota (Lane 3). *Lb. crispatus* CG 12 (renamed to WZ12) also was effective in reducing previously inoculated *E. coli* and made Firmicutes the dominant population (Lane 4). Probiotic cocktail given after *E. coli* exposure was also effective in reducing the previously colonized *E. coli* population (Lane 5). Tween 80 treatment assisted the colonization of Proteobacteria but not the Firmicutes. So in summary, the inoculation of the *Lactobacillus* probiotics significantly helped with preventing and reducing Proteobacteria.

It was recognized that even if antibiotic resistant bacteria may be reduced by probiotic treatment, some of those resistant bacteria seeds might still retain in the microbiota, and could pop up again when exposed to antibiotics. Therefore in another set of the experiment, following probiotic and ESBL *E. coli* exposure, the chickens were further treated with Amp by oral or muscle injection. As illustrated in FIG. 7, ESBL *E. coli* seed dominated the fecal microbiota after oral Amp treatment. But Probiotic treated chickens (Group 1 &2) retained more Firmicutes or Cynobacteria than chickens without probiotic treatment (Group 3 with inoculated ESBL *E. coli* & Group 4 natural flora, with one outlier). Despite Firmicutes or Cynobacteria were still a minor population in Group 1 & 2 compared to Proteobacteria, the saved diversify seeds enable better recovery once the antibiotic selective pressure was removed. Furthermore, changing antibiotic administration from oral to injection made significant difference in retaining Firmicutes with (Group 7) or without ESBL *E. coli* inoculation (Group 5).

In conclusion, by changing antibiotic treatment from oral to injection, feeding probiotics and manipulating ways of probiotic administration, ESBL *E. coli* can be significantly reduced in fecal microbiota and protect gut microbiota diversity in poultry.

Example 5

Figures 7A, 7B:
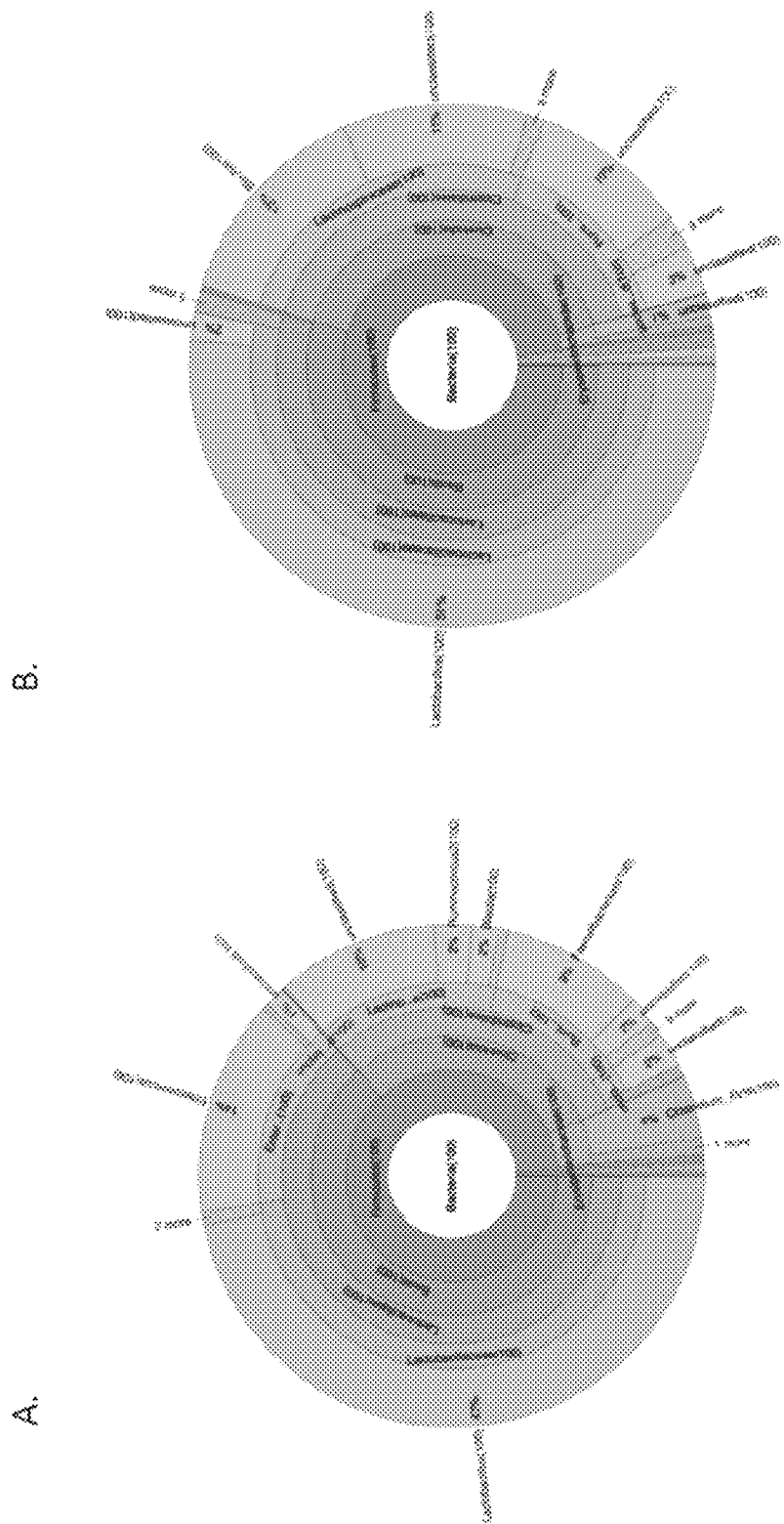
Figure 7E:
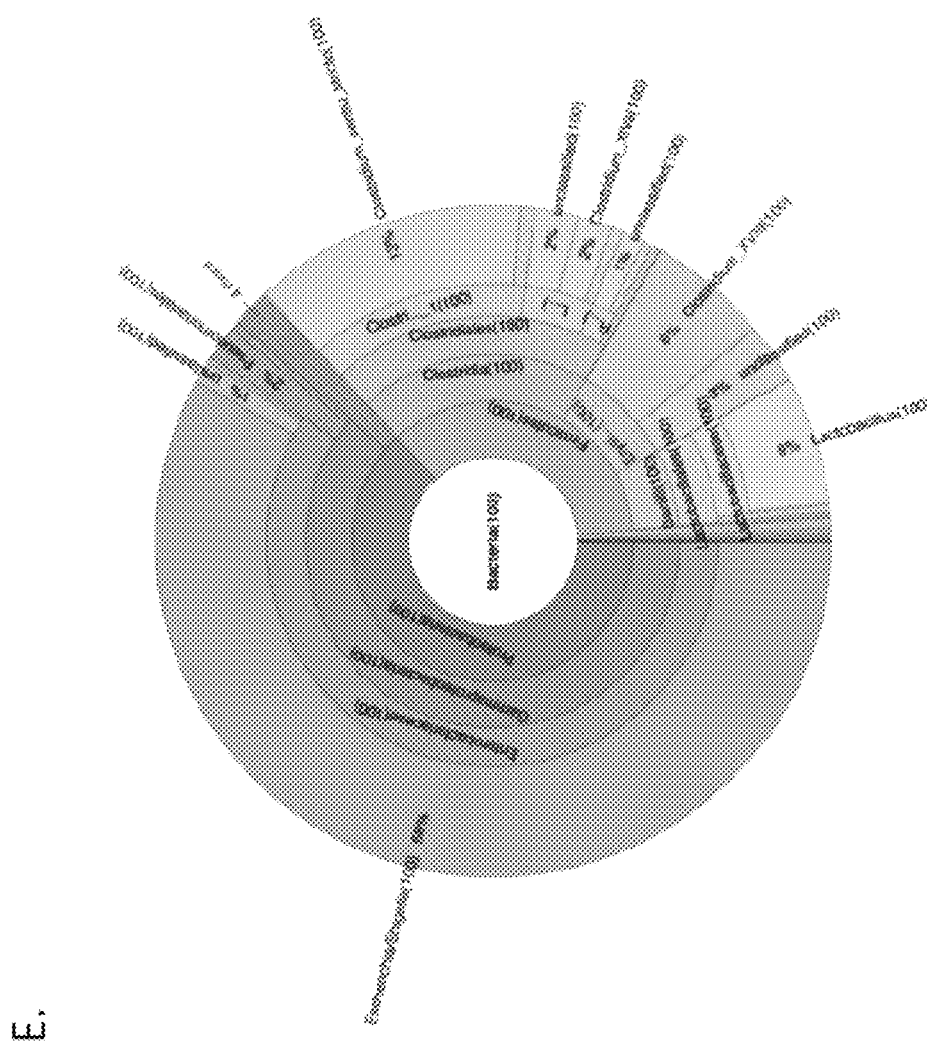

The impact of ampicillin administration routes and inoculation of Amp$^r$ *E. coli* on poultry gut microbiota. FIG. 7A-B illustrates the impact of ampicillin application on gut microbiota of chickens. The data illustrated that without antibiotic application (FIG. 7A), *Lactobacillus* dominant, *E. coli/Shegilla* insignificant. Without inoculation of the "bully" *E. coli* M 9-4 cocktail, given ampicillin by muscle injection led to minimal changes (FIG. 7B), but by oral ampicillin led to decrease of Firmicutes (still dominant) and significant increase of Proteobacteria, but within Proteobacteria only small amount due to *E. coli/Shegilla*, mostly due to *Klebsiella* (FIG. 7C). In chickens inoculated with the "bully" *E. coli* cocktail, if Amp was given by muscle injection, Firmicutes still dominant but with which *Lactobacillus* drastically reduced, and *Clostridium* et al. quickly increased (FIG. 7D); if Amp was given by oral feeding, then Firmicutes changed from dominant to minority, and Proteobacteria, within which *E. coli/Shegilla* became dominant (FIG. 7E). The results clearly illustrated the major impact on oral ampicillin administration on poultry gut microbiota by diminishing *Lactobacillus*, increasing *Clostridium*, and massively increase Firmicutes due to Amp$^r$ *E. coli* in inoculated chickens and *Klebsiella* in non-inoculated chickens.

The Impact of *Lactobacillus/Streptococcus* probiotic cocktail feeding study on mice gut microbiota. In mice inoculated with Amp$^r$ *E. coli* and Tet$^r$ *Enterococcus* cocktail for 4 days followed by normal food and gavage saline, the Amp$^r$ population on LB plates, presumably being Amp$^r$ *E. coli*, were 82% (mouse 4R) and 90% (mouse 4N). If with Amp$^r$ *E. coli* and Tet$^r$ *Enterococcus* cocktail for 4 days followed by normal food and gavage feeding of probiotic cocktail instead of saline, the Amp$^r$ population on LB plates, presumably being Amp$^r$ *E.coli*, were 78% (Mouse 6L), 58% (6R) and 92% (6N). The 58% Amp$^r$ *E. coli* was the lowest detected so far, which strongly suggested the potential functionality of the probiotic cocktail in reducing the Amp$^r$ *E. coli* subpopulation. Still pending for the metagenomic fecal microbiota profiling data.

Molecular mechanism in the persistent "bully" Amp$^r$ *E. coli* strains. Plasmid extraction showed that the poultry oriented Amp$^r$ *E. coli* strains used in inoculation carry at least 3 plasmids. The Amp$^r$ phenotype was persistent even when the strains were cultivated in LB broth without ampicillin for many generations. Electroporation study and DNA sequencing data confirmed that the Amp$^r$ is encoded by a large plasmid, but the plasmid was stably retained in the host event with the corresponding antibiotic selective pressure. In a competition study, DH5α failed to overcome the "bully" Amp$^r$ E. coli strain. When the "bully" strain M9-4 was inoculated on the LB plate covered with DH5α, it showed clear inhibition zone for all three dilutions (FIG. 8A). The data illustrated that strain M9-4 is "bully" also because it carried mechanism to over-compete the other E. coli strains.

Second group of E. coli probiotic derivatives to combat the "bully" strains. By manipulating the DH5α with genetic elements, multiple DH5α derivatives M9-4-1 were received that are no longer inhibited (clear inhibition zone) by the "bully" strain M9-4 but with white growth ring (FIG. 8A-B). These new E. coli strains and derivatives can serve as the second group of probiotics, to be used in combination of the Lactobacillus/Streptococcus probiotics, to further over-compete towards eliminating the "bully" ESBL strains in food animal production.

REFERENCES

1. Aarestrup, F. M., Bager, F., Jensen, N. E., Madsen, M., Meyling, A., & Wegener, H. C. (1998). Resistance to antimicrobial agents used for animal therapy in pathogenic-, zoonotic- and indicator bacteria isolated from different food animals in Denmark: a baseline study for the Danish Integrated Antimicrobial Resistance Monitoring Programme (DANMAP). Apmis, 106(7-12), 745-770.
2. Adlerberth, I. & Wold, A. E. (2009). Establishment of the gut microbiota in Western infants. Acta paediatrica. 98(2): 229-38
3. Ahmed, N. A., Petersen, F. C., & Scheie, A. A. (2009). AI-2/LuxS is involved in increased biofilm formation by Streptococcus intermedius in the presence of antibiotics. Antimicrobial agents and chemotherapy, 53(10): 4258-4263.
4. Akpan, M. R., Ahmad, R., Shebl, N. A., & Ashiru-Oredope, D. (2016). A Review of Quality Measures for Assessing the Impact of Antimicrobial Stewardship Programs in Hospitals. Antibiotics, 5(1), 5.
5. Alanis, A. J. (2005). Resistance to antibiotics: are we in the post-antibiotic era? Archives of Medical Research. 36(6): 697-705.
6. AlFaleh, K., & Anabrees, J. (2014). Probiotics for prevention of necrotizing enterocolitis in preterm infants. Evidence-Based Child Health: A Cochrane Review Journal, 9(3), 584-671.
7. Allen, H. K., Donato, J., Wang, H. H., Cloud-Hansen, K. A., Davies, J., & Handelsman, J. (2010). Call of the wild: antibiotic resistance genes in natural environments. Nature Reviews Microbiology, 8(4), 251-259.
8. Allignet, J., Loncle, V., & El Solh, N. (1992). Sequence of a staphylococcal plasmid gene, vga, encoding a putative ATP-binding protein involved in resistance to virginiamycin A-like antibiotics. Gene, 117(1), 45-51.
9. Alonso-Hernando, A., Prieto, M., Garcia-Fernandez, C., Alonso-Calleja, C., & Capita, R. (2012). Increase over time in the prevalence of multiple antibiotic resistance among isolates of Listeria monocytogenes from poultry in Spain. Food Control, 23(1), 37-41.
10. Aminov, R. I. (2010). A brief history of the antibiotic era: lessons learned and challenges for the future. Frontiers in microbiology, 1.
11. Amit-romach E, Sklan D and Unil Z. (2004) Microflora ecology of the chicken intestine using 16S ribosomal DNA primers. Poultry Science, 83: 1093-1098
12. Anadon, A., Martinez-Larrañaga, M. R., Diaz, M. J., Bringas, P., Fernandez, M. C., Fernandez-Cruz, M. L., . . . & Martinez, M. A. (1994). Pharmacokinetics of doxycycline in broiler chickens. Avian pathology, 23(1), 79-90.
13. Antunes, P., Machado, J., Sousa, J. C., & Peixe, L. (2005). Dissemination of sulfonamide resistance genes (sul1, sul2, and sul3) in Portuguese Salmonella enterica strains and relation with integrons. Antimicrobial agents and chemotherapy, 49(2), 836-839.
14. Antunes, P., Réu, C., Sousa, J. C., Peixe, L., & Pestana, N. (2003). Incidence of Salmonella from poultry products and their susceptibility to antimicrobial agents. International journal of food microbiology, 82(2), 97-103.
15. Apajalahti, J. H., Kettunen, A. A., Bedford, M. R. & Holben, W. E. (2001). Percent G-C profiling accurately reveals diet-related differences in the gastrointestinal microbial community of broiler chickens. Applied Environmental Microbiology, 67:5656-5667.
16. Asahara, T., Shimizu, K., Nomoto, K., Hamabata, T., Ozawa, A., & Takeda, Y. (2004). Probiotic bifidobacteria protect mice from lethal infection with Shiga toxin-producing Escherichia coli O157: H7. Infection and immunity, 72(4), 2240-2247.
17. Ashraf, R., & Shah, N. P. (2014). Immune system stimulation by probiotic microorganisms. Critical reviews in food science and nutrition, 54(7), 938-956.
18. Avorn, J., Barrett, J., Davey, P., McEwen, S., O'Brien, T. & Levy, S. (2001). Antibiotic resistance: synthesis of recommendations by expert policy groups. Geneva: World Health Organization.
19. Aziz, R. K, Bartels D., Best, A. A., DeJongh, M., Disz, T., Edwards, R. A., Formsma, K., Gerdes, S., Glass, E. M., Kubal, M. & Meyer, F. (2008). The RAST Server: rapid annotations using subsystems technology. BMC genomics, 9(1), 1.
20. Bager, F., Madsen, M., Christensen, J. & Aarestrup, F. M. (1997). Avoparcin used as a growth promoter is associated with the occurrence of vancomycin-resistant Enterococcus faecium on Danish poultry and pig farms. Preventive veterinary medicine, 31(1):95-112
21. Baquero, F., Coque, T. M. & de la Cruz, F. (2011). Ecology and evolution as targets: the need for novel eco-evo drugs and strategies to fight antibiotic resistance. Antimicrobial agents and chemotherapy, 55(8):3649-60.
22. Barnes, E. M., Impey, C. S., & Cooper, D. M. (1980). Manipulation of the crop and intestinal flora of the newly hatched chick. The American journal of clinical nutrition, 33(11), 2426-2433.
23. Barnes, E. M. (1979). The intestinal microflora of poultry and game birdsduring life and after storage. Journal of Applied Bacteriology, 46:407-419.
24. Barnes, E. M., Mead, G. C., Barnum, D. A. & Harry, E. G. (1972). The intestinal flora of the chicken in the period 2 to 6 weeks of age, with particular reference to the anaerobic bacteria. British Poultry Science, 13:311-326.
25. Barthelemy, P., Autissier, D., Gerbaud P., & Courvalin P. (1984). Enzymic hydrolysis of erythromycin by a strain of Escherichia coli. A new mechanism of resistance. Journal of Antibiotics (Tokyo), 37, 1692-1696
26. Baucheron, S., Nishino, K., Monchaux, I., Canepa, S., Maurel, M. C., Coste, F., Roussel A., Cloeckaert, A. & Giraud, E. (2014). Bile-mediated activation of the acrAB and tolC multidrug efflux genes occurs mainly through transcriptional derepression of ramA in Salmonella enterica serovar Typhimurium. Journal of Antimicrobial Chemotherapy, 69(9), 2400-2406.

27. Bauernfeind, A., Stemplinger, I., Jungwirth, R., Wilhelm, R., & Chong, Y. (1996). Comparative characterization of the cephamycinase blaCMY-1 gene and its relationship with other beta-lactamase genes. Antimicrobial agents and chemotherapy, 40(8), 1926-1930.

28. Beaber, J. W., Hochhut, B., & Waldor, M. K. (2004). SOS response promotes horizontal dissemination of antibiotic resistance genes. Nature, 427(6969), 72-74.

29. Beceiro, A., Llobet, E., Aranda, J., Bengoechea, J. A., Doumith, M., Hornsey, M., . . . & Woodford, N. (2011). Phosphoethanolamine modification of lipid A in colistin-resistant variants of *Acinetobacter baumannii* mediated by the pmrAB two-component regulatory system. Antimicrobial agents and chemotherapy, 55(7), 3370-3379.

30. Belongia, E. A., Knobloch, M. J., Kieke, B. A., Davis, J. P., Janette, C., & Besser, R. E. (2005). Impact of statewide program to promote appropriate antimicrobial drug use. Emerg Infect Dis, 11(6), 912-920.

31. Bennett, P. M. (2008). Plasmid encoded antibiotic resistance: acquisition and transfer of antibiotic resistance genes in bacteria. British journal of pharmacology, 153 (S1):S347-57.

32. Bensink, J. C., Botham, F. P. (1983). Antibiotic resistant coliform bacilli, isolated from freshly slaughtered poultry and from chilled poultry at retail outlets. Australian veterinary journal, 60(3): 80-83.

33. Bjarnsholt, T., van Gennip, M., Jakobsen, T. H., Christensen, L. D., Jensen, P. O. & Givskov, M. (2010). In vitro screens for quorum sensing inhibitors and in vivo confirmation of their effect. Nature protocols, 5(2):282-93;

34. Boehm, A., Steiner, S., Zaehringer, F., Casanova, A., Hamburger, F., Ritz, D., Keck, W., Achermaan, M., Schirner, T. & Jenal, U. (2009). Second messenger signalling governs *Escherichia coli* biofilm induction upon ribosomal stress. Molecular microbiology, 72(6), 1500-1516.

35. Boehr, D. D., Daigle, D., Wright, G. D., (2004) Domain—domain interactions in the aminoglycoside antibiotic resistance enzyme AAC (6'-APH(2"). Biochemistry, 43:9846-9855

36. Bonten, M. J., D. J. Austin, & M. Lipsitch. (2001). Understanding the spread of antibiotic resistant pathogens in hospitals: mathematical models as tools for control. Clinical Infectious Diseases, 33:1739-1746.

37. Bootsma, M. C., O. Diekmann, & M. J. Bonten. (2006). Controlling methicillin-resistant *Staphylococcus aureus*: quantifying the effects of interventions and rapid diagnostic testing. Proceedings of the National Academy of Sciences of the Unite States, 103:5620-5625.

38. Botsoglou, N. A., Fletouris, D. J. (2001) Drug Residues in Food. Marcel Dekker, Inc., New York, N.Y.

39. Boucher, H. W., Talbot, G. H., Bradley, J. S., Edwards, J. E., Gilbert, D., Rice, L. B., . . . & Bartlett, J. (2009). Bad bugs, no drugs: no ESKAPE! An update from the Infectious Diseases Society of America. Clinical Infectious Diseases, 48(1), 1-12.

40. Boudeau, J., Glasser, A. L., Julien, S., Colombel, J. F., & Darfeuille-Michaud, A. (2003). Inhibitory effect of probiotic *Escherichia coli* strain Nissle 1917 on adhesion to and invasion of intestinal epithelial cells by adherent—invasive *E. coli* strains isolated from patients with Crohn's disease. Alimentary pharmacology & therapeutics, 18(1), 45-56.

41. Bozdogan, B., Berrezouga, L., Kuo, M. S., Yurek, D. A., Farley, K. A., Stockman, B. J., & Leclercq, R. (1999). A new resistance gene, linB, conferring resistance to lincosamides by nucleotidylation in *Enterococcus faecium* HM1025. Antimicrobial agents and chemotherapy, 43(4), 925-929.

42. Brettin, T., Davis, J. J., Disz, T., Edwards, R. A., Gerdes, S., Olsen, G. J., . . . & Shukla, M. (2015). RASTtk: a modular and extensible implementation of the RAST algorithm for building custom annotation pipelines and annotating batches of genomes. Scientific reports, 5.

43. Brisbin, J. T., Gong, J. & Sharif, S. (2008). Interactions between commensal bacteria and the gut-associated immune system of the chicken[J]. Animal Health Research Reviews, 9(01): 101-110.

44. Brooks, J. P., McLaughlin, M. R., Scheffler, B., & Miles, D. M. (2010). Microbial and antibiotic resistant constituents associated with biological aerosols and poultry litter within a commercial poultry house. Science of the total environment, 408(20), 4770-4777.

45. Brown, S. A., & Riviere, J. E. (1991). Comparative pharmacokinetics of aminoglycoside antibiotics. Journal of Veterinary Pharmacology and Therapeutics, 14(1), 1-35.

46. Bryan, K. G., Harp, R. M., Lambert, B. D., Cadle, J. M., & Snider, W. G. (2015). The Effect of Supplemental Probiotics and Spray-Dried Egg Proteins on Piglet Growth Performance Characteristics. Texas Journal of Agriculture and Natural Resources, 28, 1-11.

47. Busse, H. J., C. Wostmann, and E. P. Bakker. 1992. The bactericidal action of streptomycin: membrane permeabilization caused by the insertion of mistranslated proteins into the cytoplasmic membrane of *Escherichia coli* and subsequent caging of the antibiotic inside the cells: degradation of these proteins.

48. Byarugaba, D. K. (2010). Mechanisms of antimicrobial resistance. InAntimicrobial Resistance in Developing Countries (pp. 15-26). Springer New York.

49. Cameron, F. H., Obbink, D. J. G., Ackerman, V. P., & Hall, R. M. (1986). Nucleotide sequence of the AAD (2') aminoglycoside adenylyltransferase determinant aadB. Evolutionary relationship of this region with those surrounding aadA in R538-1 and dhfrll in R388. Nucleic acids research, 14(21), 8625-8635.

50. Caporaso, J. G., Kuczynski, J., Stombaugh, J., Bittinger, K., Bushman, F. D., Costello, E. K., Fierer, N., Pena, A. G., Goodrich, J. K., Gordon, J. I., Huttley, G. A. (2010). QIIME allows analysis of high-throughput community sequencing data. Nature methods, 7(5):335-6.

51. Carattoli, A. (2011). Plasmids in Gram negatives: molecular typing of resistance plasmids. International Journal of Medical Microbiology, 301(8):654-8

52. Carattoli, A. (2013). Plasmids and the spread of resistance. International Journal of Medical Microbiology, 303(6):298-304.

53. Cardenas, A. M., & Palzkill, T. (2015). Beta-Lactam Resistance. Encyclopedia of Metagenomics: Environmental Metagenomics, 45-53.

54. Casewell, M., Friis, C., Marco, E., McMullin, P., & Phillips, I. (2003). The European ban on growth-promoting antibiotics and emerging consequences for human and animal health. Journal of antimicrobial chemotherapy, 52(2), 159-161.

55. Castanon, J. I. R. (2007). Review: History of the use of antibiotic as growth promoters in European poultry feeds. Poultry Science. 86: 2466-2471

56. Centers for Disease Control and Prevention (CDC). (2013). Antibiotic resistance *Centers for Disease Control and Prevention (CDC) Drug Resistance Threats* 2013 *PDF*, Accessed Jul. 15, 2016

57. Centers for Disease Control and Prevention (CDC). (2016) Get Smart: Know When Antibiotics Work.-Accessed Jul. 15, 2016.
58. Chambers, H. F., and M. A. Sande. (1995). Antimicrobial agents: the aminoglycosides, p. 1103-1121. In J. G. Hardman, L. E. Limbird, P. B. Molinoff, R. W. Ruddon, and A. Goodman Gilman (ed.), The pharmacological basis of therapeutics. McGraw-Hill, New York, N.Y.
59. Chopra, I., & Roberts, M. (2001). Tetracycline antibiotics: mode of action, applications, molecular biology, and epidemiology of bacterial resistance. Microbiology and molecular biology reviews, 65(2), 232-260.
60. Claverys, J. P., Prudhomme, M., & Martin, B. (2006). Induction of competence regulons as a general response to stress in gram-positive bacteria. Microbiology, 60(1):451.
61. Collado, M. C., Grześkowiak, Ł., & Salminen, S. (2007). Probiotic strains and their combination inhibit in vitro adhesion of pathogens to pig intestinal mucosa. Current microbiology, 55(3), 260-265.
62. Collins, E. R., Barker, J. C., Carr, L. E., Brodie, H. L. & Martin, J. H. (1999). Poultry waste management handbook; Tables 1-1, 1-2, 1-5, 1-6 and 1-9, and FIG. 2-1. NRAES-132. ISBN 0-935817-42-5. Ithaca, N.Y., USA, Natural Resource, Agriculture, and Engineering Service (NRAES)
63. Coloe, P. J., Bagust, T. J. & Ireland, L. (1984) Development of the normal gastrointestinal microflora of specific pathogen-free chickens. The Journal of Hygiene, 92(1):79-87.
64. Cox, N. A., Richardson, L. J., Maurer, J. J., Berrang, M. E., Fedorka-Cray, P. J., Buhr, R. J., & Lammerding, A. M. (2012). Evidence for horizontal and vertical transmission in *Campylobacter* passage from hen to her progeny. Journal of Food Protection®, 75(10), 1896-1902.
65. Craig, N. L. (1997). Target site selection in transposition. Annual review of biochemistry, 66(1):437-74.
66. Cromwell, G. L. (2002). Why and how antibiotics are used in swine production. Animal Biotechnology, 13: 7-27.
67. D'Costa, V. M., King, C. E., Kalan, L., Morar, M., Sung, W. W., Schwarz, C., . . . & Golding, G. B. (2011). Antibiotic resistance is ancient. Nature, 477(7365), 457-461.
68. Davey, P., Brown, E., Charani, E., Fenelon, L., Gould, I. M., Holmes, A., . . . & Wilcox, M. (2013). Interventions to improve antibiotic prescribing practices for hospital inpatients. The Cochrane Library.
69. Davies, J. (1994). Inactivation of antibiotics and the dissemination of resistance genes. Science, 264(5157), 375-382.
70. Davies, J. E. (2008). Origins, acquisition and dissemination. Antibiotic resistance: origins, evolution, selection and spread, 787, 15.
71. Delver, E. P., Kotova, V. U., Zavilgelsky, G. B., & Belogurov, A. A. (1991). Nucleotide sequence of the gene (ard) encoding the antirestriction protein of plasmid colIb-P9. Journal of bacteriology, 173(18):5887-92.
72. Depaola, A., Peeler, J. T. & Rodrick, G. E. (1995). Effect of oxytetracycline-medicated feed on antibiotic resistance of gram-negative bacteria in catfish ponds. Applied and Environmental Microbiology. 61(6):2335-40.
73. Dethlefsen, L., McFall-Ngai, M. & Relman, D. A. (2007). An ecological and evolutionary perspective on human-microbe mutualism and disease. Nature. 449(7164):811-8.
74. Diana, M. S., Silversides, F. G., Diarrassouba, F., Pritchard, J., Masson, L., Brousseau, R., & Topp, E. (2007). Impact of feed supplementation with antimicrobial agents on growth performance of broiler chickens, *Clostridium perfringens* and *Enterococcus* counts, and antibiotic resistance phenotypes and distribution of antimicrobial resistance determinants in *Escherichia coli* isolates. Applied and environmental microbiology, 73(20), 6566-6576.
75. Diarrassouba, F., Diana, M. S., Bach, S., Delaquis, P., Pritchard, J., Topp, E., & Skura, B.
76. J. (2007). Antibiotic resistance and virulence genes in commensal *Escherichia coli* and *Salmonella* isolates from commercial broiler chicken farms. Journal of Food Protection®, 70(6), 1316-1327.
77. Dibner, J. J., & Richards, J. D. (2005). Antibiotic growth promoters in agriculture: history and mode of action. Poultry science, 84(4), 634-643.
78. Ditu, L. M., Chifiriuc, M. C., Bezirtzoglou, E., Voltsi, C., Bleotu, C., Pelinescu, D., . . . & Lazar, V. (2011). Modulation of virulence and antibiotic susceptibility of enteropathogenic *Escherichia coli* strains by *Enterococcus faecium* probiotic strain culture fractions. Anaerobe, 17(6), 448-451.
79. Dmowski, M. & Jagura-Burdzy, G. (2013). Active stable maintenance functions in low copy-number plasmids of Gram-positive bacteria I. Partition systems. Polish Journal of Microbiology, 62(1):3-16.
80. Dolejska, M., Villa, L., Poirel, L., Nordmann, P. & Carattoli, A. (2013). Complete sequencing of an IncHII-plasmid encoding the carbapenemase NDM-1, the ArmA 16S RNA methylase and a resistance nodulation cell division/multidrug efflux pump. Journal of Antimicrobial Chemotherapy, 68, 34-39
81. Dorrestein, G. V., Van Gogh, H., & Rinzema, J. D. (1984). Pharmacokinetic aspects of penicillins, aminoglycosides and chloramphenicol in birds compared to mammals. A review. Veterinary quarterly, 6(4), 216-224.
82. Dotterud, C. K., Storrø, O., Johnsen, R., & Øien, T. (2010). Probiotics in pregnant women to prevent allergic disease: a randomized, double-blind trial. British Journal of Dermatology, 163(3), 616-623.
83. Dowling, P. M. (2006) Miscellaneous antimicrobials: Ionophores, nitrofurans, nitroimidazoles, rifamycins, oxazolidones, et al. In Antimicrobial Therapy in Veterinary Medicine. Eds Giguere, S., Prescott, J. F., Baggot, J. D., Walker, R. D. & Dowling, P. M., pp. 285-300. Blackwell Publishing, Ames, Iowa
84. D'Souza, A. L., Rajkumar, C., Cooke, J., & Bulpitt, C. J. (2002). Probiotics in prevention of antibiotic associated diarrhoea: meta-analysis. Bmj, 324(7350), 1361.
85. Duffy, E. A., Lucia, L. M., Kells, J. M., Castillo, A., Pillai, S. D. & Acuff, G. R. (2005). Concentrations of *Escherichia coli* and genetic diversity and antibiotic resistance profiling of *Salmonella* isolated from irrigation water, packing shed equipment, and fresh produce in Texas. Journal of Food Protection. 68(1):70-9.
86. DuráN, G. M., & Marshall, D. L. (2005). Ready-to-eat shrimp as an international vehicle of antibiotic-resistant bacteria. Journal of Food Protection®, 68(11), 2395-2401
87. Durso, L. M., Smith, D., & Hutkins, R. W. (2004). Measurements of fitness and competition in commensal *Escherichia coli* and *E. coli* 0157: H7 strains. Applied and environmental microbiology, 70(11), 6466-6472.
88. Dworkin, R. J. (1999) Aminoglycosides for the treatment of gram-negative infections: therapeutic use, resistance and future outlook. Drug Resistance Update 2:173-179

89. Dyda, F., Klein, D. C., & Hickman, A. B. (2000). GCN5-related N-acetyltransferases: a structural overview. Annual review of biophysics and biomolecular structure, 29(1), 81-103.
90. Economic and Social Committee of the European Union. (1998). Opinion on resistance to antibiotics as a threat to public health. No. ESC-98-016-EN. Accessed July 2016.
91. Egea, P., López-Cerero, L., Torres, E., del Carmen Gómez-Sánchez, M., Serrano, L., Sánchez-Ortiz, M. D., Rodriguez-Baño, J. & Pascual, A. (2012). Increased raw poultry meat colonization by extended spectrum beta-lactamase-producing *Escherichia coli* in the south of Spain. International journal of food microbiology, 159(2): 69-73
92. Ehmann, D. E., Jahić, H., Ross, P. L., Gu, R. F., Hu, J., Kern, G., . . . & Fisher, S. L. (2012). Avibactam is a covalent, reversible, non-β-lactam β-lactamase inhibitor. Proceedings of the National Academy of Sciences, 109 (29), 11663-11668.
93. Elliott, S. D. & Barnes, E. M. (1959). Changes in serological type and antibiotic resistance on Lancefield group D streptococci in chickens receiving dietary chlortetracycline. J. Gen. Microbiol. 20:426-433.
94. Esposito, E., Iacono, A., Bianco, G., Autore, G., Cuzzocrea, S., Vajro, P., . . . & Meli, R. (2009). Probiotics reduce the inflammatory response induced by a high-fat diet in the liver of young rats. The Journal of nutrition, 139(5), 905-911.
95. European Commission. (2005). Regulation 1831/2003/ EC on additives for use in animal nutrition, replacing Directive 70/524/EEC on additives in feeding-stuffs. European Commission Press releases database.
96. Fabia, R., Ar'Rajab, A., Johansson, M. L., Willen, R., Andersson, R., Molin, G., & Bengmark, S. (1993). The effect of exogenous administration of *Lactobacillis reuteri* R2LC and oat fiber on acetic acid-induced colitis in the rat. Scandinavian journal of gastroenterology, 28(2), 155-162.
97. Fairchild, A. S., Smith, J. L., Idris, U., Lu, J., Sanchez, S., Purvis, L. B., . . . & Lee, M. D. (2005). Effects of orally administered tetracycline on the intestinal community structure of chickens and on tet determinant carriage by commensal bacteria and *Campylobacter jejuni* Applied and environmental microbiology, 71(10), 5865-5872.
98. Fillgrove, K. L., Pakhomova, S., Newcomer, M. E. & Armstrong, R. N. (2003). Mechanistic diversity of fosfomycin resistance in pathogenic microorganisms. Journal of the American Chemical Society. 125, 15730-15731.
99. Fluit, A. C., & Schmitz, F. J. (1999). Class 1 integrons, gene cassettes, mobility, and epidemiology. European Journal of Clinical Microbiology and Infectious Diseases, 18(11), 761-770.
100. Food and Agriculture Organization of the United Nation (FAO). (2013). Statistical Yearbook 2013: World Food and Agriculture. Food and Agriculture Organization of the United Nations, Rome, 289. P140
101. Frazier, D. L., Jones, M. P., & Orosz, S. E. (1995). Pharmacokinetic considerations of the renal system in birds: part II. Review of drugs excreted by renal pathways. Journal of Avian Medicine and Surgery, 104-121.
102. Fridkin, S., Baggs, J., Fagan, R., Magill, S., Pollack, L. A., Malpiedi, P., . . . & Samore, M. H. (2014). Vital signs: improving antibiotic use among hospitalized patients. MMWR. Morbidity and mortality weekly report, 63(9), 194-200.
103. Fritsche, T. R., Castanheira, M., Miller, G. H., Jones, R. N. & Armstrong, E. S. (2008). Detection of methyltransferases conferring high-level resistance to aminoglycosides in Enterobacteriaceae from Europe, North America, and Latin America. Antimicrobial Agents Chemotherapy, 52, 1843-1845
104. Fuller, R. (1992). History and development of probiotics. In Probiotics (pp. 1-8). Springer Netherlands.
105. Furrie, E., Macfarlane, S., Kennedy, A., Cummings, J. H., Walsh, S. V., O'neil, D. A., & Macfarlane, G. T. (2005). Synbiotic therapy (*Bifidobacterium longum*/Synergy 1) initiates resolution of inflammation in patients with active ulcerative colitis: a randomised controlled pilot trial. Gut, 54(2), 242-249.
106. Gao, W., Chua, K., Davies, J. K., Newton, H. J., Seemann, T., Harrison, P. F., . . . & Stinear, T. P. (2010). Two novel point mutations in clinical *Staphylococcus aureus* reduce linezolid susceptibility and switch on the stringent response to promote persistent infection. PLoS Pathog, 6(6), e1000944.
107. Giguere, S. (2006) Macrolides, azalides, and ketolides. In Antimicrobial Therapy in Veterinary Medicine. Eds Giguere, S., Prescott, J. F., Baggot, J. D., Walker, R. D. & Dowling, P. M., pp. 191-206. Blackwell Publishing, Ames, Iowa
108. Giguère, S. (2013). Lincosamides, pleuromutilins, and streptogramins. Antimicrobial Therapy in Veterinary Medicine, Fifth Edition, 199-210.
109. Gionchetti, P., Rizzello, F., Lammers, K. M., Morselli, C., Sollazzi, L., Davies, S., Tambasco, R., Calabrese, C., & Campieri, M. (2006). Antibiotics and probiotics in treatment of inflammatory bowel. World J Gastroenterol, 12(21), 3306-3313.
110. Goetting, V., Lee, K. A., & Tell, L. A. (2011). Pharmacokinetics of veterinary drugs in laying hens and residues in eggs: a review of the literature. Journal of veterinary pharmacology and therapeutics, 34(6), 521-556.
111. Gotteland, M., Brunser, O., & Cruchet, S. (2006). Systematic review: are probiotics useful in controlling gastric colonization by *Helicobacter pylori*?. Alimentary pharmacology & therapeutics, 23(8), 1077-1086.
112. Götz, A., Pukall, R., Smit, E., Tietze, E., Prager, R., Tschäpe, H., . . . & Smalla, K. (1996). Detection and characterization of broad-host-range plasmids in environmental bacteria by PCR. Applied and Environmental Microbiology, 62(7), 2621-2628.
113. Graham, D. Y. & Fischbach, L. (2010). *Helicobacter pylori* treatment in the era of increasing antibiotic resistance. Gut, gut-2009;
114. Grozdanov, L., Raasch, C., Schulze, J., Sonnenborn, U., Gottschalk, G., Hacker, J., & Dobrindt, U. (2004). Analysis of the genome structure of the nonpathogenic probiotic *Escherichia coli* strain Nissle 1917. Journal of bacteriology, 186(16), 5432-5441.
115. Gryczan, T. J., Grandi, G., Hahn, J., Grandi, R., & Dubnau, D. (1980). Conformational alteration of mRNA structure and the posttranscriptional regulation of erythromycin-induced drug resistance. Nucleic acids research, 8(24), 6081-6097.
116. Hagedorn, C., Robinson, S. L., Filtz, J. R., Grubbs, S. M., Angier, T. A., & Reneau, R. B. (1999). Determining sources of fecal pollution in a rural Virginia watershed with antibiotic resistance patterns in fecal streptococci. Applied and Environmental Microbiology, 65(12), 5522-5531.
117. Hao, Q., Lu, Z., Dong, B. R., Huang, C. Q., & Wu, T. (2011). Probiotics for preventing acute upper respiratory tract infections. The Cochrane Library.

118. Hart, W. S., Heuzenroeder, M. W., & Barton, M. D. (2006). A study of the transfer of tetracycline resistance genes between *Escherichia coli* in the intestinal tract of a mouse and a chicken model. Journal of Veterinary Medicine, Series B, 53(7), 333-340.

119. Hasman, H., Mevius, D., Veldman, K., Olesen, I., & Aarestrup, F. M. (2005). β-Lactamases among extended-spectrum β-lactamase (ESBL)-resistant *Salmonella* from poultry, poultry products and human patients in The Netherlands. Journal of Antimicrobial Chemotherapy, 56(1), 115-121.

120. Hatch, R. A., & Schiller, N. L. (1998). Alginate Lyase Promotes Diffusion of Aminoglycosides through the Extracellular Polysaccharide of MucoidPseudomonas *aeruginosa*. Antimicrobial agents and chemotherapy, 42(4), 974-977.

121. Hayes, J. R., English, L. L., Carr, L. E., Wagner, D. D., & Joseph, S. W. (2004). Multiple-antibiotic resistance of *Enterococcus* spp. isolated from commercial poultry production environments. Applied and Environmental Microbiology, 70(10), 6005-6011.

122. Hempel, S., Newberry, S. J., Maher, A. R., Wang, Z., Miles, J. N., Shanman, R., Johnsen, B.,& Shekelle, P. G. (2012). Probiotics for the prevention and treatment of antibiotic-associated diarrhea: a systematic review and meta-analysis. Jama, 307(18), 1959-1969.

123. Heuer, H., Schmitt, H. & Smalla K. (2011). Antibiotic resistance gene spread due to manure application on agricultural fields. Current opinion in microbiology, 14(3): 236-243

124. Hill, C., Guarner, F., Reid, G., Gibson, G. R., Merenstein, D. J., Pot, B., . . . & Calder, P. C. (2014). Expert consensus document: The International Scientific Association for Probiotics and Prebiotics consensus statement on the scope and appropriate use of the term probiotic. Nature Reviews Gastroenterology & Hepatology, 11(8), 506-514.

125. Hilleringmann, M., Pansegrau, W., Doyle, M., Kaufman, S., MacKichan, M. L., Gianfaldoni, C., Ruggiero, P. & Covacci, A. (2006). Inhibitors of *Helicobacter pylori* ATPase Caga block CagA transport and cag virulence. Microbiology, 152(10):2919-30.

126. Hooper, L. V. & Gordon, J. I. (2001). Commensal host-bacterial relationships in the gut. Science, 292 (5519):1115-8.

127. Hooper, L. V. (2004). Bacterial contributions to mammalian gut development. Trends in microbiology, 12(3): 129-34.

128. Hoveyda, N., Heneghan, C., Mahtani, K. R., Perera, R., Roberts, N., & Glasziou, P. (2009). A systematic review and meta-analysis: probiotics in the treatment of irritable bowel syndrome. Bmc Gastroenterology, 9(1), 1.

129. Hu, Y., Yang, X., Qin, J., Lu, N., Cheng, G., Wu, N., Pan, Y., Li, J., Zhu, L., Wang, X. & Meng, Z. (2013). Metagenome-wide analysis of antibiotic resistance genes in a large cohort of human gut microbiota. Nature communications, 4.

130. Huang, Y., Zhang, L., Tiu, L., & Wang, H. H. (2015). Characterization of antibiotic resistance in commensal bacteria from an aquaculture ecosystem. Frontiers in microbiology, 6.

131. Illumina surport. (2013). 16S Metagenomic Sequencing Library Preparation.

132. Isolauri, E., Sütas, Y., Kankaanpää, P., Arvilommi, H., & Salminen, S. (2001). Probiotics: effects on immunity. The American journal of clinical nutrition, 73(2), 444s-450s.

133. Jacoby, G. A., (2009). Amp C beta-lactamases. Clinical Microbiology Reviews; 22(1):161-182

134. Jernberg, C., Löfmark, S., Edlund, C., & Jansson, J. K. (2007). Long-term ecological impacts of antibiotic administration on the human intestinal microbiota. The ISME journal, 1(1), 56-66.

135. Johnson, T. J., Lang, K. S. (2012). IncA/C plasmids: An emerging threat to human and animal health? Mobile genetic elements, 2(1):55-8

136. Johnston, B. C., Ma, S. S., Goldenberg, J. Z., Thorlund, K., Vandvik, P. O., Loeb, M., & Guyatt, G. H. (2012). Probiotics for the prevention of *Clostridium difficile*-associated diarrhea: a systematic review and meta-analysis. Annals of internal medicine, 157(12), 878-888.

137. Jongbloed, A. W. & Lenis, N. P. (1998). Environmental concerns about animal manure. Journal of Animal Science. 76(10):2641-8.

138. Kaatz, G. W., Thyagarajan, R. V., & Seo, S. M. (2005). Effect of promoter region mutations and mgrA overexpression on transcription of norA, which encodes a *Staphylococcus aureus* multidrug efflux transporter. Antimicrobial agents and chemotherapy, 49(1), 161-169.

139. Kannan, K., & Mankin, A. S. (2011). Macrolide antibiotics in the ribosome exit tunnel: species-specific binding and action. Annals of the New York Academy of Sciences, 1241(1), 33-47.

140. Kaplan, J. B. (2011). Antibiotic-induced biofilm formation. International journal of Artificial Organs, 34(9): 737-751.

141. Karami, N., Martner, A., Enne, V. I., Swerkersson, S., Adlerberth, I., & Wold, A. E. (2007). Transfer of an ampicillin resistance gene between two *Escherichia coli* strains in the bowel microbiota of an infant treated with antibiotics. Journal of antimicrobial chemotherapy, 60(5), 1142-1145.

142. Kassam, Z., Hundal, R., Marshall, J. K., & Lee, C. H. (2012). Fecal transplant via retention enema for refractory or recurrent *Clostridium difficile* infection. Archives of internal medicine, 172(2), 191-193.

143. Kim, S. R., & Komano, T. (1997). The plasmid R64 thin pilus identified as a type IV pilus. Journal of bacteriology, 179(11), 3594-3603.

144. Knapp, C. W., Dolfing, J., Ehlert, P. A., & Graham, D. W. (2009). Evidence of increasing antibiotic resistance gene abundances in archived soils since 1940. Environmental science & technology, 44(2), 580-587.

145. Kohanski, M. A., DePristo, M. A., & Collins, J. J. (2010). Sublethal antibiotic treatment leads to multidrug resistance via radical-induced mutagenesis. Molecular cell, 37(3), 311-320.

146. Kopecko, D. J. (1980). Specialized genetic recombination systems in bacteria: their involvement in gene expression and evolution. In Progress in molecular and subcellular biology (pp. 135-234). Springer Berlin Heidelberg.

147. Kroll, J., Klinter, S., Schneider, C., & Steinbüchel, A. (2010). Plasmid addiction systems: perspectives and applications in biotechnology. Microbial biotechnology, 3(6):634-57

148. Kuitunen, M., Kukkonen, K., Juntunen-Backman, K., Korpela, R., Poussa, T., Tuure, T., Haahtela, T., & Savilahti, E. (2009). Probiotics prevent IgE-associated allergy until age 5 years in cesarean-delivered children but not in the total cohort. Journal of Allergy and Clinical Immunology, 123(2), 335-341.

149. Lakhotia, R. L., Stephens, J. F. (1973). Drug resistance and R factors among enterobacteria isolated from eggs. Poultry science, 52(5): 1955-1962.

150. Lavigne, J. P., Sotto, A., Nicolas-Chanoine, M. H., Bouziges, N., Pages, J. M., & Davin-Regli, A. (2013). An adaptive response of *Enterobacter aerogenes* to imipenem: regulation of porin balance in clinical isolates. International journal of antimicrobial agents, 41(2), 130-136.

151. Laxminarayan, R., Duse, A., Wattal, C., Zaidi, A. K., Wertheim, H. F., Sumpradit, N., . . . & Greko, C. (2013). Antibiotic resistance—the need for global solutions. The Lancet infectious diseases, 13(12), 1057-1098.

152. Leach, D. & Symonds, N. (1979). The isolation and characterisation of a plaque-forming derivative of bacteriophage Mu carrying a fragment of Tn3 conferring ampicillin resistance. Molecular and General Genetics, 172(2):179-84.

153. Leclercq, R. & Courvalin, P. (1991). Bacterial resistance to macrolide, lincosamide, and streptogramin antibiotics by target modification. Antimicrobial Agents and Chemotherapy 35, 1267-72.

154. Levings, R. S., Partridge, S. R., Lightfoot, D., Hall, R. M., & Djordjevic, S. P. (2005) New integron-associated gene cassette encoding a 3-Naminoglycoside acetyltransferase. Antimicrobial Agents Chemotherapy, 49:1238-1241

155. Levy, S. B. (1978). Emergence of antibiotic-resistant bacteria in the intestinal flora of farm inhabitants. Journal of Infectious Diseases, 137:689-690

156. Levy, S. B., Marshall, B., Schluederberg, S., Rowse, D.& Davis, J. (1988). High frequency of antimicrobial resistance in human fecal flora. Antimicrobial agents and chemotherapy, 32(12):1801-6.

157. Lewicki, J., Reeves, P. T. & Swan, G. E. (2008) Residue Evaluation of Certain Veterinary Drugs, 70th meeting of the Joint FAO/WHO Expert Committee on Food Additives, 243-279

158. Lewis, K. (2013). Platforms for antibiotic discovery. Nature reviews Drug discovery, 12(5), 371-387.

159. Li D, Yang M, Hu J, Zhang J, Liu R, Gu X, Zhang Y, Wang Z. (2009). Antibiotic-resistance profile in environmental bacteria isolated from penicillin production wastewater treatment plant and the receiving river. Environmental microbiology, 11(6):1506-17.

160. Li, X., Li, Y., Alvarez, V., Harper, W. J., & Wang, H. H. (2011). Effective antibiotic resistance mitigation during cheese fermentation. Applied and environmental microbiology, 77(20), 7171-7175.

161. Li, X. & Wang, H. H. (2010). Tetracycline resistance associated with commensal bacteria from representative ready-to-consume deli and restaurant foods. Journal of Food Protection, 73(10): 1841-1848.

162. Lievin-Le Moal, V., Amsellem, R., Servin, A. L., & Coconnier, M. H. (2002). *Lactobacillus acidophilus* (strain LB) from the resident adult human gastrointestinal microflora exerts activity against brush border damage promoted by a diarrhoeagenic *Escherichia coli* in human enterocyte-like cells. Gut, 50(6), 803-811.

163. Lin, J., Hunkapiller, A. A., Layton, A. C., Chang, Y. J., & Robbins, K. R. (2013). Response of intestinal microbiota to antibiotic growth promoters in chickens. Foodborne pathogens and disease, 10(4), 331-337.

164. Linton, A. H., HOWE, K., Richmond, M. H., CLEMENTS, H. M., Osborne, A. D., & HANDLEY, B. (1978). Attempts to displace the indigenous antibiotic resistant gut flora of chicken by feeding sensitive strains of *Escherichia coli* prior to slaughter. Journal of Applied Bacteriology, 45(2), 239-247.

165. Liu, B., Pop, M. (2009). ARDB-Antibiotic Resistance Genes Database. Nucleic Acids Research, 37 (Database issue):D443-7

166. Looft, T., Johnson, T. A., Allen, H. K., Bayles, D. O., Alt, D. P., Stedtfeld, R. D., Sul, W. J., Stedtfeld, T. M., Chai, B., Cole, J. R. & Hashsham, S. A. (2012). In-feed antibiotic effects on the swine intestinal microbiome. Proceedings of the National Academy of Sciences, 109 (5):1691-6

167. Lu, J., Idris, U., Harmon, B., Hofacre, C., Maurer, J. J. & Lee, M. D. (2003). Diversity and succession of the intestinal bacterial community of the maturing broiler chicken. Applied Environmental Microbiology, 69(11): 6816-24

168. Lujan, S. A., Guogas, L. M., Ragonese, H., Matson, S. W. & Redinbo, M. R. (2007). Disrupting antibiotic resistance propagation by inhibiting the conjugative DNA relaxase. Proceedings of the National Academy of Sciences, 104(30):12282-7

169. Lundeen T. (2016). Feed Additive Compendium 2016: A guide to use of drug in medicated animal feed. Penton. St. Charles, Ill., USA.

170. Luo, N., Pereira, S., Sahin, O., Lin, J., Huang, S., Michel, L., & Zhang, Q. (2005). Enhanced in vivo fitness of fluoroquinolone-resistant *Campylobacter jejuni* in the absence of antibiotic selection pressure. Proceedings of the National Academy of Sciences of the United States of America, 102(3), 541-546.

171. Lynch I I I, J. P., Clark, N. M., & Zhanel, G. G. (2013). Evolution of antimicrobial resistance among Enterobacteriaceae (focus on extended spectrum β-lactamases and carbapenemases). Expert opinion on pharmacotherapy, 14(2), 199-210.

172. Mack, D. R., Michail, S., Wei, S., McDougall, L., & Hollingsworth, M. A. (1999). Probiotics inhibit enteropathogenic *E. coli* adherence in vitro by inducing intestinal mucin gene expression. American Journal of Physiology-Gastrointestinal and Liver Physiology, 276 (4), G941-G950.

173. Madsen, K. L., Doyle, J. S., Jewell, L. D., Tavernini, M. M., & Fedorak, R. N. (1999).

174. *Lactobacillus* species prevents colitis in interleukin 10 gene—deficient mice. Gastroenterology, 116(5), 1107-1114.

175. Madsen, K., Cornish, A., Soper, P., McKaigney, C., Jijon, H., Yachimec, C., . . . & De Simone, C. (2001). Probiotic bacteria enhance murine and human intestinal epithelial barrier function. Gastroenterology, 121(3), 580-591.

176. Majiduddin, F. K., Materon, I. C., & Palzkill, T. G. (2002). Molecular analysis of beta-lactamase structure and function. International journal of medical microbiology, 292(2), 127-137.

177. Malani, A. N., Richards, P. G., Kapila, S., Otto, M. H., Czerwinski, J., & Singal, B. (2013). Clinical and economic outcomes from a community hospital's antimicrobial stewardship program. American journal of infection control, 41(2), 145-148.

178. Mao, Y., Nobaek, S., Kasravi, B., Adawi, D, Stenram, U., Molin, G, & Jeppsson, B. (1996). The effects of *Lactobacillus* strains and oat fiber on methotrexate-induced enterocolitis in rats. Gastroenterology, 111(2), 334-344.

179. Maravic, G. (2004). Macrolide resistance based on the Erm-mediated rRNA methylation. Current Drug Targets-Infectious Disorders, 4(3), 193-202.
180. Marshall, B. M., Ochieng, D. J. & Levy, S. B. (2009) Commensals: underappreciated reservoir of antibiotic resistance. Microbe, 4(5):231-8
181. Martinez, J. L. (2008). Antibiotics and antibiotic resistance genes in natural environment. Science, 321(5887): 365-367
182. Mathew, A. G., Cissell, R. & Liamthong, S. (2007). Antibiotic resistance in bacteria associated with food animals: a United States perspective of livestock production. Foodborne Pathogens and Disease, 4(2):115-33.
183. Matsuoka, M., Endou, K., Kobayashi, H., Inoue, M., & Nakajima, Y. (1998). A plasmid that encodes three genes for resistance to macrolide antibiotics in *Staphylococcus aureus*. FEMS Microbiology Letters, 167(2), 221-227.
184. McArthur, A. G., Waglechner, N., Nizam, F., Yan, A., Azad, M. A., Baylay, A. J., . . . & Kalan, L. (2013). The comprehensive antibiotic resistance database. Antimicrobial agents and chemotherapy, 57(7), 3348-3357.
185. McFarland, L. V. (2006). Meta-analysis of probiotics for the prevention of antibiotic associated diarrhea and the treatment of *Clostridium difficile* disease. The American journal of gastroenterology, 101(4), 812-822.
186. McKay, G. A., & Wright, G. D. (1995). Kinetic mechanism of aminoglycoside phosphotransferase type IIIa: evidence for a Theorell—Chance mechanism. Journal of Biological Chemistry, 270:24686-24692;
187. Mead, G. C. (1989). Microbes of the avian cecum: types present and substrates utilized. Journal of Experimental Zoology. 3(Suppl.):48-54.
188. Meier, A., Kirschner, P., Bange, F. C., Vogel, U., & Bottger, E. C. (1994). Genetic alterations in streptomycin-resistant *Mycobacterium tuberculosis*: mapping of mutations conferring resistance. Antimicrobial agents and chemotherapy, 38(2), 228-233.
189. Melancon, P., W. E. Tapprich, and L. Brakier-Gingras. (1992). Single-base mutations at position 2661 of *Escherichia coli* 23S rRNA increase efficiency of translational proofreading. J. Bacteriol. 174:7896-7901
190. Mennigen, R., Nolte, K., Rijcken, E., Utech, M., Loeffler, B., Senninger, N., & Bruewer, M. (2009). Probiotic mixture VSL #3 protects the epithelial barrier by maintaining tight junction protein expression and preventing apoptosis in a murine model of colitis. American journal of physiology-Gastrointestinal and liver physiology, 296(5), G1140-G1149.
191. Modi, S. R., Lee, H. H., Spina, C. S. & Collins, J. J. (2013). Antibiotic treatment expands the resistance reservoir and ecological network of the phage metagenome. Nature, 499(7457):219-22.
192. Moore, P. R., A. Evenson, T. D. Luckey, E. McCoy, E. A. Elvehjem, and E. B. Hart. (1946). Use of sulphasuccidine, streptothricin and streptomycin in nutrition studies with the chick. J. Biol. Chem, 165:437-441
193. Moore, P. A., Daniel, T. C., Sharpley, A. N., & Wood, C. W. (1995). Poultry manure management: Environmentally sound options. Journal of soil and water conservation, 50(3), 321-327.
194. Moubareck, C., Lecso, M., Pinloche, E., Butel, M. J., & Doucet-Populaire, F. (2007). Inhibitory impact of bifidobacteria on the transfer of β-lactam resistance among Enterobacteriaceae in the gnotobiotic mouse digestive tract. Applied and environmental microbiology, 73(3), 855-860.
195. Musa, H. H., & Seri, H. (2016). The potential benefits of probiotics in animal production and health.
196. Muyzer, G., De Waal, E. C., & Uitterlinden, A. G. (1993). Profiling of complex microbial populations by denaturing gradient gel electrophoresis analysis of polymerase chain reaction-amplified genes coding for 16S rRNA. Applied and environmental microbiology, 59(3): 695-700.
197. Naderi, A., Kasra-Kermanshahi, R., Gharavi, S., Fooladi, A. A. I., Alitappeh, M. A., & Saffarian, P. (2014). Study of antagonistic effects of *Lactobacillus* strains as probiotics on multi drug resistant (MDR) bacteria isolated from urinary tract infections (UTIs). Iranian journal of basic medical sciences, 17(3), 201.
198. Nadkarni, M. A., F. E. Martin, N. A. Jacques, and N. Hunter. (2002). Determination of bacterial load by real-time PCR using a broad-range (universal) probe and primers set. Microbiology 148:257-266.
199. Nagy, Z. & Chandler, M. (2004). Regulation of transposition in bacteria. Research in microbiology, 155(5): 387-98
200. Ng, S. C., Hart, A. L., Kamm, M. A., Stagg, A. J., & Knight, S. C. (2009). Mechanisms of action of probiotics: recent advances Inflammatory bowel diseases, 15(2), 300-310.
201. Nissle A. On the fundamentals for new causal control of pathological intestinal microflora [Ueber die Grundlagen einer neuen ursaechlichen Bekaempfung der pathologischen Darmflora]. (1961). Deutsche Medizinische Wochenschrift. 1181-1184;
202. Nissle A. The antagonistic therapy of chronic intestinal disturbances [Die antagonistische Behandlung chronischer Darmstoerungenmit Colibakterien]. (1918). Med Klinik. 29-30
203. Noguchi, N., Katayama, J., & O'Hara, K. (1996). Cloning and nucleotide sequence of the mphB gene for macrolide 2'-phosphotransferase II in *Escherichia coli*. FEMS microbiology letters, 144(2-3), 197-202.
204. Norton, M. D., Spilkia, A. J., & Godoy, V. G. (2013). Antibiotic resistance acquired through a DNA damage-inducible response in *Acinetobacter baumannii*. Journal of bacteriology, 195(6), 1335-1345.
205. Novotny, C., Knight, W. S. & Brinton, C. C. (1968). Inhibition of bacterial conjugation by ribonucleic acid and deoxyribonucleic acid male-specific bacteriophages. Journal of bacteriology. 95(2):314-26.
206. Nunes, R. V., Scherer, C., Pozza, P. C., Eyng, C., Bruno, L. D. G., & Vieites, F. M. (2012). Use of probiotics to replace antibiotics for broilers. Revista Brasileira de Zootecnia, 41(10), 2219-2224.
207. O'Hara, K., Kanda, T., Ohmiya, K., Ebisu, T. & Kono M. (1989). Purification and characterization of macrolide 2V-phosphotransferase from a strain of *Escherichia coli* that is highly resistant to erythromycin, Antimicrobial Agents Chemotherapy, 33, 1354-1357.
208. Olliver, A., Vallé, M., Chaslus-Dancla, E. & Cloeckaert, A. (2004). Role of an acrR mutation in multidrug resistance of in vitro-selected fluoroquinolone-resistant mutants of *Salmonella enterica* serovar *Typhimurium*. FEMS Microbiolial Letters, 238, 267-272.
209. Ondov, B. D., Bergman, N. H., & Phillippy, A. M. (2011). Interactive metagenomic visualization in a Web browser. BMC bioinformatics, 12(1), 1.
210. Otte, J. M., & Podolsky, D. K. (2004). Functional modulation of enterocytes by gram-positive and gram-negative microorganisms. American Journal of Physiology-Gastrointestinal and Liver Physiology, 286(4), G613-G626.
211. Ounissi, H., & Courvalin, P. (1985). Nucleotide sequence of the gene ereA encoding the erythromycin esterase in *Escherichia coli*. Gene, 35(3), 271-278.
212. Overbeek, R., Olson, R., Pusch, G. D., Olsen, G. J., Davis, J. J., Disz, T., . . . & Vonstein, V. (2014). The SEED and the Rapid Annotation of microbial genomes using Subsystems Technology (RAST). Nucleic acids research, 42(D1), D206-D214.
213. Pallen, M. J. & Wren, B. W. (2007). Bacterial pathogenomics. Nature, 449(7164):835-42
214. Patterson, J. A. & Burkholder, K. M. (2003). Application of prebiotics and probiotics in poultry production. Poultry science, 82(4): 627-631.
215. Pelicano, E. R. L., De Souza, P. A., De Souza, H. B. A., Leonel, F. R., Zeola, N. M. B. L., & Boiago, M. M. (2004). Productive traits of broiler chickens fed diets containing different growth promoters. Revista Brasileira de Ciência Avícola, 6(3), 177-182.
216. Perreten, V., & Boerlin, P. (2003). A new sulfonamide resistance gene (sul3) in *Escherichia coli* is widespread in the pig population of Switzerland. Antimicrobial agents and chemotherapy, 47(3), 1169-1172.
217. Petri, W. A. J. (2006). Antimicrobial agents: sulfonamides, trimethoprim-sulfamethoxazole, quinolones, and agents for urinary tract infections. In: Brunton, L. L., Lazo, J. S., Parker, K. L., eds. Goodman & Gilman's The Pharmacological Basis of Therapeutics, 11th ed. New York: McGrawHill, 1111-1126
218. Poole, K. (2004). Resistance to beta-lactam antibiotics. Cellular and Molecular Life Sciences, 61(17):2200-2223
219. Price, L. B., Lackey, L. G., Vailes, R. & Silbergeld, E. (2007). The persistence of fluoroquinolone-resistant *Campylobacter* in poultry production Environmental[J]. Health Perspectives, 1035-1039.
220. Rasko, D. A., Moreira, C. G., Li, D. R., Reading, N.C., Ritchie, J. M., Waldor, M. K., Williams, N., Taussig, R., Wei, S., Roth, M. & Hughes, D. T. (2008). Targeting QseC signaling and virulence for antibiotic development. Science. 321(5892):1078-80.
221. Rea, M. C., Clayton, E., O'Connor, P. M., Shanahan, F., Kiely, B., Ross, R. P., & Hill, C. (2007). Antimicrobial activity of lacticin 3147 against clinical *Clostridium difficile* strains. Journal of Medical Microbiology, 56(7), 940-946.
222. Resta-Lenert, S., & Barrett, K. E. (2003). Live probiotics protect intestinal epithelial cells from the effects of infection with enteroinvasive *Escherichia coli* (EIEC). Gut, 52(7), 988-997.
223. Roberts, M. C. (2008). Update on macrolide—lincosamide—streptogramin, ketolide, and oxazolidinone resistance genes. FEMS microbiology letters, 282(2):147-59
224. Roe, M. T., and S. D. Pillai. (2003). Monitoring and identifying antibiotic resistance mechanisms in bacteria. Poultry Science.82:622-626.
225. Rolain, J. M. (2013). Food and human gut as reservoirs of transferable antibiotic resistance encoding genes. Frontiers in microbiology, 4:173.
226. Ross, J. I., Eady, E. A., Cove, J. H., Cunliffe, W. J., Baumberg, S., & Wootton, J. C. (1990). Inducible erythromycin resistance in staphlyococci is encoded by a member of the ATP-binding transport super-gene family. Molecular microbiology, 4(7), 1207-1214.
227. Salyers, A. A., & Amabile-Cuevas, C. F. (1997). Why are antibiotic resistance genes so resistant to elimination?. Antimicrobial agents and chemotherapy, 41(11), 2321.
228. Sarmah, A. K., Meyer, M. T. & Boxall, A. B. (2006). A global perspective on the use, sales, exposure pathways, occurrence, fate and effects of veterinary antibiotics (VAs) in the environment. Chemosphere. 65(5):725-59.
229. Schnappinger, D., & Hillen, W. (1996). Tetracyclines: antibiotic action, uptake, and resistance mechanisms. Archives of microbiology, 165(6), 359-369.
230. Schultz, M., Veltkamp, C., Dieleman, L. A., Grenther, W. B., Wyrick, P. B., Tonkonogy, S. L., & Sartor, R. B. (2002). *Lactobacillus plantarum* 299V in the treatment and prevention of spontaneous colitis in interleukin-10-deficient mice Inflammatory bowel diseases, 8(2), 71-80.
231. Schwarz, S., Kehrenberg, C., Doublet, B., & Cloeckaert, A. (2004). Molecular basis of bacterial resistance to chloramphenicol and florfenicol. FEMS microbiology reviews, 28(5), 519-542.
232. Scott, K. P., Gratz, S. W., Sheridan, P. O., Flint, H. J., & Duncan, S. H. (2013). The influence of diet on the gut microbiota. Pharmacological research, 69(1), 52-60.
233. Sengelov, G., Agersø, Y., Halling-Sørensen, B., Baloda, S. B., Andersen, J. S., & Jensen, L. B. (2003). Bacterial antibiotic resistance levels in Danish farmland as a result of treatment with pig manure slurry. Environment international, 28(7), 587-595.
234. Shen, J., Zuo, Z. X., & Mao, A. P. (2014). Effect of probiotics on inducing remission and maintaining therapy in ulcerative colitis, Crohn's disease, and pouchitis: meta-analysis of randomized controlled trials Inflammatory bowel diseases, 20(1), 21-35.
235. Sherman, P. M., Johnson-Henry, K. C., Yeung, H. P., Ngo, P. S., Goulet, J., & Tompkins, T. A. (2005). Probiotics reduce enterohemorrhagic *Escherichia coli* O157: H7- and enteropathogenic *E. coli* O127: H6-induced changes in polarized T84 epithelial cell monolayers by reducing bacterial adhesion and cytoskeletal rearrangements. Infection and immunity, 73(8), 5183-5188.
236. Shoemaker, N. B., Vlamakis, H., Hayes, K., & Salyers, A. A. (2001). Evidence for Extensive Resistance Gene Transfer amongBacteroides spp. and among *Bacteroides* and Other Genera in the Human Colon. Applied and environmental microbiology, 67(2), 561-568.
237. Shoemaker, N. B., Vlamakis, H., Hayes, K. & Salyers, A. A. (2001). Evidence for Extensive Resistance Gene Transfer amongBacteroides spp. and among *Bacteroides* and Other Genera in the Human Colon. Applied and environmental microbiology, 67(2):561-8;
238. Shore, A. C., Deasy, E. C., Slickers, P., Brennan, G., O'Connell, B., Monecke, S., . . . & Coleman, D. C. (2011). Detection of staphylococcal cassette chromosome mec type XI carrying highly divergent mecA, mecI, mecR1, blaZ, and ccr genes in human clinical isolates of clonal complex 130 methicillin-resistant *Staphylococcus aureus*. Antimicrobial agents and chemotherapy, 55(8), 3765-3773.
239. Silver, L. L. (2011). Challenges of antibacterial discovery. Clinical microbiology reviews, 24(1), 71-109.
240. Singh, P., Karimi, A., Devendra, K., Waldroup, P. W., Cho, K. K., & Kwon, Y. M. (2013). Influence of penicillin on microbial diversity of the cecal microbiota in broiler chickens. Poultry science, 92(1), 272-276.
241. Sköld, O. (2000). Sulfonamide resistance: mechanisms and trends. Drug Resistance Updates, 3(3), 155-160.
242. Sköld, O. (2001). Resistance to trimethoprim and sulfonamides. Veterinary research. 32(3-4):261-73

243. Smillie, C., Garcillán-Barcia, M. P., Francia, M. V., Rocha, E. P., & de la Cruz, F. (2010). Mobility of plasmids. Microbiology and Molecular Biology Reviews, 74(3):434-52
244. Smith, D. L., Dushoff, J., Perencevich, E. N., Harris, A. D., & Levin, S. A. (2004). Persistent colonization and the spread of antibiotic resistance in nosocomial pathogens: resistance is a regional problem. Proceedings of the National Academy of Sciences of the United States of America, 101(10), 3709-3714.
245. Smith, D. L., Levin, S. A., & Laxminarayan, R. (2005). Strategic interactions in multi-institutional epidemics of antibiotic resistance. Proceedings of the National Academy of Sciences of the United States of America, 102(8), 3153-3158.
246. Smith, H. W. (1970). The transfer of antibiotic resistance between strains of enterobacteria in chicken, calves and pigs. Journal of medical microbiology, 3(1): 165-180.
247. Sommer, F. & Bäckhed, F. (2013). The gut microbiota—masters of host development and physiology. Nature Reviews Microbiology, 11(4): 227-238.
248. Starr, M. P., & Reynolds, D. M. (1951). Streptomycin resistance of coliform bacteria from turkeys fed streptomycin. American Journal of Public Health and the Nations Health, 41(11_Pt_1), 1375-1380.
249. Sullivan, Å., Johansson, A., Svenungsson, B., & Nord, C. E. (2004). Effect of *Lactobacillus* F19 on the emergence of antibiotic-resistant microorganisms in the intestinal microflora. Journal of Antimicrobial Chemotherapy, 54(4), 791-797.
250. Sundqvist, M., Geli, P., Andersson, D. I., Sjolund-Karlsson, M., Runehagen, A., Cars, H., Abelson-Storby, K., Cars, O. & Kahlmeter, G. (2010). Little evidence for reversibility of trimethoprim resistance after a drastic reduction in trimethoprim use. Journal of antimicrobial chemotherapy. 65(2):350-60.
251. Tamber, S., & Hancock, R. E. (2003). On the mechanism of solute uptake in *Pseudomonas*. Frontiers in bioscience: a journal and virtual library, 8, s472-83.
252. Tängdén, T., Adler, M., Cars, O., Sandegren, L., & Löwdin, E. (2013). Frequent emergence of porin-deficient subpopulations with reduced carbapenem susceptibility in ESBL-producing *Escherichia coli* during exposure to ertapenem in an in vitro pharmacokinetic model. Journal of Antimicrobial Chemotherapy, dkt044.
253. Tannock, G. W., Tiong, S., Priest, P., Munro, K., Taylor, C., Richardson, A., & Schultz, M. (2011). Testing probiotic strain *Escherichia coli* Nissle 1917 (Mutaflor) for its ability to reduce carriage of multidrug-resistant *E. coli* by elderly residents in long-term care facilities. Journal of medical microbiology, 60(3), 366-370.
254. Ten Bruggencate, S. J. M., Girard, S. A., Floris-Vollenbroek, E. G. M., Bhardwaj, R., & Tompkins, T. A. (2015). The effect of a multi-strain probiotic on the resistance toward *Escherichia coli* challenge in a randomized, placebo-controlled, double-blind intervention study. European journal of clinical nutrition, 69(3), 385-391.
255. Tenson, T., Lovmar, M., & Ehrenberg, M. (2003). The mechanism of action of macrolides, lincosamides and streptogramin B reveals the nascent peptide exit path in the ribosome. Journal of molecular biology, 330(5), 1005-1014.
256. Threlfall, E. J., Ward, L. R., Frost, J. A., & Willshaw, G. A. (2000). The emergence and spread of antibiotic resistance in food-borne bacteria. International journal of food microbiology, 62(1), 1-5.
257. Torok, V. A., Allison, G. E., Percy, N. J., Ophel-Keller, K., & Hughes, R. J. (2011). Influence of antimicrobial feed additives on broiler commensal posthatch gut microbiota development and performance. Applied and environmental microbiology, 77(10), 3380-3390.
258. Trebichaysky, I., Splichal, I., Rada, V. & Splichalova, A. (2010). Modulation of natural immunity in the gut by *Escherichia coli* strain Nissle 1917. Nutrition reviews, 68(8):459-64.
259. Tsafnat, G., Copty, J., & Partridge, S. R. (2011). RAC: repository of antibiotic resistance cassettes. Database, 2011, bar054. Accessed in July 2016.
260. Tu, D., G. Blaha, P. B. Moore & T. A. Steitz. (2005). Structures of MLSBK antibiotics bound to mutated large ribosomal subunits provide a structural explanation for resistance. Cell, 121: 257-270.
261. Tuomola, E. M., Ouwehand, A. C., & Salminen, S. J. (1999). The effect of probiotic bacteria on the adhesion of pathogens to human intestinal mucus. FEMS Immunology & Medical Microbiology, 26(2), 137-142.
262. Turner, J. (2000): Factory farming and the environment. Scn News United Nations System's Forum On Nutrition, vol. 21. Accessed in July 2016
263. U.S. Census Bureau. (2011). Broiler and Turkey Production by State: 2008 to 2010. Accessed July, 2016
264. U.S. Food and Drug Administration (2010). Draft guidance #209. Accessed July 2016.
265. U.S. Food and Drug Administration (2012). Antibacterial Drug Usage Analysis—U.S. Food and Drug Administration. Accessed July, 2016
266. U.S. Food and Drug Administration, and Center for Veterinary Medicine. (2013). Draft guidance #213. Accessed July 2016.
267. U.S. Food and Drug Administration, and Center for Veterinary Medicine. (2013). Proposed rule: Veterinary Feed Directive. Accessed July 2016.
268. U.S. Food and Drug administration. (2013). 2011 Summary Report On Antimicrobials Sold or Distributed for Use in Food-Producing Animals. Accessed July, 2016
269. U.S. Food and Drug administration. (2014). 2012 Summary Report On Antimicrobials Sold or Distributed for Use in Food-Producing Animals. Accessed July, 2016
270. U.S. Food and Drug administration. (2015). 2013 Summary Report On Antimicrobials Sold or Distributed for Use in Food-Producing Animals.
271. U.S. Food and Drug administration. (2015). 2014 Summary Report On Antimicrobials Sold or Distributed for Use in Food-Producing Animals. Accessed July, 2016
272. U.S. Food and Drug Administration (FDA). (2015) FDA Annual Summary Report on Antimicrobials Sold or Distributed in 2014 for Use in Food-Producing Animals. FDA, Center for Veterinary Medicine. Rockville, Md. Accessed Jul. 15, 2016
273. Unemo, M., Golparian, D., Nicholas, R., Ohnishi, M., Gallay, A., & Sednaoui, P. (2012). High-level cefixime- and ceftriaxone-resistant *Neisseria gonorrhoeae* in France: novel penA mosaic allele in a successful international clone causes treatment failure. Antimicrobial agents and chemotherapy, 56(3), 1273-1280.
274. Vaden, S. L. & Riviere, J. E. (2001) Penicillins and related beta-lactam antibiotics. In Veterinary Pharmacology and Therapeutics. Ed. Adams, H. R., pp. 818-827. Iowa State University Press, Ames, Iowa
275. Van Boeckel, T. P., Brower, C., Gilbert, M., Grenfell, B. T., Levin, S. A., Robinson, T. P., & Laxminarayan, R.

(2015). Global trends in antimicrobial use in food animals. Proceedings of the National Academy of Sciences, 112(18), 5649-5654.
276. Van den Bogaard, A. E., London, N., Driessen, C., & Stobberingh, E. E. (2001). Antibiotic resistance of faecal *Escherichia coli* in poultry, poultry farmers and poultry slaughterers. Journal of Antimicrobial Chemotherapy, 47(6), 763-771.
277. Van den Bogaard, A. E., Bruinsma, N. and Stobberingh, E. E., (2000). The effect of banning avoparcin on VRE carriage in The Netherlands. Journal of Antimicrobial Chemotherapy, 46(1), pp. 146-148.
278. Van Leeuwen, F. X. R. (1991) In Toxicological evaluation of certain veterinary drug residues in food. 29 The Joint FAO/WHO Expert Committee on Food Additives.
279. Van, T. T., Chin, J., Chapman, T., Tran, L. T. & Coloe, P. J. (2008). Safety of raw meat and shellfish in Vietnam: an analysis of *Escherichia coli* isolations for antibiotic resistance and virulence genes. International journal of food microbiology, 124(3):217-23;
280. Vaughan, R. B. (1965). The romantic rationalist: A study of Elie Metchnikoff. Medical history, 1; 9(3):201-15.
281. Vetting, M. W., Hegde, S. S., Wang, M., Jacoby, G. A., Hooper, D. C., & Blanchard, J. S. (2011). Structure of QnrB1, a plasmid-mediated fluoroquinolone resistance factor. Journal of Biological Chemistry, 286(28), 25265-25273.
282. Videnska, P., Faldynova, M., Juricova, H., Babak, V., Sisak, F., Havlickova, H., & Rychlik, I. (2013). Chicken faecal microbiota and disturbances induced by single or repeated therapy with tetracycline and streptomycin. BMC veterinary research, 9(1), 1.
283. Vogelman, B., Craig, W. A. (1986). Kinetics of antimicrobial activity. The Journal of pediatrics, 108(5):835-40.
284. Voulgari, E., Poulou, A., Koumaki, V. & Tsakris, A. (2013). Carbapenemase-producing Enterobacteriaceae: now that the storm is finally here, how will timely detection help us fight back? Future Microbiology, 8, 27-39
285. Vuotto, C., Longo, F., & Donelli, G. (2014). Probiotics to counteract biofilm-associated infections: promising and conflicting data. International journal of oral science, 6(4), 189-194.
286. Wang, H. H., Manuzon, M., Lehman, M., Wan, K., Luo, H., Wittum, T. E., . . . & Bakaletz, L. O. (2006). Food commensal microbes as a potentially important avenue in transmitting antibiotic resistance genes. FEMS Microbiology Letters, 254(2), 226-231.
287. Wang, H. H. (2009). Commensal bacteria, microbial ecosystems and horizontal gene transmission: adjusting our focus for strategic breakthroughs against antibiotic resistance. In Foodborne Microbes: Shaping the Host Ecosystems (Jaykus L, Wang H H, Schlesinger L., eds). p. 267-281. ASM Press.
288. Waters, A. E., Contente-Cuomo, T., Buchhagen, J., Liu, C. M., Watson, L., Pearce, K., . . . & Keim, P. S. (2011). Multidrug-resistant *Staphylococcus aureus* in US meat and poultry. Clinical Infectious Diseases, 52(10), 1227-1230.
289. Waxman, D. J., & Strominger, J. L. (1983). Penicillin-binding proteins and the mechanism of action of beta-lactam antibioticsl. Annual review of biochemistry, 52(1), 825-869.
290. Webber, M. A., Talukder, A., & Piddock, L. J. (2005). Contribution of mutation at amino acid 45 of AcrR to acrB expression and ciprofloxacin resistance in clinical and veterinary *Escherichia coli* isolates. Antimicrobial agents and chemotherapy, 49(10), 4390-4392
291. Wegener, H. C., Aarestrup, F. M., Jensen, L. B., Hammerum, A. M. & Bager, F. (1999). Use of antimicrobial growth promoters in food animals and *Enterococcus faecium* resistance to therapeutic antimicrobial drugs in Europe. Emerging infectious diseases, 5(3):329.
292. Wei, S., Morrison, M., & Yu, Z. (2013). Bacterial census of poultry intestinal microbiome. Poultry science, 92(3): 671-683.
293. Williams, C. M., Barker, J. C. & Sims, J. T. (1999). Management and utilization of poultry wastes; Tables 2, 3, 4, 5, 6 and 7. Rev. Environ. Contam. Toxicol., 162: 105-157.
294. Wise, R. (2007). An overview of the Specialist Advisory Committee on Antimicrobial Resistance (SACAR). Journal of Antimicrobial Chemotherapy, 60(suppl 1), i5-i7.
295. World Health Organization (WHO). (2014). Antimicrobial resistance: global report on surveillance 2014.
296. World Health Organization. (1997). The medical impact of the use of antimicrobials in food animals: Report of a WHO meeting, Berlin, Germany. Accessed July 2016;
297. Wright, G. D. (2005). Bacterial resistance to antibiotics: enzymatic degradation and modification. Advanced Drug Delivery Reviews, 57, 1451-1470
298. Yamamoto, T., Watanabe, M., Matsumoto, K., & Sawai, T. (1983). Tn2610, a transposon involved in the spread of the carbenicillin-hydrolyzing (3-lactamase gene. Molecular and General Genetics MGG, 189(2), 282-288.
299. Yu, Z., and M. Morrison. 2004. Improved extraction of PCR-quality community DNA from digesta and fecal samples[J]. BioTechniques. 36:808-812.
300. Zhang, L., Huang, Y., Zhou, Y., Buckley, T., & Wang, H. H. (2013). Antibiotic administration routes significantly influence the levels of antibiotic resistance in gut microbiota. Antimicrobial agents and chemotherapy, 57(8), 3659-3666.
301. Zhang, L., Kinkelaar, D., Huang, Y., Li, Y., Li, X., & Wang, H. H. (2011). Acquired antibiotic resistance: are we born with it?. Applied and environmental microbiology, 77(20), 7134-7141
302. Zhang, Q., Lambert, G., Liao, D., Kim, H., Robin, K., Tung, C. K., . . . & Austin, R. H. (2011). Acceleration of emergence of bacterial antibiotic resistance in connected microenvironments. Science, 333(6050), 1764-1767.
303. Zhao, S., White, D. G., McDermott, P. F., Friedman, S., English, L., Ayers, S., . . . & Walker, R. D. (2001). Identification and Expression of Cephamycinasebla CMY Genes in *Escherichia coli*and *Salmonella* Isolates from Food Animals and Ground Meat. Antimicrobial agents and chemotherapy, 45(12), 3647-3650.
304. Zhou, W., Wang, Y. & Lin, J. (2012). Functional cloning and characterization of antibiotic resistance genes from the chicken gut microbiome. Applied and environmental microbiology, 78(8):3028-32
305. Ziv, G., Neumann, J., Fridman, J., Ziv, E., Singer, N., & Meshorer, A. (1979). Effects of probenecid on blood levels and tissue distribution of ampicillin in fowls and turk eys. Avian diseases, 927-939.
306. Zoetendal, E. G., Cheng, B., Koike, S. & Mackie R. I. (2004). Molecular microbial ecology of the gastrointestinal tract: from phylogeny to function[J]. Current issues in intestinal microbiology, 5(2): 31-48.

307. Zyrek, A. A., Cichon, C., Helms, S., Enders, C., Sonnenborn, U., & Schmidt, M. A. (2007). Molecular mechanisms underlying the probiotic effects of *Escherichia coli* Nissle 1917 involve ZO-2 and PKCt redistribution resulting in tight junction and epithelial barrier repair. Cellular microbiology, 9(3), 804-816.

Publications cited herein are hereby specifically incorporated by reference in their entireties and at least for the material for which they are cited.

It should be understood that while the present disclosure has been provided in detail with respect to certain illustrative and specific aspects thereof, it should not be considered limited to such, as numerous modifications are possible without departing from the broad spirit and scope of the present disclosure as defined in the appended claims. It is, therefore, intended that the appended claims cover all such equivalent variations as fall within the true spirit and scope of the invention.

SEQUENCES
Partial sequence of pM9-4 A (biggest plasmid)
Large fragment by sequence walking SEQ ID NO: 10
```
CCTCTCCCCCCACACAACGCCACCTCCCGTCAGCACAACATGTGGTGC
CGGATTCAGCTGCTGATAACACTATATGTTGTGTCATCTCCCTGACCT
GTGATGCGTCGCGCAGGGGCGGAAAACAGCGATATGATGATTTCCTCA
GCGTGGTACACTTCCGGAAAGTTATGAATAGGAAAAAAATCGGATCTG
CCTGAAATGGGCATCCAGTAATTTAATAGCGTGGTTATATGCCTGCTT
ATTATCTGACAGGTGATGATTTATTTAGGGGAAAATAATTCATGCTGA
CAGAGTGTTGTGTTGCCATGCGTAATAACTCTGAGCGACTGTTGCTTC
CGGTATCAGTTGAGTGAGGATTTTCAGACCACCACGTTTTACTGACCA
GTAAAAATTTTTTTTGCCCGCAAGGCTGACAAGTGACTTCTTTTAGGG
AAGGTGCGAACAAGTCCCTGATATGAGATCATGTTTGTCATCTGGAGC
CATAGAACAGGGTTCATCATGAGTCATCAACTTACCTTCGCCGACAGT
GAATTCAGCAGTAAGCGCCGTCAGACCAGAAAAGAGATTTTCTTGTCC
CGCATGGAGCAGATTCTGCCATGGCAAAACATGGTGGAAGTCATCGAG
CCGTTTTACCCCAAGGCTGGTAATGGCCGGCGACCTTATCCGCTGGAA
ACCATGCTACGCATTCACTGCATGCAGCATTGGTACAACCTGAGCGAT
GGCGCGATGGAAGATGCTCTGTACGAAATCGCCTCCATGCGTCTGTTT
GCCCGGTTATCCCTGGATAGCGCCTTGCCGGACCGCACCACCATCATG
AATTTCCGCCACCTGCTGGAGCAGCATCAACTGGCCCGCCAATTGTTC
AAGACCATCAATCGCTGGCTGGCCGAAGCAGGCGTCATGATGACTCAA
GGCACCTTGGTCGATGCCACCATCATTGAGGCACCCAGCTCGACCAAG
AACAAAGAGCAGCAACGCGATCCGGAGATGCATCAGACCAAGAAAGGC
AATCAGTGGCACTTTGGCATGAAGGCCCACATTGGTGTCGATGCCAAG
AGTGGCCTGACCCACAGCCAGTCACCACCGCGGCCAACGAGCATGAC
CTCAATCAGCTGGGTAATCTGCTGCATGGAGAGGAGCAATTTGTCTCA
GCCGATGCCGGCTACCAAGGGGCGCCACAGCGCGAGGAGCTGGCCGAG
GTGGATGTGGACTGGCTGATCGCCGAGCGCCCCGGCAAGGTAAGAACC
TTGAAACAGCATCCACGCAAGAACAAAACGGCCATCAACATCGAATAC
```
-continued
```
ATGAAAGCCAGCATCCGGGCCAGGGTGGAGCACCCATTTCGCATCATC
AAGCGACAGTTCGGCTTCGTGAAAGCCAGATACAAGGGGTTGCTGAAA
AACGATAACCAACTGGCGATGTTATTCACGCTGGCCAACCTGTTTCGG
GCGGACCAAATGATACGTCAGTGGGAGAGATCTCACTAAAAACTGGGG
ATAACGCCTTAAATGGCGAAGAAACGGTCTAAATAGGCTGATTCAAGG
CATTTACGGGAGAAAAAATCGGCTCAAACATGAAGAAATGAAATGACT
GAGTCAGCCGAGAAGAATTTCCCCGCTTATTCGCACCTTCCTTAAGTA
TCATTGCAGCAAAGATGAAATCAATGATTTATCAAAAATGATTGAAAG
GTGGTTGTAAATAATGTTACAATGTGTGAGAAGCAGTCTAAATTCTTC
GTGAAATAGTGATTTTTGAAGCTAATAAAAAACACACGTGGAATTTAG
GAAAAACTTATATCTGCTGCTAAATTTAACCGTTTGTCAACACGGTGC
AAATCAAACACACTGATTGCGTCTGACGGGCCCGGACACCTTTTTGCT
TTTAATTACGGAACTGATTTCATGATGAAAAAAATCGTTATGCTGCGCT
CTGCTGCTGACAGCCTCTTTCTCCACATTTGCTGCCGCAAAAACAGAA
CAACAGATTGCCGATATCGTTAATCGCACCATCACCCCGTTGATGCAG
GAGCAGGCTATTCCGGGTATGGCCGTTGCCGTTATCTACCAGGGAAAA
CCCTATTATTTCACCTGGGGTAAAGCCGATATCGCCAATAACCACCCA
GTCACGCAGCAAACGCTGTTTGAGCTAGGATCGGTTAGTAAGACGTTT
AACGGCGTGTTGGGCGGCGATGCTATCGCCCGCGGCGAAATTAAGCTC
AGCGATCCGGTCACGAAATACTGGCCAGAACTGACAGGCAAACAGTGG
CAGGGTATCCGCCTGCTGCACTTAGCCACCTATACGGCAGGCGGCCTA
CCGCTGCAGATCCCCGATGACGTTAGGGATAAAGCCGCATTACTGCAT
TTTTATCAAAACTGGCAGCCGCAATGGACTCCGGGCGCTAAGCGACTT
TACGCTAACTCCAGCATTGGTCTGTTTGGCGCGCTGGCGGTGAAACCC
TCAGGAATGAGTTACGAAGAGGCAATGACCAGACGCGTCCTGCAACCA
TTAAAACTGGCGCATACCTGGATTACGGTTCCGCAGAACGAACAAAAA
GATTATGCCTGGGGCTATCGCGAAGGGAAGCCCGTACACGTTTCTCCG
GGACAACTTGACGCCGAAGCCTATGGCGTGAAATCCAGCGTTATTGAT
ATGGCCCGCTGGGTTCAGGCCAACATGGATGCCAGCCACGTTCAGGAG
AAAACGCTCCAGCAGGGCATTGCGCTTGCGCAGTCTCGCTACTGGCGT
ATTGGCGATATGTACCAGGGATTAGGCTGGGAGATGCTGAACTGGCCG
CTGAAAGCTGATTCGATCATCAACGGCAGCGACAGCAAAGTGGCATTG
GCAGCGCTTCCCGCCGTTGAGGTAAACCCGCCCGCCCCCGCAGTGAAA
GCCTCATGGGTGCATAAAACGGGCTCCACTGGTGGATTTGGCAGCTAC
GTAGCCTTCGTTCCAGAAAAAAACCTTGGCATCGTGATGCTGGCAAAC
AAAAGCTATCCTAACCCTGTCCGTGTCGAGGCGGCCTGGCGCATTCTT
GAAAAGCTGCAATAACTGACGATGAGGCCCAGGATATTGGGCCTCCTT
TCTTTCTCTTTTTTTCCTGTTGTCATCTACACTTAACAAAAATACAGC
AAGGAAAATCCCATGCGCATTTTGCCCGTCGTTGCTGCAGTTACGGCT
GCATTCCTGGTTGTCGCGTGTAGCTCCCCGACACCGCCGAAAGGCGTT
ACCGTGGTAAATAACTTTGATGCCAAACGCTATCTGGGAACCTGGTAT
```

```
GAAATTGCGCGCTTCGACCATCGTTTCGAGCGCGGATTGGATAAAGTG
ACCGCAACATACAGCTTGCGCGACGACGGCGGCATCAACGTTATTAAC
AAGGGCTATAACCCTGACAGGGAGATGTGGCAGAAAACGGAAGGGAAA
GCCTATTTCACCGGCGACCCAAGCAGAGCCGCGCTTAAGGTTTCTTTT
TTCGGCCCCTTCTATGGCGGGTATAACGTAATTGCACTCGACCGGGAA
TATCGTCACGCGCTGGTTTGTGGTCCGGATCGCGACTACCTGTGGATC
CTTTCACGGACCCCTACTATTTCAGATGAAATGAAACAGCAAATGTTA
GCCATCGCGACCCGGGAAGGGTTTGAAGTGAATAAACTGATTTGGGTG
AAACAGCCTGGCGCTTAGTGAGTGCTCAGCTTCAGACCAATAATGCCA
GCAACGATCAGCCCAAGGCTCAGCAAACGTGCCGGGCTGGCAGACTCA
CCCAGCAGCAAAATCCCTGTAATGGCCGCCCCAACAGCGCCAATACCG
GTCCAGACCGCATAAGCGGTTCCTACAGGCAACGTGCGCATTGCCCAA
GAGAGCATGGCGATACTGACGATCATCGCCGCAATAGTGATAATGCTT
GGCGTAAGACGCGTAAAACCGTGGGTGTATTTCAGGCCAATCGCCCAG
ACAACTTCGAGCAAACCTGCAATTAATAAAACGATCCAGGACATATCA
GGCTCCAGAACAATGGGCCGTCCCCGGTGAAAGAAGCGTTTGCAGGT
CGTCCTGCAAAGCTAATGTGTGAAATGGCATTTTTGCCCGGAAGAAAA
TGAATTTCAACCTTTTTATTCACCGCCTGCTAAAAGCAAGAATTAAGC
ATAATTAGCGGCGTAGTTCCCGCATTATTACCGGAAATCGATTATTCC
CCGGTATCTGGTAACTGGCGCTCCCTTCCTTCTGGCCTGATGTATAGG
CTCAGCGAACTCTCTGTTCTCAGCTACGAAGCTGTCGTGTGTAGAT
AATGTGTTTGTTGAAGATACTCCTTATGGTGGAGCGGGTGAATATAGT
TTGCATAAAAACGCAGCTATGTTGGGAGTAAAAGCACTGCGGTTATCA
CGAGAACTGAGAATGTTATGTGGCCTCCCTCTGCACGGCCTTTCCGAT
ACACTATCGCCAACGAGGTTGGTATTGTTGAAAGCCAGAGGTAAAACA
CTCCAAAAGGAGTACGAAATGGTAAAGAAGTCTAAAAAGACCGAGCAA
GAGATTGAGGATTTCATAAAGGGGACATCATGAGTGGTCCACAATTGC
TTTCCCTGCCTGGTTCTTTTTTAACGCCTCCGGCAACATTACCTGTTG
CCATTGATTACCCGGCTGCGCTGGCACTCCGCCAGATGTCGATGGTTC
ATGATGAACTGCCAAAATACCTGCTGGCCCCTGAAGTGAGCGCCCTGC
TCCATTACGTGCCGGATCTGCGCCGCAAAATGCTGCTGGCCACACTGT
GGAACACCGGTGCGCGCATTAATGAAGCACTGGCGCTGACGCGGGGG
ATTTTTCGCTCACGCCTCCGTATCCGTTTGTGCAGCTGGCCACTCTGA
AGCAGCGGACAGAAAAGCCGCCAGGACGGCAGGAAGGATGCCCGCCG
GTCAGCAGACTCACCGTCTGGTTCCGCTCTCCGACGCCTGGTACGTCA
GCCAGCTGCAGACGATGGTGGCCACACTGAAAATCCCCATGGAACGGC
GTAATAAACGAACAGGCAGGACAGAGAAAGCGCGGATCTGGGAAGTGA
CGGACAGAACGGTCAGGACCTGGATTGGGGAGGCGGTTGCCGCCGCTG
CCGCTGATGGTGTGACGTTCTCTGTCCCGGTCACGCCACATACGTTCC
GCCATTCCTATGCGATGCATATGCTGTATGCCGGTATACCGCTGAAGG
TCCTGCAGAGTCTGATGGGGCATAAGTCCATCATCTCAACGGAGTCTA
CACAACGTGTTTGCACTGGATGTGGTTGCACGGCACCGGGTGCAGTTT
TCGATGCCTGAGTCCGATGCGGTGTCTATGCTCAAAAGAATTCCATAA
GCTCTGACTTTTTTAAATCCCTTTCGGATATCTCATGKATATATTATC
GGTATTTCATATTCTGTTGACATGCAGGACCGGTATAGAGTAAAAAAA
CATCTGTTGAGTACCTCTTGGATATCCGAAAGGTGTCTTATGGGGTCT
TTMTGGRTATTACATGTGGATTCTGGAGATACACTATGCCTGTTATTG
CTAATACGCATCCCAAAGGYGGTGTGGGTAASACAACTTCATCCRTAA
ACATAGKTGGTGAAATGAAGTCTGATACAGTTGATCTGGATACTCATA
CCGGGCTTTCTATCATTCTGGGGCTGAGACCTGATGGAAAAGAAATTT
CCGTGAAAGTACCCAAAACAGAGGATGAGTTAATCGATATTATGACTC
CCTACAAGAACAACCATAAGACGTTACTTATTGACTGTGGGGATTTGA
CTTCATATCTTACCCGTACTGCGATTGCCTTTGCCGACTGAGTTATTG
GCCCTTCAAAAGACTCCCTGACTGAACGTATTGTCTGATGCATTTGAT
GGATACTGGACGAAATCGCTCTATCATGGGGACCGATMTAACTGCTCA
CCTGTATCTCTGTAAAGTTAATCCTAACAAGAAGAAATTCCCTAAGCT
TGATGCAATCCTGCCATCGTTCAAACATCTGAAGCTGATGAAGAGCCG
CATTTCTGCTCGTGCAGAATTTGATGATGTCATTGAKACTGGRATGGG
AATCACTGAGYCTGTTCATGGGCGCTATTCKGCAGGAGGTAAGGAAGT
TATTGCCCTGATCGAAGAAATTAATCATCTGATTGAAAATMACAAACA
GTAAGGTGTATCTATTGGGTATCCATATAGTATMCTTTGGGCTTTTAA
TGGATATCTTTTARGTATCTAACAAACATCCTGGGTTAYCTCATGAGC
AAAGCGAAATTT (1..6252)
```

Nucleic acid sequence of pM9-4 A SEQ ID NO: 11
```
tagaatttcggcatccacaaccaatggcaggaagcccgatgcaaaaat
ttttaaggagagctcttttaatgaaaattgctcagcaattactggagg
ccgttctgcaatttatgaatgcatctgcaatgactcaggtgctgacgt
tgatattcctggctctgataatacaggtactgaaaacattaattacgg
cgtggatagtaagaaaaccatcttcaggagagatggttttagaccgga
aacctgactctgccgggcgtaaggatcactgcaggcagctgtctcaac
aaaggaaaaaacatggctgactggtttattgcaactgaaggtgtgaag
gtggtgaaagatagtgccagcctgtggccgcagatcatcacggcggtt
ttgtctgccggtactgcatttggtggtgtgtggtacgggcagtggcgg
ataacacagcgagaggaggaagctgcaacagcgaagctggtcagcgaa
cgtctcttattgccacggagctggttttttctgctggagaggtttgcg
cagcgttgtgctccagcagcaacagcaactgtggagcacgatcaggat
ggcagaggagaagctgagttcttattcctagattctacgtcagtactt
caaaaagcataatcaaagccttgataaatatgcattccttcgaaattc
agctttcacccattgggtgaaagaaaagtgctcaaaaatatgttaaat
tatcagcttttatgactcgatatatggtaaaataatagtaagaaaagt
agtaaaaaggggttctaattatgattaataaaattgatttcaaagcta
```

-continued agaatctaacatcaaatgcaggtcttttctgctccttgagaatgcaa aaagcaatgggattttgattttattgaaatgacctcgtatttgata atgactcaacaaataaaatcaagatgaatcatataaagaccatgctct gcggtcacttcattggcattgataagttagaacgtctaaagctacttc aaaatgatccctcgtcaacgagtttgatatttccgtaaaagaacctg aaacagtgtcacggtttctaggaaacttcaacttcaagacaacccaaa tgtttagagacattaattttaaagtctttaaaaaactgctcactaaaa gtaaattgacatccattacgattgatattgatagtagtgtaattaacg tagaaggtcatcaagaaggtgcgtcaaaaggatataatcctaagaaac tgggaaaccgatgctacaatatccaatttgcatttgcgacgaattaa aagcatatgttaccggatttgtaagaagtggcaatacttacactgcaa acggtgctgcggaaatgatcaaagaaattgttgctaacatcaaatcag acgatttagaaattttatttcgaatggatagtggctactttgatgaaa aaattatcgaaacgatagaatctcttggatgcaaatatttaattaaag ccaaaagttattctacactcacctcacaagcaacgaattcatcaattg tattcgttaaaggagaagaaggtagagaaactacagaactgtatacaa aattagttaaatgggaaaagacagaagatttgtcgtatctcgcgtac tgaaaccagaaaagaaagagcacaattatcacttttagaaggttccg aatacgactacttttctttgtaacaaatactaccttgctttctgaaa aagtagttatatactatgaaaagcgtggtaatgctgaaaactatatca aagaagccaaatacgacatggcggtgggtcatctcttgctaaagtcat tttgggcgaatgaagccgtgtttcaaatgatgatgctttcatataacc tattttgttgttcaagtttgattccttggactcttcagaatacagac agcaaataaagacctttcgtttgaagtatgtatttcttgcagcaaaaa taatcaaaccgcaagatatgtaatcatgaagttgtcggaaaactatc cgtacaagggagtgtatgaaaatgtctggtataataagaatatcatc aataaaattgagtgttgctctgtggataacttgcagagtttattaagg a (1..2113)

Additional sequenced fragments from pM9-4A
Colicin 1Forward SEQ ID NO: 12:
TGACATTAACAAAAAATTAATGCAAAAGATCGTGCAGCGATTGCCGC

AGCCCTTGAGTCTGTGAAGCTGTCTGATATATCGTCTAATCTGAACAG

ATTCAGTCGGGGACTGGGATATGCAGGAAAATTTACAAGTCTTGCTGA

CTGGATCACTGAGTTTGGTAAGGCTGTCCGGACAGAGAACTGGCGTCC

TCTTTTTGTTAAAACAGAAGCCATTATAGCAGGCAATGCCGCAACGGC

TCTTGTTGCACTGGTCTTCAGTATTCTTACCGGAAGCGCTTTAGGCAT

TATCGGGTATGGTTTACTGATGGCTGTCACCGGTGCGCTGATTGATGA

ATCGCTTGTGGAAAAGCGAATAAGTTCTGGGGTATTTAAATAAAATA

TAAGACAGGCTGTCTATCTTACAGACAGCCTTTTTATAATAACAGAAA

GAATATATATCATACTTAACGGAAGAGATAATATGAAAACAGTACCCG

TATAAACAGCAAGCAATCCCATTTTCCCAGGTGTATCAGCAAAAAAAC

CGCTGTTCCAGAAATCAGGCCGGGTAAATTTCAGAGCTGTATCTTCAA

TATACCATTTTGCAACCGGATACAAAACCATTCCGCAGAGAGAAATAC

ACCAGAACAGTAATCTGTATTTAAAATCATAATCCCATGACATATACA

GCATATATCCCCCCGTCACCCATCCCCACCACATATTATTAAAATAAT

ATTTTCTGTTCATCTGCCTGTTTTCCTTTCTTTTGCACTTTTGTCAGT

GTACTGATGCATGACAACACAACCACAGCATGATAATAATAATCAATA

ACAATAAGC (1..825)

Colicin1 Reverse SEQ ID NO: 13
GCCTTGGCCGTTTACTCCTGTCGCTTATTGAAGATGCAGGGCTGAATA

AACTGGATTCCCTGGCTAATCCCCGTATCCGGACTAATTATCGTGAGT

GTCTTGATGCCATACGGCAGGTTACACTACAGCAGGAGTATATTCGGG

GAAGAGCCTTATCTGAAATTATCCATTTCCGGCCAGGAATGTCTGAAA

GGTCTCAGGAGCGGTTAATGGAAACGCTGGAGAATTCAGAACGACACT

GGCCTGCCAGAAGAAAGCATATGTTCTTTCAGATTTTTATGGCGCAGC

ACATCTGTCGTGATGCTGTGGAAATTCACTGGGCGAACGGTAATATTC

AGGTCATCAGACCTGTGCGGGGGATCAGTATTAATGGTGAAGCGCAGG

GCGGAATACGTCCCCCTTACTGGGTTATTCTTGCTTTTTGCCGGAGTG

CCGATGGCAGAATCATCTGCAGTGAAGGGTATGCTCATGCTCTTTATC

AACTGACATGTCCGGTGCCTGTGGACAGCAAACTGGAACGAAACACGC

TCACTGCTCTTCTGAATGTGGCCAGCTGGCTTAAAAGAAAGCCAGGTA

CGCCGGAATTAAGTCTGGAAAGGCCCCTGTTTGATACAGAAGTTTATG

TTAATGGTGAAAAGAAATATGTACTGCCGGATTTCATTGTCACAGCAA

GGGCTCCTGACGGAAAGACGGCCAGAGTGGTCATCGAAACGATGGGAT

ATGAAGACAGTGATTACTGCGCGAGAAAATCCAGGCAGCATACCGGCA

TGAAGCAGATTGGTGTTCTGCATACCGATCCACCGAAATGGCTGGATA

ACGATCATCCCCCTTTTAAGAAACATATGTACGGTGTTTTTATGCATC

TCAGGTACTGAGATATTTTGTGGCTCAGTTCTGTAACTTTTCCCGTAA

CATTGTCTGTTGTTACGGGAAAGTCCGGTTTTTGTATTGCACCAGAGA

ATACCCAGACTGTGATGCTGCCACAGCGTCAGCAGGCTTTCTGAACGG

TGTAACATCACTTCATGTTAATGATAATCACTATCATCAAATCTTGAC

ATGCCATTTTCTCCTTAATAAATTAATACTGTATATGTATCCATATGC

GTAAGCAGTTAATTCATTTGTTTTCCTCAGAGGATGAAGGAGATACCG

AATGTCTGACCCTGTACGTATTACAAATCCCGGTGCAGAATCGCTGGG

GTATGATTCAGA (1..1212)

IS2001 Forward SEQ ID NO: 14
GAAGCCTCGCCCGACAGGGCGGGGAGCAGTCACGGGTGGTCTGGAGGT

CATGCGGCGTGTCCTCTGCACTCGCCGGAATAAGGAAGTCGCCGGCGG

CTCCGCTTTTACCCGGCCATGCGGGGCATGGCCTTGTGGGTTTTCAGC

TCTGTGGCCTCAGCGTCGTGTGCGGGCTGTGCCGTGCCTCCA (1..186)

IS2002 Reverse SEQ ID NO: 15
TGGTGCGGGCGTTTTCCATCACTGTCATCATTTGACCGGTTTTTCTGG

CAGGAGGAACCACTCTGGCGGCTGATTTTTGAAGCCGGTGAGGCCGGT

-continued

```
CGTGGTGCACCGGTACAGATACGTGCACTTGAGCAGTGGATGATCCCG

AACAAGCTGGAGAACGCAATATGATGAAATCAGCGAAAAGCCGCCGAG

AACCCTCGCCCAATGCGGGTGGGGAGGAAAGGCGGAAAAGCCCGAAGG

GCTTTAAAAATATTATTACGGTGTTAGCATAAAAACCTGTACCAATG (1..287)
```

ParE1Forward SEQ ID NO: 16
```
GGTCGTGTGGAAGGAACCCGGGAACTGGTTATTCACCCCCATTTTGTT

CTGGTTTATGAGGTCGACAGCCAGTGGGGAAAAGTGTATGTCCTGCGC

GTGTTGCATACCGCACAGAAGTGGCCATAAAATTCCAGTCAGGAATAA

TACTTTTCATTTTTAGTTTACTGCTCCCCCAGTAAGAGCGATATATTC

CGAACAGTCTTGTCTGGGAGGTATGGTGCAGTCAGCGAAGAACCGCCG

AGAATCCTCGCCCAATGCGGGCGGGGAGCAGTCACCGGAGTCTTCGCC

ACCCGCCCTCTGTGCACTGACCGGGTGATCCTGTCAGTGAGCGTGGTT

CTGCCACTTCATCCGAATTCTTTCTTCCAGTTTGCTATGCAATCCGCC

TCCGATCCACTGGCTGACCAGAGCTGCTGTTGCAAATGAACAGAAAGT

CAAGGCGAATCCATGTTTAAACGTCTCCGGTAGTTCCTGGCCGGCGTG

CTGAGTGATGATGGAAAACCCTATATATATAATAAAGGTACAAAAAAT

TCCTGTGTGGGCGAGCCAGGCAAACCATTTGGCCACCCTGTATAACCC

GTATTTCAATGGCATCTCCCGTTTAATATCATGAATAATCATTGTATC

TATCTTGTGGGTCAGAGATTGAAATTTTGTAAATATCATAAGTCCTTA

GTCCATCTAAAGTGAGATTTACCGTATCTGAATATATCAAAATGCTAA

GGCAGAATCCCCGGAAATTTGTGTATTACTTCTGTAGCAGACACGGCA

AAATCGTTGCATTACAGGTGCATCTGCTGGGCATCTGTTTATCGATG

CATCAGATTTAATGTCTGACAGTTACTTTTCTGTATCACCCACACTCT

CTGCTTTTTCATTGCTACTGTCATATTTATGTCTGTTGCGCGGTTTTA

TCTGTGTATATAAAATACATCTGTATTCATTGTTTTCTAAAAATTTGC

GTATGTTGATAAAAAATCCGATTTCTTATTTCCATATTGGCACGTTTT

TATTTTCAGGAAAAAAACGTCATCTTCTGGAATACTGGAAAGCAGAAG

TTATCATGCGGGATAAGTTTGTTTTTCA (1..1084)
```

ParE1 Reverse SEQ ID NO: 17
```
CCACATAAATCCGCAAACAAAAAACTTTAAGAAGCTGCAAACCTGAAA

CAGCAAACCTGCAATATAGTCTTAACCCCATTATTTAATCCCCTGCGT

TGCTTCGCCGCAGGGAAAGTCTTTATCTCTGAAACCACTGTGAACAAA

CACAAAGAGGCCTTCGCTTGCAGCGGCCAAGGCCGCGCCGCTCAGAAT

CTAAAAGCACCTCCCACGCTAACGCGCGGGCCCCGAACCTCACCGTTC

TGAAACCACCGCGAAAACATCAGGAATAAAAAACACCACACAAACGCA

GCACCGTGCCCACCCCTCATAACTGAAAAGCGAGGCCGCCCCCGCCCG

AAGGGCGGGAACAACATCGCTTTTAATTATGAATGTTGTAACTACATT

GTCATCGCTGCCAGTCTTCTGGCTGGAAGTCCTCAGTACACGCTCGTA

AGCGGCCCTCACGGCCCGCTAACGCGGAGATACGCCCCGACTTCGGGT

AAACCCTCGTCGGGACCACTCCGACCGCGCACAGAAACTGTCTCATGG

CTGAAAGCGGGTATGGCTTAGCAGGGCTGGGGATGGGTAAGGTGAAAT

CTATCAATCAGTACCGGCTGACGCCGGGCTTCGGCGGTTTTACTCCGG

TATCACATGTAACCACAGCGTGCCGCCTTCCATGCCGCTGGCGCGGCA

TATCCTGGTGACGATATCTGAATCGTTATATACTGTGTATACGTAGTA

ATGACGAGGTGATAAATGGCACAGGTTAATATGAGTTTAAGAATCGAC

GCTGAACTGAAGGATGCTTTTATGGCCGCTGCAAAAAGCATGGACCGT

AATGGCTCTCAGTTAATTCGGGATTTTATGCGCCAGACCGTTGAACGG

CAGCATAATACCTGGTTCCGTGAACAGGTTGCGGCAGGACGTCAGCAA

CTCGAGCGCGGCGATGTGCTTCCCCATGACATGGTCGAATCTTCTGCC

GCTGCATGGCGGGATGAAATGAGCAGGAAGGTTTCCGATAAATGATGG

AGATATTCTGGACCATGCTGGCCAGCCAGGACAGGAAGCGCATTCGTG

AGTAC (1..1061)
```

TraA1 Reverse SEQ ID NO: 18
```
GAGATACTGATATTGTGCTTTTGTCAGCCATATGCTGGAAGCCGCATT

CAGCTCTTCCCTGGCTCCCGGATTTAGCACAGGGTCCGGGTAAATCTT

CATTAATCCATCAACAATATCTTTATTGACGGGTTTTATTTCACCGCC

AAACTTCACGAAATCAATGAAGGCGCTATGGCGACGTAATGCCGATAC

TGGTTGAATGTCAAAATTAGCCAGAATAAAAAAGTACCCTGGAAAAAT

AGCGAATATTCTTTCACGGTAACAGCACCTGGAGTCTGCCCGTCTTAT

CTTTCTTGTTATTAATGGAGTCCATGGTACGACGTTTTGCTCATTCAG

CCATGAGAATAAAGATTCTCTGTTTTTGCCGGCTGTATTATATTGCGC

AAGATACCAGTTCCGGTTATTCAGGTGTTCTATATTCACGAAGTTCAA

CGCTCCGCGCAAAACCGATCCATGATGGACGATTTTGCGATGTCAGGC

GAATATGCTAAATCATATGTCTGAAGCAGTATCCAGCCCGTATCTGGA

TAAACTGCAGTTCTGACAGGCATATAACCAGCAGACTCTAGTACGTTC

TGTATCGGTGATTTGGCGAACTCACAGATAAAGAACGGCTAAGCACTA

ATATCAGCAATACAGTGGCACAGTATTGTGATACGCGAAATAAAACAT

CAGCACGTCAGTTCAGAGTAAGATCGCCATATATCGGGCATGAGCCAG

ATACAAATAACTGGGACACCGTCTGAAGTGATTTGCTTTATTAAAGTA

ACTTGTGCTTGGTGTTTATGTTTATCAATTTGGGATCGCCTGTAAAGT

GCAAAATGCAATTTCCATGAAAGTGTCCCCTTTAATGGGACACCTGT

TCACATTTTTTCGTTTTCTTTAGCTGTATTGCTAATCATGAAAACGAA

AGTTCGCATCAGCACAGCAGAGCGAAGTGCATCATATCCTTCCAGATT

TAAATTC (1..967)
```

What is claimed is:

1. A feed composition comprising a probiotic treatment, wherein said probiotic treatment comprises *Lactobacillus crispatus* WZ-12 or a derivative thereof, wherein said *Lactobacillus crispatus* WZ-12 derivative improves one or more probiotic qualities in a subject compared to a parental *Lactobacillus crispatus* WZ-12 strain; and an ingestible food product; wherein the probiotic treatment reduces antibiotic resistant *Escherichia coli* in a gut microbiota of the subject.

2. The composition of claim 1, wherein the composition comprising *Lactobacillus crispatus* WZ-12 or a derivative thereof comprises *Lactobacillus crispatus* WZ-12 or a derivative thereof in an amount from $1\times10^4$ to $1\times10^7$ colony forming units per milliliter.

3. The composition of claim 1, wherein the subject is a poultry or porcine subject.

4. The composition of claim 1, wherein the ingestible food product comprises a feedstuff.

5. The composition of claim 1, wherein the ingestible food product comprises a nutritional supplement.

6. The composition of claim 1 further comprising one or more probiotic bacteria comprising *Lactobacillus salivarius* 1-14 or a derivative thereof, *Lactobacillus salivarius* 1-31 or a derivative thereof and *Lactobacillus reuteri* 2-2 or a derivative thereof; wherein said derivative of *Lactobacillus salivarius* 1-14, *Lactobacillus salivarius* 1-31 or *Lactobacillus reuteri* 2-2, improves one or more probiotic qualities compared to a parental strain of the *Lactobacillus salivarius* 1-14, *Lactobacillus salivarius* 1-31 or *Lactobacillus reuteri* 2-2.

7. The composition of claim 1, wherein the *E. coli* is multidrug resistant.

8. The composition of claim 1, wherein the *E. coli* is ampicillin resistant.

9. A feed composition comprising *Lactobacillus crispatus* WZ-12 or a derivative thereof and *E. coli* strain M9-4-1 or a derivative thereof and an ingestible food product; wherein the composition comprises *Lactobacillus crispatus* WZ-12 or a derivative thereof and *E. coli* strain M9-4-1 or a derivative thereof in an amount sufficient for use as a probiotic treatment of a subject, wherein the probiotic treatment reduces antibiotic resistant *Escherichia coli* in a gut microbiota of the subject.

* * * * *

SEQUENCE LISTING

<160> NUMBER OF SEQ ID NOS: 18

<210> SEQ ID NO 1
<211> LENGTH: 19
<212> TYPE: DNA
<213> ORGANISM: Artificial Sequence
<220> FEATURE:
<223> OTHER INFORMATION: SYNTHETIC CONSTRUCT

<400> SEQUENCE: 1
gacagcctct ttctccaca                                                19

<210> SEQ ID NO 2
<211> LENGTH: 18
<212> TYPE: DNA
<213> ORGANISM: Artificial Sequence
<220> FEATURE:
<223> OTHER INFORMATION: SYNTHETIC CONSTRUCT

<400> SEQUENCE: 2
tggaacgaag gctacgta                                                 18

<210> SEQ ID NO 3
<211> LENGTH: 19
<212> TYPE: DNA
<213> ORGANISM: Artificial Sequence
<220> FEATURE:
<223> OTHER INFORMATION: SYNTHETIC CONSTRUCT

<400> SEQUENCE: 3
cgcccgccgc gcgcggcgg                                                19

<210> SEQ ID NO 4
<211> LENGTH: 19
<212> TYPE: DNA
<213> ORGANISM: Artificial Sequence
<220> FEATURE:
<223> OTHER INFORMATION: SYNTHETIC CONSTRUCT

<400> SEQUENCE: 4
gcggggcggg ggcacgggg                                                19

<210> SEQ ID NO 5
<211> LENGTH: 19
<212> TYPE: DNA
<213> ORGANISM: Artificial Sequence
<220> FEATURE:
<223> OTHER INFORMATION: SYNTHETIC CONSTRUCT

<400> SEQUENCE: 5
ggcctacggg aggcagcag                                                19

<210> SEQ ID NO 6
<211> LENGTH: 17
<212> TYPE: DNA
<213> ORGANISM: Artificial Sequence
<220> FEATURE:
<223> OTHER INFORMATION: SYNTHETIC CONSTRUCT

<400> SEQUENCE: 6
attaccgcgg ctgctgg                                                  17

<210> SEQ ID NO 7
<211> LENGTH: 18
<212> TYPE: DNA
<213> ORGANISM: Artificial Sequence

```
<220> FEATURE:
<223> OTHER INFORMATION: SYNTHETIC CONSTRUCT

<400> SEQUENCE: 7
gccgttgatg atcgaatc                                                     18

<210> SEQ ID NO 8
<211> LENGTH: 19
<212> TYPE: DNA
<213> ORGANISM: Artificial Sequence
<220> FEATURE:
<223> OTHER INFORMATION: SYNTHETIC CONSTRUCT

<400> SEQUENCE: 8
gcgtattggc gatatgtac                                                    19

<210> SEQ ID NO 9
<211> LENGTH: 25
<212> TYPE: DNA
<213> ORGANISM: Artificial Sequence
<220> FEATURE:
<223> OTHER INFORMATION: SYNTHETIC CONSTRUCT

<400> SEQUENCE: 9
agttcagcat ctcccagcct aatcc                                             25

<210> SEQ ID NO 10
<211> LENGTH: 6252
<212> TYPE: DNA
<213> ORGANISM: Artificial Sequence
<220> FEATURE:
<223> OTHER INFORMATION: SYNTHETIC CONSTRUCT

<400> SEQUENCE: 10
cctctccccc cacacaacgc cacctcccgt cagcacaaca tgtggtgccg gattcagctg        60
ctgataacac tatatgttgt gtcatctccc tgacctgtga tgcgtcgcgc aggggcggaa       120
aacagcgata tgatgatttc ctcagcgtgg tacacttccg gaaagttatg aataggaaaa       180
aaatcggatc tgcctgaaat gggcatccag taatttaata gcgtggttat atgcctgctt       240
attatctgac aggtgatgat ttatttaggg gaaaataatt catgctgaca gagtgttgtg       300
ttgccatgcg taataactct gagcgactgt tgcttccggt atcagttgag tgaggatttt       360
cagaccacca cgttttactg accagtaaaa attttttttg cccgcaaggc tgacaagtga       420
cttcttttag ggaaggtgcg aacaagtccc tgatatgaga tcatgtttgt catctggagc       480
catagaacag ggttcatcat gagtcatcaa cttaccttcg ccgacagtga attcagcagt       540
aagcgccgtc agaccagaaa agagattttc ttgtcccgca tggagcagat tctgccatgg       600
caaaacatgg tggaagtcat cgagccgttt taccccaagg ctggtaatgg ccggcgacct       660
tatccgctgg aaaccatgct acgcattcac tgcatgcagc attggtacaa cctgagcgat       720
ggcgcgatgg aagatgctct gtacgaaatc gcctccatgc gtctgtttgc ccggttatcc       780
ctggatagcg ccttgccgga ccgcaccacc atcatgaatt ccgccacct gctggagcag        840 catcaactgg cccgccaatt gttcaagacc atcaatcgct ggctggccga agcaggcgtc       900
atgatgactc aaggcacctt ggtcgatgcc accatcattg aggcacccag ctcgaccaag       960
aacaaagagc agcaacgcga tccggagatg catcagacca agaaaggcaa tcagtggcac      1020
tttggcatga aggcccacat tggtgtcgat gccaagagtg gcctgaccca cagcctagtc      1080
accaccgcgg ccaacgagca tgacctcaat cagctgggta atctgctgca tggagaggag      1140
```

```
caatttgtct cagccgatgc cggctaccaa ggggcgccac agcgcgagga gctggccgag      1200
gtggatgtgg actggctgat cgccgagcgc cccggcaagg taagaacctt gaaacagcat      1260
ccacgcaaga acaaaacggc catcaacatc gaatacatga agccagcat ccgggccagg       1320 gtggagcacc catttcgcat catcaagcga cagttcggct tcgtgaaagc cagatacaag      1380
gggttgctga aaaacgataa ccaactggcg atgttattca cgctggccaa cctgtttcgg     1440
gcggaccaaa tgatacgtca gtgggagaga tctcactaaa aactggggat aacgccttaa     1500
atggcgaaga aacggtctaa ataggctgat tcaaggcatt tacgggagaa aaaatcggct     1560
caaacatgaa gaaatgaaat gactgagtca gccgagaaga atttccccgc ttattcgcac      1620
cttccttaag tatcattgca gcaaagatga aatcaatgat ttatcaaaaa tgattgaaag      1680
gtggttgtaa ataatgttac aatgtgtgag aagcagtcta aattcttcgt gaaatagtga     1740
tttttgaagc taataaaaaa cacacgtgga atttaggaaa aacttatatc tgctgctaaa     1800
tttaaccgtt tgtcaacacg gtgcaaatca aacacactga ttgcgtctga cgggcccgga     1860
cacctttttg cttttaatta cggaactgat ttcatgatga aaaaatcgtt atgctgcgct     1920
ctgctgctga cagcctcttt ctccacattt gctgccgcaa aaacagaaca acagattgcc     1980
gatatcgtta atcgcaccat caccccgttg atgcaggagc aggctattcc gggtatggcc     2040
gttgccgtta tctaccaggg aaaacctat tatttcacct ggggtaaagc cgatatcgcc      2100
aataaccacc cagtcacgca gcaaacgctg tttgagctag gatcggttag taagacgttt    2160
aacggcgtgt tgggcggcga tgctatcgcc cgcggcgaaa ttaagctcag cgatccggtc     2220
acgaaatact ggccagaact gacaggcaaa cagtggcagg gtatccgcct gctgcactta     2280
gccacctata cggcaggcgg cctaccgctg cagatccccg atgacgttag ggataaagcc     2340
gcattactgc attttatca aaactggcag ccgcaatgga ctccgggcgc taagcgactt     2400
tacgctaact ccagcattgg tctgtttggc gcgctggcgg tgaaaccctc aggaatgagt    2460
tacgaagagg caatgaccag acgcgtcctg caaccattaa aactggcgca tacctggatt     2520
acggttccgc agaacgaaca aaaagattat gcctggggct atcgcgaagg gaagcccgta    2580
cacgtttctc cgggacaact tgacgccgaa gcctatggcg tgaaatccag cgttattgat     2640
atggcccgct gggttcaggc caacatggat gccagccacg ttcaggagaa aacgctccag    2700
cagggcattg cgcttgcgca gtctcgctac tggcgtattg cgatatgta ccagggatta     2760 ggctgggaga tgctgaactg gccgctgaaa gctgattcga tcatcaacgg cagcgacagc     2820
aaagtggcat tggcagcgct tcccgccgtt gaggtaaacc cgcccgcccc cgcagtgaaa     2880
gcctcatggg tgcataaaac gggctccact ggtggatttg gcagctacgt agccttcgtt     2940
ccagaaaaaa accttggcat cgtgatgctg gcaaacaaaa gctatcctaa ccctgtccgt     3000
gtcgaggcgg cctggcgcat tcttgaaaag ctgcaataac tgacgatgag gcccaggata    3060
ttgggcctcc tttctttctc ttttttttcct gttgtcatct acacttaaca aaaatacagc   3120
aaggaaaatc ccatgcgcat tttgcccgtc gttgctgcag ttacggctgc attcctggtt    3180
gtcgcgtgta gctccccgac accgccgaaa ggcgttaccg tggtaaataa ctttgatgcc    3240
aaacgctatc tgggaacctg gtatgaaatt gcgcgcttcg accatcgttt cgagcgcgga    3300
ttggataaag tgaccgcaac atacagcttg cgcgacgacg gcggcatcaa cgttattaac    3360
aagggctata accctgacag ggagatgtgg cagaaaacgg aagggaaagc ctatttcacc    3420
ggcgacccaa gcagagccgc gcttaaggtt tcttttttcg gccccttcta tggcgggtat    3480
aacgtaattg cactcgaccg ggaatatcgt cacgcgctgg tttgtggtcc ggatcgcgac    3540
```

```
tacctgtgga tcctttcacg gacccctact atttcagatg aaatgaaaca gcaaatgtta    3600
gccatcgcga cccgggaagg gtttgaagtg aataaactga tttgggtgaa acagcctggc    3660
gcttagtgag tgctcagctt cagaccaata atgccagcaa cgatcagccc aaggctcagc    3720
aaacgtgccg ggctggcaga ctcacccagc agcaaaatcc ctgtaatggc cgccccaaca    3780
gcgccaatac cggtccagac cgcataagcg gttcctacag gcaacgtgcg cattgcccaa    3840
gagagcatgg cgatactgac gatcatcgcc gcaatagtga taatgcttgg cgtaagacgc    3900
gtaaaaccgt gggtgtattt caggccaatc gcccagacaa cttcgagcaa acctgcaatt    3960
aataaaacga tccaggacat atcaggctcc agaacaatgg ggccgtcccc ggtgaaagaa    4020
gcgtttgcag gtcgtcctgc aaagctaatg tgtgaaatgg catttttgcc cggaagaaaa    4080
tgaatttcaa cctttttatt caccgcctgc taaaagcaag aattaagcat aattagcggc    4140
gtagttcccg cattattacc ggaaatcgat tattccccgg tatctggtaa ctggcgctcc    4200
cttccttctg gcctgatgta taggctcagc gaactctctg ttctcagcta cgaagctgtc    4260
gtgtgtgtag ataatgtgtt tgttgaagat actccttatg gtggagcggg tgaatatagt    4320
ttgcataaaa acgcagctat gttgggagta aaagcactgc ggttatcacg agaactgaga    4380
atgttatgtg gcctccctct gcacggcctt tccgatacac tatcgccaac gaggttggta    4440
ttgttgaaag ccagaggtaa aacactccaa aaggagtacg aaatggtaaa gaagtctaaa    4500
aagaccgagc aagagattga ggatttcata aaggggacat catgagtggt ccacaattgc    4560
tttccctgcc tggttctttt ttaacgcctc cggcaacatt acctgttgcc attgattacc    4620
cggctgcgct ggcactccgc cagatgtcga tggttcatga tgaactgcca aaatacctgc    4680
tggcccctga agtgagcgcc ctgctccatt acgtgccgga tctgcgccgc aaaatgctgc    4740
tggccacact gtggaacacc ggtgcgcgca ttaatgaagc actggcgctg acgcgggggg    4800
attttttcgct cacgcctccg tatccgtttg tgcagctggc cactctgaag cagcggacag    4860
aaaaagccgc caggacggca ggaaggatgc ccgccggtca gcagactcac cgtctggttc    4920
cgctctccga cgcctggtac gtcagccagc tgcagacgat ggtggccaca ctgaaaatcc    4980
ccatggaacg gcgtaataaa cgaacaggca ggacagagaa agcgcggatc tgggaagtga    5040
cggacagaac ggtcaggacc tggattgggg aggcggttgc cgccgctgcc gctgatggtg    5100
tgacgttctc tgtcccggtc acgccacata cgttccgcca ttcctatgcg atgcatatgc    5160
tgtatgccgg tataccgctg aaggtcctgc agagtctgat ggggcataag tccatcatct    5220
caacggagtc tacacaacgt gtttgcactg gatgtggttg cacggcaccg ggtgcagttt    5280
tcgatgcctg agtccgatgc ggtgtctatg ctcaaaagaa ttccataagc tctgactttt    5340
ttaaatccct ttcggatatc tcatgkatat attatccgta tttcatattc tgttgacatg    5400
caggaccggt atagagtaaa aaaacatctg ttgagtacct cttggatatc cgaaaggtgt    5460
cttatggggt ctttmtggrt attacatgtg gattctggag atacactatg cctgttattg    5520
ctaatacgca tcccaaaggy ggtgtgggta asacaacttc atccrtaaac atagktggtg    5580
aaatgaagtc tgatacagtt gatctggata ctcataccgg gctttctatc attctggggc    5640
tgagacctga tggaaaagaa atttccgtga agtacccaa acagaggat gagttaatcg    5700
atattatgac tccctacaag aacaaccata agacgttact tattgactgt ggggatttga    5760
cttcatatct taccgtact gcgattgcct ttgccgactg agttattggc ccttcaaaag    5820
actccctgac tgaacgtatt gtctgatgca tttgatggat actggacgaa atcgctctat    5880
```

```
catggggacc gatmtaactg ctcacctgta tctctgtaaa gttaatccta acaagaagaa    5940
attccctaag cttgatgcaa tcctgccatc gttcaaacat ctgaagctga tgaagagccg    6000
catttctgct cgtgcagaat tgatgatgt cattgakact ggratgggaa tcactgagyc    6060
tgttcatggg cgctattckg caggaggtaa ggaagttatt gccctgatcg aagaaattaa    6120
tcatctgatt gaaaatmaca aacagtaagg tgtatctatt gggtatccat atagtatmct    6180
ttgggctttt aatggatatc ttttargtat ctaacaaaca tcctgggtta yctcatgagc    6240
aaagcgaaat tt                                                        6252
```

<210> SEQ ID NO 11
<211> LENGTH: 2113
<212> TYPE: DNA
<213> ORGANISM: Artificial Sequence
<220> FEATURE:
<223> OTHER INFORMATION: SYNTHETIC CONSTRUCT

<400> SEQUENCE: 11

```
tagaatttcg gcatccacaa ccaatggcag gaagcccgat gcaaaaattt ttaaggagag      60
ctcttttaat gaaaattgct cagcaattac tggaggccgt tctgcaattt atgaatgcat     120
ctgcaatgac tcaggtgctg acgttgatat tcctggctct gataatacag gtactgaaaa     180
cattaattac ggcgtggata gtaagaaaac catcttcagg agagatggtt ttagaccgga     240
aacctgactc tgccgggcgt aaggatcact gcaggcagct gtctcaacaa aggaaaaaac     300
atggctgact ggtttattgc aactgaaggt gtgaaggtgg tgaaagatag tgccagcctg     360
tggccgcaga tcatcacggc ggttttgtct gccggtactg catttggtgg tgtgtggtac     420
gggcagtggc ggataacaca gcgagaggag gaagctgcaa cagcgaagct ggtcagcgaa     480
cgtctcttta ttgccacgga gctggttttt ctgctggaga ggtttgcgca gcgttgtgct     540
ccagcagcaa cagcaactgt ggagcacgat caggatggca gaggagaagc tgagttctta     600
ttcctagatt ctacgtcagt acttcaaaaa gcataatcaa agccttgata aatatgcatt     660
ccttcgaaat tcagctttca cccattgggt gaaagaaaag tgctcaaaaa tatgttaaat     720
tatcagcttt tatgactcga tatatggtaa ataatagta agaaaagtag taaaaagggg     780
ttctaattat gattaataaa attgatttca aagctaagaa tctaacatca aatgcaggtc     840
tttttctgct ccttgagaat gcaaaaagca atgggatttt tgatttatt gaaaatgacc     900 tcgtatttga taatgactca acaaataaaa tcaagatgaa tcatataaag accatgctct     960
gcggtcactt cattggcatt gataagttag aacgtctaaa gctacttcaa aatgatcccc    1020
tcgtcaacga gtttgatatt tccgtaaaag aacctgaaac agtgtcacgg tttctaggaa    1080
acttcaactt caagacaacc caaatgttta gagacattaa ttttaaagtc tttaaaaaac    1140
tgctcactaa aagtaaattg acatccatta cgattgatat tgatagtagt gtaattaacg    1200
tagaaggtca tcaagaaggt gcgtcaaaag gatataatcc taagaaactg ggaaaccgat    1260
gctacaatat ccaatttgca ttttgcgacg aattaaaagc atatgttacc ggatttgtaa    1320
gaagtggcaa tacttacact gcaaacggtg ctgcggaaat gatcaaagaa attgttgcta    1380
acatcaaatc agacgattta gaatttttat ttcgaatgga tagtggctac tttgatgaaa    1440
aaattatcga aacgatagaa tctcttggat gcaaatattt aattaaagcc aaaagttatt    1500
ctacactcac ctcacaagca acgaattcat caattgtatt cgttaaagga gaagaaggta    1560
gagaaactac agaactgtat acaaaattag ttaaatggga aaaagacaga agatttgtcg    1620
tatctcgcgt actgaaacca gaaaaagaaa gagcacaatt atcactttta gaaggttccg    1680
```

```
aatacgacta ctttttcttt gtaacaaata ctaccttgct ttctgaaaaa gtagttatat      1740
actatgaaaa gcgtggtaat gctgaaaact atatcaaaga agccaaatac gacatggcgg      1800
tgggtcatct cttgctaaag tcattttggg cgaatgaagc cgtgtttcaa atgatgatgc      1860
tttcatataa cctattttg ttgttcaagt ttgattcctt ggactcttca gaatacagac       1920
agcaaataaa gacctttcgt ttgaagtatg tatttcttgc agcaaaaata atcaaaaccg      1980
caagatatgt aatcatgaag ttgtcggaaa actatccgta caagggagtg tatgaaaaat      2040
gtctggtata ataagaatat catcaataaa attgagtgtt gctctgtgga taacttgcag      2100
agtttattaa gga                                                        2113
```

<210> SEQ ID NO 12
<211> LENGTH: 825
<212> TYPE: DNA
<213> ORGANISM: Artificial Sequence
<220> FEATURE:
<223> OTHER INFORMATION: SYNTHETIC CONSTRUCT

<400> SEQUENCE: 12

```
tgacattaac aaaaaaatta atgcaaaaga tcgtgcagcg attgccgcag cccttgagtc       60
tgtgaagctg tctgatatat cgtctaatct gaacagattc agtcgggac tgggatatgc      120 aggaaaattt acaagtcttg ctgactggat cactgagttt ggtaaggctg tccgacaga     180 gaactggcgt cctctttttg ttaaaacaga agccattata gcaggcaatg ccgcaacggc     240
tcttgttgca ctggtcttca gtattcttac cggaagcgct ttaggcatta tcgggtatgg     300
tttactgatg gctgtcaccg gtgcgctgat tgatgaatcg cttgtggaaa agcgaataa     360 gttctggggt atttaaataa aatataagac aggctgtcta tcttacagac agccttttta    420
taataacaga aagaatatat atcatactta acggaagaga taatatgaaa acagtacccg    480
tataaacagc aagcaatccc attttcccag gtgtatcagc aaaaaaaccg ctgttccaga    540
aatcaggccg ggtaaatttc agagctgtat cttcaatata ccattttgca accggataca    600
aaaccattcc gcagagagaa atacaccaga acagtaatct gtatttaaaa tcataatccc    660
atgacatata cagcatatat ccccccgtca cccatcccca ccacatatta ttaaaataat    720
attttctgtt catctgcctg ttttcctttc ttttgcactt ttgtcagtgt actgatgcat    780
gacaacacaa ccacagcatg ataataataa tcaataacaa taagc                    825
```

<210> SEQ ID NO 13
<211> LENGTH: 1212
<212> TYPE: DNA
<213> ORGANISM: Artificial Sequence
<220> FEATURE:
<223> OTHER INFORMATION: SYNTHETIC CONSTRUCT

<400> SEQUENCE: 13

```
gccttggccg tttactcctg tcgcttattg aagatgcagg gctgaataaa ctggattccc       60
tggctaatcc ccgtatccgg actaattatc gtgagtgtct tgatgccata cggcaggtta    120
cactacagca ggagtatatt cggggaagag ccttatctga aattatccat ttccggccag    180
gaatgtctga aaggtctcag gagcggttaa tggaaacgct ggagaattca gaacgacact    240
ggcctgccag aagaaagcat atgttctttc agatttttat ggcgcagcac atctgtcgtg    300
atgctgtgga aattcactgg gcgaacggta atattcaggt catcagacct gtgcggggga    360
tcagtattaa tggtgaagcg cagggcggaa tacgtccccc ttactgggtt attcttgctt    420
```

```
tttgccggag tgccgatggc agaatcatct gcagtgaagg gtatgctcat gctctttatc      480
aactgacatg tccggtgcct gtggacagca aactggaacg aaacacgctc actgctcttc      540
tgaatgtggc cagctggctt aaaagaaagc caggtacgcc ggaattaagt ctggaaaggc      600
ccctgtttga tacagaagtt tatgttaatg gtgaaaagaa atatgtactg ccggatttca      660
ttgtcacagc aagggctcct gacggaaaga cggccagagt ggtcatcgaa acgatgggat      720
atgaagacag tgattactgc gcgagaaaat ccaggcagca taccggcatg aagcagattg      780
gtgttctgca taccgatcca ccgaaatggc tggataacga tcatccccct tttaagaaac      840
atatgtacgg tgttttatg catctcaggt actgagatat tttgtggctc agttctgtaa       900
cttttcccgt aacattgtct gttgttacgg gaaagtccgg ttttgtatt gcaccagaga       960 atacccagac tgtgatgctg ccacagcgtc agcaggcttt ctgaacggtg taacatcact      1020
tcatgttaat gataatcact atcatcaaat cttgacatgc cattttctcc ttaataaatt      1080
aatactgtat atgtatccat atgcgtaagc agttaattca tttgttttcc tcagaggatg      1140
aaggagatac cgaatgtctg accctgtacg tattacaaat cccggtgcag aatcgctggg      1200
gtatgattca ga                                                         1212

<210> SEQ ID NO 14
<211> LENGTH: 186
<212> TYPE: DNA
<213> ORGANISM: Artificial Sequence
<220> FEATURE:
<223> OTHER INFORMATION: SYNTHETIC CONSTRUCT

<400> SEQUENCE: 14
gaagcctcgc ccgacagggc ggggagcagt cacgggtggt ctggaggtca tgcggcgtgt       60
cctctgcact cgccggaata aggaagtcgc cggcggctcc gcttttaccc ggccatgcgg      120
ggcatggcct tgtgggtttt cagctctgtg gcctcagcgt cgtgtgcggg ctgtgccgtg      180
cctcca                                                                186

<210> SEQ ID NO 15
<211> LENGTH: 287
<212> TYPE: DNA
<213> ORGANISM: Artificial Sequence
<220> FEATURE:
<223> OTHER INFORMATION: SYNTHETIC CONSTRUCT

<400> SEQUENCE: 15
tggtgcgggc gttttccatc actgtcatca tttgaccggt ttttctggca ggaggaacca       60
ctctggcggc tgatttttga agccggtgag gccggtcgtg gtgcaccggt acagatacgt      120
gcacttgagc agtggatgat cccgaacaag ctggagaacg caatatgatg aaatcagcga      180
aaagccgccg agaaccctcg cccaatgcgg gtggggagga aaggcggaaa agcccgaagg      240
gctttaaaaa tattattacg gtgttagcat aaaaacctgt accaatg                   287

<210> SEQ ID NO 16
<211> LENGTH: 1084
<212> TYPE: DNA
<213> ORGANISM: Artificial Sequence
<220> FEATURE:
<223> OTHER INFORMATION: SYNTHETIC CONSTRUCT

<400> SEQUENCE: 16
ggtcgtgtgg aaggaacccg ggaactggtt attcaccccc attttgttct ggtttatgag       60
gtcgacagcc agtggggaaa agtgtatgtc ctgcgcgtgt tgcataccgc acagaagtgg      120
```

```
ccataaaatt ccagtcagga ataatacttt tcattttag tttactgctc ccccagtaag      180
agcgatatat tccgaacagt cttgtctggg aggtatggtg cagtcagcga agaaccgccg      240
agaatcctcg cccaatgcgg gcggggagca gtcaccggag tcttcgccac ccgccctctg      300
tgcactgacc gggtgatcct gtcagtgagc gtggttctgc cacttcatcc gaattctttc      360
ttccagtttg ctatgcaatc cgcctccgat ccactggctg accagagctg ctgttgcaaa      420
tgaacagaaa gtcaaggcga atccatgttt aaacgtctcc ggtagttcct ggccggcgtg      480
ctgagtgatg atggaaaacc ctatatatat aataaaggta caaaaaattc ctgtgtgggc      540
gagccaggca aaccatttgg ccaccctgta taacccgtat ttcaatggca tctcccgttt      600
aatatcatga ataatcattg tatctatctt gtgggtcaga gattgaaatt ttgtaaatat      660
cataagtcct tagtccatct aaagtgagat ttaccgtatc tgaatatatc aaatgctaa      720 ggcagaatcc ccggaaattt gtgtattact tctgtagcag acacggcaaa atcgttgcat      780
tacaggtgca tctgctgggg catctgttta tcgatgcatc agatttaatg tctgacagtt      840
acttttctgt atcacccaca ctctctgctt tttcattgct actgtcatat ttatgtctgt      900
tgcgcggttt tatctgtgta tataaaatac atctgtattc attgttttct aaaaatttgc      960
gtatgttgat aaaaaatccg atttcttatt tccatattgg cacgttttta ttttcaggaa    1020
aaaaacgtca tcttctggaa tactggaaag cagaagttat catgcgggat aagtttgttt    1080
ttca                                                                 1084

<210> SEQ ID NO 17
<211> LENGTH: 1061
<212> TYPE: DNA
<213> ORGANISM: Artificial Sequence
<220> FEATURE:
<223> OTHER INFORMATION: SYNTHETIC CONSTRUCT

<400> SEQUENCE: 17
ccacataaat ccgcaaacaa aaaactttaa gaagctgcaa acctgaaaca gcaaacctgc       60
aatatagtct taaccccatt atttaatccc ctgcgttgct tcgccgcagg gaaagtctt      120 atctctgaaa ccactgtgaa caaacacaaa gaggccttcg cttgcagcgg ccaaggccgc      180
gccgctcaga atctaaaagc acctcccacg ctaacgcgcg ggccccgaac ctcaccgttc      240
tgaaaccacc gcgaaaacat caggaataaa aaacaccaca caaacgcagc accgtgccca      300
cccctcataa ctgaaaagcg aggccgcccc cgcccgaagg gcgggaacaa catcgctttt      360
aattatgaat gttgtaacta cattgtcatc gctgccagtc ttctggctgg aagtcctcag      420
tacacgctcg taagcggccc tcacggcccg ctaacgcgga gatacgcccc gacttcgggt      480
aaaccctcgt cgggaccact ccgaccgcgc acagaaactg tctcatggct gaaagcgggt      540
atggcttagc agggctgggg atgggtaagg tgaaatctat caatcagtac cggctgacgc      600
cgggcttcgg cggttttact ccggtatcac atgtaaccac agcgtgccgc cttccatgcc      660
gctggcgcgg catatcctgg tgacgatatc tgaatcgtta tatactgtgt atacgtagta      720
atgacgaggt gataaatggc acaggttaat atgagtttaa gaatcgacgc tgaactgaag      780
gatgctttta tggccgctgc aaaaagcatg gaccgtaatg ctctcagtt aattcgggat      840 tttatgcgcc agaccgttga acggcagcat aatacctggt tccgtgaaca ggttgcggca      900
ggacgtcagc aactcgagcg cggcgatgtg cttcccatg acatggtcga atcttctgcc      960
gctgcatggc gggatgaaat gagcaggaag gtttccgata aatgatggag atattctgga   1020
```

```
ccatgctggc cagccaggac aggaagcgca ttcgtgagta c                  1061

<210> SEQ ID NO 18
<211> LENGTH: 967
<212> TYPE: DNA
<213> ORGANISM: Artificial Sequence
<220> FEATURE:
<223> OTHER INFORMATION: SYNTHETIC CONSTRUCT

<400> SEQUENCE: 18
gagatactga tattgtgctt ttgtcagcca tatgctggaa gccgcattca gctcttccct    60
ggctcccgga tttagcacag ggtccgggta aatcttcatt aatccatcaa caatatcttt   120
attgacgggt tttatttcac cgccaaactt cacgaaatca atgaaggcgc tatggcgacg   180
taatgccgat actggttgaa tgtcaaaatt agccagaata aaaaagtacc ctggaaaaat   240
agcgaatatt ctttcacggt aacagcacct ggagtctgcc cgtcttatct ttcttgttat   300
taatggagtc catggtacga cgttttgctc attcagccat gagaataaag attctctgtt   360
tttgccggct gtattatatt gcgcaagata ccagttccgg ttattcaggt gttctatatt   420
cacgaagttc aacgctccgc gcaaaaccga tccatgatgg acgattttgc gatgtcaggc   480
gaatatgcta aatcatatgt ctgaagcagt atccagcccg tatctggata aactgcagtt   540
ctgacaggca tataaccagc agactctagt acgttctgta tcggtgattt ggcgaactca   600
cagataaaga acggctaagc actaatatca gcaatacagt ggcacagtat tgtgatacgc   660
gaaataaaac atcagcacgt cagttcagag taagatcgcc atatatcggg catgagccag   720
atacaaataa ctgggacacc gtctgaagtg atttgcttta ttaaagtaac ttgtgcttgg   780
tgtttatgtt tatcaatttg ggatcgcctg taaagtgcaa aatgcaattt ccatgaaagt   840 gtcccctta atggggacac ctgttcacat tttttcgttt tctttagctg tattgctaat   900
catgaaaacg aaagttcgca tcagcacagc agagcgaagt gcatcatatc cttccagatt   960
taaattc                                                            967
```